(12) United States Patent
Ichijo

(10) Patent No.: US 7,390,625 B2
(45) Date of Patent: Jun. 24, 2008

(54) APOPTOSIS-ASSOCIATED PROTEIN AND USE THEREOF

(75) Inventor: Hidenori Ichijo, Tokyo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/535,931

(22) PCT Filed: Nov. 20, 2003

(86) PCT No.: PCT/JP03/14794

§ 371 (c)(1),
(2), (4) Date: Jan. 12, 2006

(87) PCT Pub. No.: WO2004/048565

PCT Pub. Date: Jun. 10, 2004

(65) Prior Publication Data

US 2006/0240023 A1    Oct. 26, 2006

(30) Foreign Application Priority Data

Nov. 22, 2002  (JP) .............................. 2002-340077

(51) Int. Cl.
*G01N 33/53* (2006.01)
*G01N 33/567* (2006.01)
(52) U.S. Cl. ........................ 435/7.1; 435/7.21
(58) Field of Classification Search .................. None
See application file for complete search history.

(56) References Cited

U.S. PATENT DOCUMENTS 6,194,187 B1    2/2001  Miyazono et al. ........... 435/194
2004/0053233 A1*  3/2004  Lorens et al. .................. 435/6

FOREIGN PATENT DOCUMENTS

WO      WO 99/57144   * 11/1999
WO      WO02/38179      5/2002
WO      WO03/063905     8/2003

OTHER PUBLICATIONS

Burgess, Shaheen, Ravera, Jaye, Donohue, and Winkles. Possible dissociation of the heparin-binding and mitogenic activities of heparin-binding (acidic fibroblast) growth factor-1 from its receptor-binding activities by site-directed mutagenesis of a single lysine residue. 1990. Joural of Cell Biology, vol. 111, pp. 2129-2138.*
Lazar, E., Watanabe, S., Dalton, S., and Sporn, M.B. Transforming growth factor a: mutation of aspartic acid 47 and leucine 48 results in different biological activites. 1988, Molecular and Cellular Biology, vol. 8, No. 3, pp. 1247-1252.*
Schwartz, G.P., Burke, G.T., and Katsoyannis, P.G. A superactive insulin: [B10-Aspartic acid]insulin (human) 1987. Proceedings of the National Academy of Sciences, vol. 84, pp. 6408-6411.*
Lin, M.C., Wright, D.E., Hruby, V.J., and Rodbell, M. Structure-function relationships in glucagon: properties of highly purified Des-His1-, Monoiodo-, and [Des-Asn28, Thr29](homoserine lactone27)-glucagon. 1975, Biochemistry, vol. 14 No. 8, pp. 1559-1563.*
Hee-Sae Park et al., "Heat Shock Protein Hsp72 is a Negative Regulator of Apoptosis Signal-Regulating Kinase 1", Molecular and Cellular Biology, Nov. 2002, 22:7721-7730.
In-Sik Hwang et al., "Interaction of ALG-2 with ASK1 Influences ASK1 Localization and Subsequent JNK Activation", FEBS Letter 529:183-187, 2002.
Takenori Takizawa et al., "Double-stranded RNA-activated Protein Kinase Interacts with Apoptosis Signal-regulating Kinase 1", European Journal of Biochem, 269:6126-6132, 2002.
Xiangrong He et al., "ASK1 Associates with Troponin T and Induces Tropnin T Phosphorylation and Contractile Dysfunction in Cardiomyocytes", American Journal of Pathology, 163:243-251, 2003.
Iizuk H., et al., Functional analysis of ABPI, a novel apoptosis-inducing factor with ASKI binding activity, The 25th Annual Meeting of the Molecular Biology Society of Japan Program and Abstracts, IP-1067 Dec. 11-14, 2002, Yokohama, Japan.
GenBank Database Accession No. AB041651, May 24, 2002.
GenBank Database Accession No. AF116272, Jun. 14, 1999.
Ichijo, et al., "Induction of Apoptosis by ASK1, a Mammalian MAPKKK That Activates SAPK/JNK and p38 Signaling Pathways," Science, Jan. 3, 1997, vol. 275, pp. 90-94.
Leung, et al., "MRG15 Activates the *B-myb* Promoter through Formation of a Nuclear Complex with the Retinoblastoma Protein and the Novel Protein PAM14*," Journal of Biological Chemistry, Oct. 19, 2001, vol. 276, No. 42, pp. 39171-39178.
Morita, et al., "Negative Feedback Regulation of ASK1 by Protein Phosphatase 5 (PP5) in Response to Oxidative Stress," The EMBO Journal, 2001, vol. 20, No. 21, pp. 6028-6036.
Qureshi and Jackson, "Sequence-Specific DNA Binding by the *S. shibatae* TFIIB Homolog, TFB, and its Effect on Promoter Strength," Molecular Cell, Feb. 1998, vol. 1, pp. 389-400.
Tobiume, et al., "Activation of Apoptosis Signal-Regulating Kinase 1 by the Stress-Induced Activating Phosphorylation of Pre-Formed Oligomer," Journal of Cellular Physiology, 2002, vol. 191, pp. 95-104.
International Search Report, PCT/JP03/14794, Feb. 3, 2004.
European Search Report, PCT/JP0314794, Feb. 7, 2007.

* cited by examiner

*Primary Examiner*—Larry R. Helms
*Assistant Examiner*—Anne M. Gussow
(74) *Attorney, Agent, or Firm*—David G. Conlin, Esq.; Melissa Hunter-Ensor; Edwards, Angell, Palmer & Dodge, LLP

(57) ABSTRACT

The present invention provides a partial peptide comprising the functional domain of a protein comprising an amino acid sequence which is the same or substantially the same as an amino acid sequence represented by SEQ ID NO:2 or SEQ ID NO: 4; a screening method and a kit therefor for a substance which regulates ASK1 activation, or a prophylactic or therapeutic substance for diseases associated with apoptosis or inflammation, which comprises using the protein or the partial peptide or a cell which produces the same, and optionally ASK1 or a partial peptide thereof or a cell which produces the same; and an agent for regulating apoptosis or inflammatory cytokine production, or a prophylactic or therapeutic agent for diseases associated with apoptosis or inflammation, which comprises a substance for regulating an activity of a protein comprising an amino acid sequence which is the same or substantially the same as an amino acid sequence represented by SEQ ID NO:2 or SEQ ID NO: 4.

10 Claims, 10 Drawing Sheets

Fig. 1
```
human    MRPLDIV ELAEPEEVEVLEPEE DFEQFLLPVINEMREDIA    40
mouse    MRPLDAV ELAEPEEVEVLEPEE DFEQFLLPVIHEMREDIA    40
human    SLTREHGRAYLRNRSKLWEMDNMLIQIKTQVEASEESALN        80
mouse    SLTRERGRAPARNRGKLWEMDNMLIQIKTQVEASEESALN        80
human    HLQNPGDAAEGRAAKRCEKAEEKAKEIAKMAEMLVE LVRR      120
mouse    HLQGAG-GAEPRGPRA-EKADEKAQEMAKMAEMLVQ LVRR      118
human    IEKSESS                                         127
mouse    IEKSESS                                         125
```
Fig. 2A
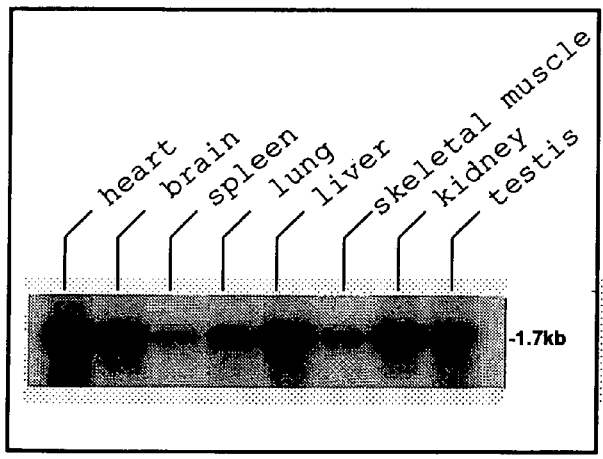
Fig. 2B
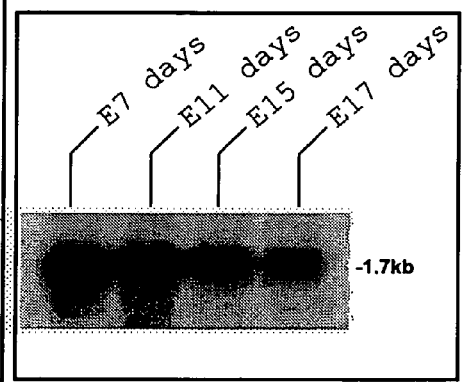

US 7,390,625 B2

SEQUENCE LISTING

<160> NUMBER OF SEQ ID NOS: 6

<210> SEQ ID NO 1
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 1

```
atg cgg ccc ctg gac atc gtc gag ctg gcg gaa ccg gag gaa gtg gag       48
Met Arg Pro Leu Asp Ile Val Glu Leu Ala Glu Pro Glu Glu Val Glu
 1               5                  10                  15 gtg ctg gag ccc gag gag gat ttc gag cag ttt ctg ctc ccg gtc atc       96
Val Leu Glu Pro Glu Glu Asp Phe Glu Gln Phe Leu Leu Pro Val Ile
            20                  25                  30 aac gag atg cgc gag gac atc gcg tcg ctg acg cgc gag cac ggg cgg      144
Asn Glu Met Arg Glu Asp Ile Ala Ser Leu Thr Arg Glu His Gly Arg
        35                  40                  45 gcg tac ctg cgg aac cgg agc aag ctg tgg gag atg gac aat atg ctc      192
Ala Tyr Leu Arg Asn Arg Ser Lys Leu Trp Glu Met Asp Asn Met Leu
    50                  55                  60 atc cag atc aaa acg cag gtg gag gcc tcg gag gag agc gcc ctc aac      240
Ile Gln Ile Lys Thr Gln Val Glu Ala Ser Glu Glu Ser Ala Leu Asn
65                  70                  75                  80 cac ctc cag aac ccg ggc gac gcg gcc gag ggc cgg gcg gcc aag agg      288
His Leu Gln Asn Pro Gly Asp Ala Ala Glu Gly Arg Ala Ala Lys Arg
                85                  90                  95 tgc gag aag gcc gag gag aag gcc aag gag att gcg aag atg gca gag      336
Cys Glu Lys Ala Glu Glu Lys Ala Lys Glu Ile Ala Lys Met Ala Glu
            100                 105                 110 atg ctg gtg gag ctg gtc cgg cgg ata gag aag agc gag tcg tcg          381
Met Leu Val Glu Leu Val Arg Arg Ile Glu Lys Ser Glu Ser Ser
        115                 120                 125
```

<210> SEQ ID NO 2
<211> LENGTH: 127
<212> TYPE: PRT
<213> ORGANISM: Homo sapiens

<400> SEQUENCE: 2

```
Met Arg Pro Leu Asp Ile Val Glu Leu Ala Glu Pro Glu Glu Val Glu
 1               5                  10                  15

Val Leu Glu Pro Glu Glu Asp Phe Glu Gln Phe Leu Leu Pro Val Ile
            20                  25                  30

Asn Glu Met Arg Glu Asp Ile Ala Ser Leu Thr Arg Glu His Gly Arg
        35                  40                  45

Ala Tyr Leu Arg Asn Arg Ser Lys Leu Trp Glu Met Asp Asn Met Leu
    50                  55                  60

Ile Gln Ile Lys Thr Gln Val Glu Ala Ser Glu Glu Ser Ala Leu Asn
65                  70                  75                  80

His Leu Gln Asn Pro Gly Asp Ala Ala Glu Gly Arg Ala Ala Lys Arg
                85                  90                  95

Cys Glu Lys Ala Glu Glu Lys Ala Lys Glu Ile Ala Lys Met Ala Glu
            100                 105                 110

Met Leu Val Glu Leu Val Arg Arg Ile Glu Lys Ser Glu Ser Ser
        115                 120                 125
```

```
<210> SEQ ID NO 3
<211> LENGTH: 375
<212> TYPE: DNA
<213> ORGANISM: Mus musculus
<220> FEATURE:
<221> NAME/KEY: CDS
<222> LOCATION: (1)..(375)

<400> SEQUENCE: 3 atg cgg ccc ctg gac gcg gtg gag ctg gcg gag ccc gag gag gtg gag      48
Met Arg Pro Leu Asp Ala Val Glu Leu Ala Glu Pro Glu Glu Val Glu
1               5                   10                  15 gtg ctg gag ccc gag gag gac ttc gag cag ttt ctg ctg ccc gtc atc      96
Val Leu Glu Pro Glu Glu Asp Phe Glu Gln Phe Leu Leu Pro Val Ile
            20                  25                  30 cac gag atg cgc gag gac atc gcg tcg ctg acg cgc gag cgc ggg cgc     144
His Glu Met Arg Glu Asp Ile Ala Ser Leu Thr Arg Glu Arg Gly Arg
        35                  40                  45 gcg ccg gcg cgc aac cgg ggc aag ctg tgg gag atg gac aat atg ctg     192
Ala Pro Ala Arg Asn Arg Gly Lys Leu Trp Glu Met Asp Asn Met Leu
    50                  55                  60 atc cag atc aag acg cag gtc gag gcc tcc gag gag agc gcc ctc aac     240
Ile Gln Ile Lys Thr Gln Val Glu Ala Ser Glu Glu Ser Ala Leu Asn
65                  70                  75                  80 cac ctg cag ggt gcc ggc ggc gcc gag ccc cgc ggc ccc cgg gcg gag     288
His Leu Gln Gly Ala Gly Gly Ala Glu Pro Arg Gly Pro Arg Ala Glu
                85                  90                  95 aag gcc gac gag aag gcg cag gag atg gcg aag atg gcc gag atg ctg     336
Lys Ala Asp Glu Lys Ala Gln Glu Met Ala Lys Met Ala Glu Met Leu
            100                 105                 110 gtg cag ctc gtg cgg cgg ata gag aag agc gag tct tcg                 375
Val Gln Leu Val Arg Arg Ile Glu Lys Ser Glu Ser Ser
        115                 120                 125

<210> SEQ ID NO 4
<211> LENGTH: 125
<212> TYPE: PRT
<213> ORGANISM: Mus musculus

<400> SEQUENCE: 4

Met Arg Pro Leu Asp Ala Val Glu Leu Ala Glu Pro Glu Glu Val Glu
1               5                   10                  15

Val Leu Glu Pro Glu Glu Asp Phe Glu Gln Phe Leu Leu Pro Val Ile
            20                  25                  30

His Glu Met Arg Glu Asp Ile Ala Ser Leu Thr Arg Glu Arg Gly Arg
        35                  40                  45

Ala Pro Ala Arg Asn Arg Gly Lys Leu Trp Glu Met Asp Asn Met Leu
    50                  55                  60

Ile Gln Ile Lys Thr Gln Val Glu Ala Ser Glu Glu Ser Ala Leu Asn
65                  70                  75                  80

His Leu Gln Gly Ala Gly Gly Ala Glu Pro Arg Gly Pro Arg Ala Glu
                85                  90                  95

Lys Ala Asp Glu Lys Ala Gln Glu Met Ala Lys Met Ala Glu Met Leu
            100                 105                 110

Val Gln Leu Val Arg Arg Ile Glu Lys Ser Glu Ser Ser
        115                 120                 125

<210> SEQ ID NO 5
<211> LENGTH: 16
<212> TYPE: PRT
```

-continued

```
<213> ORGANISM: Artificial Sequence
<220> FEATURE:
<223> OTHER INFORMATION: Oligopeptide designed to act as antigen for
      producing anti-ABP1 antibody.

<400> SEQUENCE: 5

Glu Leu Ala Glu Pro Glu Glu Val Glu Val Leu Glu Pro Glu Glu Asp
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Oligopeptide designed to act as antigen for
      producing anti-ABP1 antibody.

<400> SEQUENCE: 6

Leu Val Arg Arg Ile Glu Lys Ser Glu Ser Ser
1               5                   10
```

APOPTOSIS-ASSOCIATED PROTEIN AND USE THEREOF

CROSS-REFERENCES TO RELATED APPLICATIONS

The present application is the 35 U.S.C. §371 national stage of PCT application PCT/JP2003/014794, filed Nov. 20, 2003, which claims benefit of Japanese application 340077/2002, filed Nov. 22, 2002, the disclosures of all of which are incorporated herein by reference.

FIELD OF THE INVENTION

The present invention relates to a functional fragment of a protein that bind to ASK1 to activate, and various uses of the protein and the fragment, particularly pharmaceutical uses.

BACKGROUND ART

Apoptosis is responsible for the functions of removing cells that become no longer necessary during development and abnormal cells, of homeostasis, and of body defense reactions to remove injured cells, and its mechanisms have been elucidated gradually at the molecular level. Such molecular abnormalities and the collapse of the control mechanism damage the physiological functions of apoptosis, and result in causal factors or aggravation factors for various diseases. For example, excessively suppressed apoptosis leads to abnormal proliferation of cells to be removed originally, which in turn induces tumoral diseases, autoimmune diseases and the like. Conversely, abnormally promoted apoptosis leads to the death of cells that must exist originally, which in turn causes neurodegenerative diseases and the like.

The mitogen-activated protein (MAP) kinase cascade is a signal transduction mechanism through which MAP kinase kinase kinase (MAPKKK) activated by a physicochemical stress or an inflammatory cytokine such as tumor necrosis factor-α (TNF-α) or interleukin-1 (IL-1) sequentially activates MAP kinase kinase (MAPKK) and MAP kinase (MAPK), and cells, in response to these stimuli, exhibit phenotypes such as survival, proliferation, differentiation and death (apoptosis). c-Jun N-terminal kinase (JNK) and p38 MAP kinase (p38) are known as MAPKs that play a part of the role in the signal transduction pathway to induce apoptosis (see, for example, Science, 270, 1326 (1995)). Furthermore, they are also involved in the evoking of inflammatory reactions by inducing the production of inflammatory cytokines.

JNK and p38 are activated by MKK4/7 and MKK3/6, respectively, which are MAPKKs. These MAPKKs are activated by single MAPKKK known as apoptosis signal-regulating kinase 1 (ASK1) (JP 10-93. A, Science, 275, 90-94 (1997)). In addition to ASK1, many MAPKKKs have been reported, and ASK1 is characterized by the capability of inducing apoptosis of cells through signal transduction via the activation of JNK and/or p38. Recently, ASK1 activation has been suggested to be involved in cell differentiation such as keratinocyte differentiation and PC12 cell axon elongation as well, and ASK1 has been shown to play an important role, not only in apoptosis, but also in the control of cell fate. Furthermore, ASK1 has also been shown to be involved in the evoking of inflammatory reactions by inducing the production of inflammatory cytokines.

Because ASK1 is an important molecule that influences the subsequent fate of cells as described above, its activation is considered to be involved by various factors and undergoes complicated control. To date, it has been reported that the formation of a homo-oligomer by ASK1 molecules and the subsequent phosphorylation of threonine in the activation loop are essential to the activation of ASK1, and the phosphorylation is based mainly on auto-phosphorylation by ASK1, but the presence of another kinase has been suggested (Journal of Cellular Physiology, 191, 95-104 (2002)). On the other hand, protein phosphatase 5 (PP5) is considered to restore activated ASK1 to an inactivated state by binding directly to ASK1 under stimulation with $H_2O_2$ and dephosphorylating threonine (EMBO Journal, 20, 6028-6036 (2001)). Furthermore, it has also been reported that thioredoxin, a redox control factor, acts as an ASK1 activation inhibitor as constitutively bound to the N-terminal domain of ASK1 in the absence of oxidation stress and leaves ASK1 upon exposure to oxidation stress and hence causes the activation of ASK1 (EMBO Journal, 17, 2596-2606 (1998)), that during the activation of ASK1 by TNF-α, TNF receptor-associated factor 2 (TRAF2) binds to the C-terminal domain of ASK1 to cause the activation of ASK1 (Molecular Cell, 2, 389-395 (1998)), and that the 14-3-3 protein inhibits the activation of ASK1 by binding to the C-terminal domain (Proceedings of National Academy of Sciences, USA, 96, 8511-8515 (1999)).

Because treating cells of an ASK1 knockout mouse with an endoplasmic reticulum stress inducer significantly suppresses apoptosis compared to cells of a wild-type mouse, it is suggested that ASK1 is closely associated with the induction of apoptosis by endoplasmic reticulum stress, and that the above-described ASK1 inhibitors such as thioredoxin and the 14-3-3 protein, ASK1 dominant negative variants, ASK1 antisense oligonucleotides and the like are effective in the prophylaxis or treatment of diseases associated with endoplasmic reticulum stress, such as neurodegenerative diseases (e.g., polyglutamine disease and the like) (WO 02/38179). Nishitoh et al. showed that the accumulation of an abnormal protein in polyglutamine disease evokes endoplasmic reticulum stress, hence leads to the formation of a tripartite complex of the stress sensor molecule IRE1, TRAF2 and ASK1 and activates ASK1, and induces apoptosis (=nerve cell death) via the activation of JNK (Genes Development, 16, 1345-1355 (2002)).

Although the physiological importance of ASK1 and its association with disease have been elucidated gradually as described above, much remains unknown about the mechanisms of ASK1 activation control and apoptosis induction/inflammatory reaction evoking via ASK1, due partially to the complexity thereof, and there is a demand for further advances in the relevant research.

Accordingly, the present invention is directed to provide new findings on the mechanisms of activation of ASK1 and the mechanisms of apoptosis induction/inflammatory reaction evoking mediated thereby. That is, it is an object of the present invention to identify a novel ASK1-binding protein that has not been known to date, and to elucidate how ASK1 activation is regulated by the protein. It is another object of the present invention to provide a novel prophylactic or therapeutic means for various diseases involved by ASK1, on the basis of the interaction of the protein and ASK1.

SUMMARY OF THE INVENTION

With the aim of accomplishing the above-described objects, the present inventors screened an expression library derived from fetal human brain by the yeast two-hybrid method with human ASK1 full-length cDNA as a bait, succeeded in cloning a protein of unknown function that consists of the 127 amino acids encoded by a known gene designated as PGR1 as a new ASK1-binding protein, and designated the protein as ASK1 Binding Protein 1 (hereinafter abbreviated as "ABP1"). Furthermore, the present inventors found that this protein not only binds to ASK1, but also activates ASK1, as well as JNK and p38, which are located downstream of ASK1, and induces caspase-dependent apoptosis. The present inventors conducted further investigations based on these findings, and developed the present invention.

Accordingly, the present invention provides:

[1] a peptide that comprises the same or substantially the same amino acid sequence as a portion of the amino acid sequence shown by SEQ ID NO:2 or SEQ ID NO:4, and that is capable of activating ASK1, or a salt thereof,

[2] the peptide described in [1] above, which comprises the same or substantially the same amino acid sequence as a partial amino acid sequence consisting of about 60 amino acids or more in the amino acid sequence shown by SEQ ID NO:2 or SEQ ID NO:4, or a salt thereof,

[3] the peptide described in [2] above, wherein the partial amino acid sequence is a sequence on the N-terminal side, or a salt thereof,

[4] a polynucleotide that comprises the base sequence encoding the peptide described in [1] above,

[5] the polynucleotide described in [4] above, which comprises the same or substantially the same base sequence as a portion of the base sequence shown by SEQ ID NO:1 or SEQ ID NO:3,

[6] a recombinant vector comprising the polynucleotide described in [4] above,

[7] a transformant obtained by transforming a host with the recombinant vector described in [6] above,

[8] a method of producing the peptide described in [1] above or a salt thereof, which comprises cultivating the transformant described in [7] above, and recovering said peptide or a salt thereof from the culture obtained,

[9] a peptide that comprises the same or substantially the same amino acid sequence as a portion of the amino acid sequence shown by SEQ ID NO:2 or SEQ ID NO:4, and that does not activate or is capable of inactivating ASK1, or a salt thereof,

[10] the peptide described in [9] above, which comprises the same or substantially the same amino acid sequence as a partial amino acid sequence consisting of about 35 amino acids or less in the amino acid sequence shown by SEQ ID NO:2 or SEQ ID NO:4, or a salt thereof,

[11] the peptide described in [10] above, wherein the partial amino acid sequence is a sequence on the N-terminal side, or a salt thereof,

[12] an agent for promoting ASK1 activation, containing a protein that comprises the same or substantially the same amino acid sequence as the amino acid sequence shown by SEQ ID NO:2 or SEQ ID NO:4, or the peptide described in [1] above, or a salt thereof,

[13] the agent described in [12] above, which is an agent for inducing apoptosis,

[14] a pharmaceutical containing a protein that comprises the same or substantially the same amino acid sequence as the amino acid sequence shown by SEQ ID NO:2 or SEQ ID NO:4, or the peptide described in [1] above, or a salt thereof,

[15] the pharmaceutical described in [14] above, which is a prophylactic or therapeutic agent for a disease in which induction of apoptosis is effective for the prophylaxis or therapy thereof,

[16] the pharmaceutical described in [15] above, wherein the disease is selected from a group consisting of cancers, autoimmune diseases, viral infections, endocrine diseases, hematological diseases, organ hyperplasia, post-angioplastic restenosis and recurrence after cancer resection,

[17] an agent for promoting ASK1 activation, containing a polynucleotide that comprises the base sequence that encodes a protein that comprises the same or substantially the same amino acid sequence as the amino acid sequence shown by SEQ ID NO:2 or SEQ ID NO:4 or the peptide described in [1] above,

[18] the agent described in [17] above, which is an agent for inducing apoptosis,

[19] a pharmaceutical containing a polynucleotide that comprises the base sequence that encodes a protein that comprises the same or substantially the same amino acid sequence as the amino acid sequence shown by SEQ ID NO:2 or SEQ ID NO:4 or the peptide described in [1] above,

[20] the pharmaceutical described in [19] above, which is a prophylactic or therapeutic agent for a disease in which induction of apoptosis is effective for the prophylaxis or therapy thereof,

[21] the pharmaceutical described in [20] above, wherein the disease is selected from the group consisting of cancers, autoimmune diseases, viral infections, endocrine diseases, hematological diseases, organ hyperplasia, post-angioplastic restenosis and recurrence after cancer resection,

[22] a diagnostic reagent for a disease associated with apoptosis or inflammation, which contains a polynucleotide that comprises the base sequence that encodes a protein that comprises the same or substantially the same amino acid sequence as the amino acid sequence shown by SEQ ID NO:2 or SEQ ID NO:4, or a portion thereof,

[23] the diagnostic reagent described in [22] above, wherein the disease is selected from the group consisting of cancers, autoimmune diseases, viral infections, endocrine diseases, hematological diseases, organogenesis abnormality, post-angioplastic restenosis, recurrence after cancer resection, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases,

[24] an agent for inhibiting ASK1 activation, containing a polynucleotide that comprises a base sequence complementary to the base sequence that encodes a protein that comprises the same or substantially the same amino acid sequence as the amino acid sequence shown by SEQ ID NO:2 or SEQ ID, or a portion thereof,

[25] the agent described in [24] above, which is an agent for suppressing apoptosis or inflammatory cytokine production,

[26] a pharmaceutical containing a polynucleotide that comprises a base sequence complementary to the base sequence that encodes a protein that comprises the same or substantially the same amino acid sequence as the amino acid sequence shown by SEQ ID NO:2 or SEQ ID NO:4, or a portion thereof,

[27] the pharmaceutical described in [26] above, which is a prophylactic or therapeutic agent for a disease in which suppression of apoptosis or inflammation is effective for the prophylaxis or therapy thereof,

[28] the pharmaceutical described in [27] above, wherein the disease is selected from the group consisting of viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases,

[29] an antibody against a protein that comprises the same or substantially the same amino acid sequence as the amino acid sequence shown by SEQ ID NO:2 or SEQ ID NO:4 or a salt thereof, which is capable of specifically recognizing the amino acid sequence shown by SEQ ID NO:5 or SEQ ID NO:6,

[30] a diagnostic reagent for a disease associated with apoptosis or inflammation, which contains an antibody against a protein that comprises the same or substantially the same amino acid sequence as the amino acid sequence shown by SEQ ID NO:2 or SEQ ID NO:4 or a salt thereof,

[31] the diagnostic reagent described in [30] above, wherein the disease is selected from the group consisting of cancers, autoimmune diseases, viral infections, endocrine diseases, hematological diseases, organogenesis abnormality, postangioplastic restenosis, recurrence after cancer resection, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases,

[32] an agent for inhibiting ASK1 activation, containing an antibody against a protein that comprises the same or substantially the same amino acid sequence as the amino acid sequence shown by SEQ ID NO:2 or SEQ ID NO:4 or a salt thereof,

[33] the agent described in [32] above, which is an agent for suppressing apoptosis or inflammatory cytokine production,

[34] a pharmaceutical containing an antibody against a protein that comprises the same or substantially the same amino acid sequence as the amino acid sequence shown by SEQ ID NO:2 or SEQ ID NO:4 or a salt thereof,

[35] the pharmaceutical described in [34] above, which is a prophylactic or therapeutic agent for a disease in which suppression of apoptosis or inflammation is effective for the prophylaxis or therapy thereof,

[36] the pharmaceutical described in [35] above, wherein the disease is selected from the group consisting of viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases,

[37] a screening method for a substance which regulates ASK1 activation, which comprises using a protein that comprises the same or substantially the same amino acid sequence as the amino acid sequence shown by SEQ ID NO:2 or SEQ ID NO:4, the peptide described in [1] above, or a salt thereof, or a cell that produces the same,

[38] the method described in [37] above, which comprises further using ASK1, a partial peptide thereof containing an N-terminal activation control domain, or a salt thereof, or a cell that produces the same,

[39] the method described in [38] above, which comprises measuring the binding ability of a protein that comprises the same or substantially the same amino acid sequence as the amino acid sequence shown by SEQ ID NO:2 or SEQ ID NO:4, the peptide described in [1] above, or a salt thereof, and ASK1, or a partial peptide thereof containing an N-terminal activation control domain, or a salt thereof,

[40] a screening kit for a substance which regulates ASK1 activation, which includes a protein that comprises the same or substantially the same amino acid sequence as the amino acid sequence shown by SEQ ID NO:2 or SEQ ID NO:4, the peptide described in [1] above, or a salt thereof, or a cell that produces the same,

[41] the kit described in [40] above, which further includes ASK1, a partial peptide thereof containing an N-terminal activation control domain or a salt thereof, or a cell that produces the same,

[42] the method described in [38] above, which comprises comparing the activation of ASK1, a partial peptide thereof containing an N-terminal activation control domain and a kinase domain, or a salt thereof, in a cell that produces ASK1, said partial peptide or a salt thereof, between (1) in the presence of a protein that comprises the same or substantially the same amino acid sequence as the amino acid sequence shown by SEQ ID NO:2 or SEQ ID NO:4, or the peptide described in [1] above, or a salt thereof, and (2) in the presence of a protein that comprises the same or substantially the same amino acid sequence as the amino acid sequence shown by SEQ ID NO:2 or SEQ ID NO:4, or the peptide described in [1] above, or a salt thereof, and a test substance,

[43] the method described in [38] above, which comprises comparing the activation of (1) a protein that comprises the same or substantially the same amino acid sequence as the amino acid sequence shown by SEQ ID NO:2 or SEQ ID NO:4, or the peptide described in [1] above, or a salt thereof, and (2) ASK1, a partial peptide thereof containing an N-terminal activation control domain and a kinase domain, or a salt thereof, in a cell that produces ASK1, or said partial peptide, or a salt thereof, in the presence and absence of a test substance,

[44] a screening method for a substance which regulates ASK1 activation, which comprises comparing the expression of a protein that comprises the same or substantially the same amino acid sequence as the amino acid sequence shown by SEQ ID NO:2 or SEQ ID NO:4, or the peptide described in [1] above, or a salt thereof, in a cell that produces said protein, said peptide, or a salt thereof, in the presence and absence of a test substance,

[45] the method described in [44] above, which comprises using a polynucleotide that comprises the base sequence that encodes a protein that comprises the same or substantially the same amino acid sequence as the amino acid sequence shown by SEQ ID NO:2 or SEQ ID NO:4, or a portion thereof, or an antibody against a protein that comprises the same or substantially the same amino acid sequence as the amino acid sequence shown by SEQ ID NO:2 or SEQ ID NO:4 or a salt thereof,

[46] a screening kit for a substance which regulates ASK1 activation, which includes a polynucleotide that comprises the base sequence that encodes a protein that comprises the same or substantially the same amino acid sequence as the amino acid sequence shown by SEQ ID NO:2 or SEQ ID NO:4, or a portion thereof, or an antibody against a protein that comprises the same or substantially the same amino acid sequence as the amino acid sequence shown by SEQ ID NO:2 or SEQ ID NO:4 or a salt thereof,

[47] an agent for inducing apoptosis, containing a substance that increases the expression or activity of a protein that comprises the same or substantially the same amino acid sequence as the amino acid sequence shown by SEQ ID NO:2 or SEQ ID NO:4 or a salt thereof,

[48] a pharmaceutical containing a substance that increases the expression or activity of a protein that comprises the same or substantially the same amino acid sequence as the amino acid sequence shown by SEQ ID NO:2 or SEQ ID NO:4 or a salt thereof,

[49] the pharmaceutical described in [48] above, which is a prophylactic or therapeutic agent for a disease in which induction of apoptosis is effective for the prophylaxis or therapy thereof,

[50] the pharmaceutical described in [49] above, wherein the disease is selected from the group consisting of cancers, autoimmune diseases, viral infections, endocrine diseases, hematological diseases, organ hyperplasia, post-angioplastic restenosis and recurrence after cancer resection,

[51] an agent for suppressing apoptosis or inflammatory cytokine production, containing a substance that decreases the expression or activity of a protein that comprises the same or substantially the same amino acid sequence as the amino acid sequence shown by SEQ ID NO:2 or SEQ ID NO:4 or a salt thereof,

[52] a pharmaceutical containing a substance that decreases the expression or activity of a protein that comprises the same or substantially the same amino acid sequence as the amino acid sequence shown by SEQ ID NO:2 or SEQ ID NO:4 or a salt thereof,

[53] the pharmaceutical described in [52] above, which is a prophylactic or therapeutic agent for a disease in which suppression of apoptosis or inflammation is effective for the prophylaxis or therapy thereof, and

[54] the pharmaceutical described in [53] above, wherein the disease is selected from the group consisting of viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases.

The present invention also provides:

[55] an agent for inhibiting a protein that comprises the same or substantially the same amino acid sequence as the amino acid sequence shown by SEQ ID NO:2 or SEQ ID NO:4 or a salt thereof, which contains an ASK1 partial peptide that comprises an N-terminal activation control domain of ASK1 and does not comprise a kinase domain, or a salt thereof,

[56] the agent described in [55] above, which is an agent for suppressing apoptosis or inflammatory cytokine production,

[57] a pharmaceutical containing an ASK1 partial peptide comprising an N-terminal activation control domain of ASK1 and does not comprise a kinase domain, or a salt thereof,

[58] the pharmaceutical described in [57] above, which is a prophylactic or therapeutic agent for a disease in which suppression of apoptosis or inflammation is effective for the prophylaxis or therapy thereof,

[59] the pharmaceutical described in [57], wherein the disease is selected from the group consisting of viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases,

[60] an agent for inhibiting ASK1 activation, containing the peptide described in [9] above or a salt thereof,

[61] the agent described in [60] above, which is an agent for suppressing apoptosis or inflammatory cytokine production,

[62] a pharmaceutical containing the peptide described in [9] above or a salt thereof,

[63] the pharmaceutical described in [62] above, which is a prophylactic or therapeutic agent for a disease in which suppression of apoptosis or inflammation is effective for the prophylaxis or therapy thereof, and

[64] the pharmaceutical described in [63] above, wherein the disease is selected from the group consisting of viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammatory diseases, ischemic neuropathy, diabetic neuropathy, vascular diseases, respiratory diseases and articular diseases.

BRIEF DESCRIPTION OF THE DRAWINGS

FIG. 1 shows the alignments of the human (upper lane) and mouse (lower lane) ABP1 amino acid sequences. The portion surrounded by the square shows the partial amino acid sequence used as an antigen to prepare an antibody. The partial sequence used as an antigen peptide to prepare two kinds of antibodies of the present invention (ELA antibody and LVR antibody) is indicated by the box.

FIG. 2A shows a tissue distribution of the expression of ABP1 mRNA in mouse tissues. FIG. 2B shows changes over time in the expression of ABP1 mRNA in fetal mouse tissues.

FIG. 4A: HEK293 cells were transfected with Flag-ABP1 and the Myc-ASK1 plasmid, the cells were recovered after 24 hours, immunoprecipitation with an anti-Flag antibody was conducted, and immunoblot analysis was conducted using an anti-Myc antibody. FIG. 4B: HEK293 cells were transfected with Flag-ASK1 and the CFP-ABP1 plasmid, the cells were recovered after 24 hours, immunoprecipitation with an anti-Flag antibody was conducted, and immunoblot analysis was conducted using an anti-GFP antibody. Note that CFP is a variant of GFP and can be recognized by an anti-GFP antibody. For both FIGS. 4A and B, the two right lanes show the results obtained with $H_2O_2$ treatment (0.5 mM, 1 hour). The lower panel shows the results of separate electrophoresis of a portion of each cell lysate before immunoprecipitation. IP stands for immunoprecipitation, and IB stands for immunoblot.

FIG. 6A: Fluorescence photomicrographs at 36 hours after HeLa cells were transfected with CFP or the CFP-ABP1 plasmid (upper panel) and differential interference photomicrographs for the same fields (lower panel) are shown. FIG. 6B: The ratio (%) of cell death at 36 hours after transfection is shown.

FIG. 7A: Phase contrast photomicrographs at 36 hours after cultivation of PAE-ABP1 cells in the presence (+) and absence (−) of tetracycline (Tet) are shown. FIG. 7B: The ratio (%) of cell death from cultivation in the presence of tetracycline (O hour) and at 24 hours and 48 hours after removal of tetracycline.

FIG. 9A: PAE-ABP1 cells were cultivated in the absence of tetracycline, and caspase-3 activity was measured after 0, 12, 24, and 36 hours. The results are shown as relative values with the value in the presence of tetracycline taken as 1. FIG. 9B: PAE-ABP1 cells were treated with zVAD-fmk (50 μM) simultaneously with removal of tetracycline, and the ratio (%) of dead cells was quantified. Cell death assay was conducted at 18 hours after removal of tetracycline. Tet stands for tetracycline.

FIG. 10A: A schematic diagram of the ABP1-deficient variant is shown. Each variant had a CFP tag added to the N-terminal side thereof as with the wild type. FIG. 10B: The ratio (%) of cell death at 36 hours after transfection in cells introduced with the ABP1-deficient variant is shown.

FIG. 11A: PAE-ABP1 cells were cultivated in the absence of tetracycline, the activation of endogenous JNK and p38 was examined by immunoblot analysis using each anti-phosphorylated protein antibody. FIG. 11B: PAE-ABP1 cells were cultivated in the absence of tetracycline, the activation of endogenous ASK1 was examined by immunoblot analysis using an anti-phosphorylated protein antibody. IB stands for immunoblot.

BEST MODE FOR EMBODIMENT OF THE INVENTION

Figure 3:
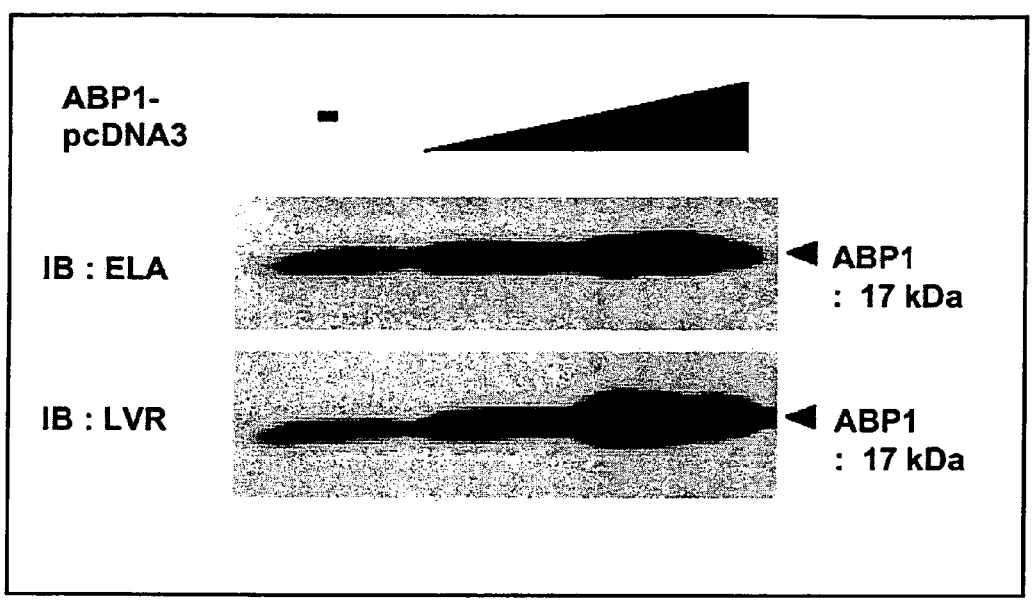
FIG. 3 shows plasmid-content-dependent increases in detected intensity observed when HEK293 cells were transfected with a plasmid that expresses untagged ABP1 to allow the overexpression of the ABP1 protein. At 24 hours after transfection, the cells were recovered, each cell extract was divided into two portions and subjected to SDS-PAGE, and immunoblot (IB) was conducted using the ELA antibody and the LVR antibody. ABP1-pcDNA3(−) stands for untransformed HEK293 cells, and the gradient indicates that the plasmid content increases from left to right.

The protein used in the present invention (hereinafter referred to as "the ABP1 of the present invention" or simply as "ABP1") is a protein that comprises the same or substantially the same amino acid sequence as the amino acid sequence shown by SEQ ID NO:2 or SEQ ID NO:4.

The ABP1 of the present invention may be a protein derived from a cell (e.g., hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or a corresponding precursor cell, stem cell or cancer cell thereof, and the like) of a warm-blooded animal (for example, human, mouse, rat, guinea pig, hamster, rabbit, sheep, goat, swine, bovine, horse, bird, cat, dog, monkey, chimpanzee and the like), or any tissue where such cells are present, for example, brain or any portion of brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine and small intestine), blood vessel, heart, thymus, spleen, submandibular gland, peripheral blood, prostate, testicle, ovary, placenta, uterus, bone, joint, skeletal muscle, and the like, and may also be a chemically synthesized protein or a protein synthesized using a cell-free translation system. Alternatively, the ABP1 of the present invention may be a recombinant protein produced by a transformant introduced with a polynucleotide having the base sequence that encodes the above-described amino acid sequence.

As "substantially the same amino acid sequence" as the amino acid sequence shown by SEQ ID NO:2 or SEQ ID NO:4, an amino acid sequence having a homology of about 70% or more, preferably about 80% or more, more preferably about 90% or more, particularly preferably about 95% or more, and most preferably about 98% or more, to the amino acid sequence shown by SEQ ID NO:2 or SEQ ID NO:4, and the like can be mentioned.

As examples of "the protein that comprises substantially the same amino acid sequence" as the amino acid sequence shown by SEQ ID NO:2 or SEQ ID NO:4, a protein that comprises substantially the same amino acid sequence as the aforementioned amino acid sequence shown by SEQ ID NO:2 or SEQ ID NO:4, and that has substantially the same quality of activity as a protein that comprises the amino acid sequence shown by SEQ ID NO:2 or SEQ ID NO:4, and the like are preferred.

As examples of "substantially the same quality of activity", activity to promote the activation of ASK1 or a group of kinases located downstream thereof (e.g., MKK4/7, MKK3/6, JNK, p38 and the like), activity to induce cell apoptosis, and the like can be mentioned. Substantially the same quality means that the proteins of interest are qualitatively (e.g., physiologically or pharmacologically) equivalent to each other. Accordingly, it is preferable that the proteins be equivalent to each other in terms of activities such as to promote the activation of the ASK1 cascade, but quantitative factors such as the extent of these activities and the molecular weights of the proteins may be different (for example, differences within the range of about 0.01 to 100 times, preferably about 0.1 to 10 times, more preferably 0.5 to 2 times, with respect to activity, can be mentioned).

A measurement of the activity to promote the activation of the ASK1 cascade can be conducted by a publicly known method, for example, the detection of the phosphorylation of ASK1 or a group of kinases located downstream thereof (e.g., MKK4/7, MKK3/6, JNK, p38 and the like) using a labeled phosphate donor, and the like, and a measurement of activity to induce apoptosis can be conducted by a measurement of cell death induction rate, morphological observation of cells, detection of DNA fragmentation, and the like.

Examples of the ABP1 of the present invention also include what is called muteins of proteins that comprise (1) an amino acid sequence having one or two or more amino acids (preferably about 1 to 30, preferably about 1 to 10, more preferably several (1 to 5) amino acids) deleted from the amino acid sequence shown by SEQ ID NO:2 or SEQ ID NO:4, (2) an amino acid sequence having one or two or more amino acids (preferably about 1 to 30, preferably about 1 to 10, more preferably several (1 to 5) amino acids) added to the amino acid sequence shown by SEQ ID NO:2 or SEQ ID NO:4, (3) an amino acid sequence having one or two or more amino acid (preferably about 1 to 30, preferably about 1 to 10, more preferably several (1 to 5) amino acids) inserted to the amino acid sequence shown by SEQ ID NO:2 or SEQ ID NO:4, (4) an amino acid sequence having one or two or more amino acids (preferably about 1 to 30, preferably about 1 to 10, more preferably several (1 to 5) amino acids) substituted with other amino acids in the amino acid sequence shown by SEQ ID NO:2 or SEQ ID NO:4, or (5) an amino acid sequence as a combination thereof.

When an amino acid sequence is inserted, deleted or substituted as described above, the position of the insertion, deletion or substitution is not subject to limitation, as long as the protein activity is retained.

The ABP1 of the present invention is preferably human ABP1 (hABP1) having the amino acid sequence shown by SEQ ID NO:2, or mouse ABP1 (mABP1) having the amino acid sequence shown by SEQ ID NO:4, or a homologue thereof in another warm-blooded animal (for example, rat, guinea pig, hamster, rabbit, sheep, goat, swine, bovine, horse, bird, cat, dog, monkey, chimpanzee and the like). hABP1 is a protein consisting of the 127 amino acids encoded by a known gene of human T cell origin designated as PGR1 (GenBank registration number: AF116272), but no report has been presented on the function thereof. Also, mouse ABP1 is a protein consisting of the 125 amino acids encoded by cDNA of mouse brain origin designated as clone MNCb-1039 (Gen-Bank registration number: AB041651), and no report is available on the function thereof.

With respect to the proteins mentioned herein, the left end is the N-terminal (amino terminal) and the right end is the C terminal (carboxyl terminal) in accordance with the conventional peptide marking. For the ABP1 of the present invention, including a protein that comprises the amino acid sequence shown by SEQ ID NO:2 or SEQ ID NO:4, the C terminal may be any of a carboxyl group (—COOH), a carboxylate (—COO⁻), an amide (—CONH$_2$), and an ester (—COOR).

Here, as R in the ester, a $C_{1-6}$ alkyl group such as methyl, ethyl, n-propyl, isopropyl and n-butyl; a $C_{3-8}$ cycloalkyl group such as cyclopentyl and cyclohexyl; a $C_{6-12}$ aryl group such as phenyl and α-naphthyl; a phenyl-$C_{1-2}$ alkyl group such as benzyl and phenethyl; a $C_{7-14}$ aralkyl group such as an α-naphthyl-$C_{1-2}$ alkyl group such as α-naphthylmethyl; a pivaloyloxymethyl group; and the like can be used.

When ABP1 has a carboxyl group (or a carboxylate) in addition to that on the C terminal, one in which the carboxyl group is amidated or esterified is also included in the ABP1 of the present invention. In this case, as the ester, the above-described C-terminal ester and the like, for example, can be used.

Furthermore, the ABP1 of the present invention also includes a protein wherein the amino group of the N-terminal amino acid residue thereof (e.g., methionine residue) is protected by a protecting group (for example, a $C_{1-6}$ acyl group such as a $C_{1-6}$ alkanoyl group such as a formyl group or an acetyl group, and the like), a protein wherein the N-terminal glutamine residue, which is produced by cleavage in vivo, has been converted to pyroglutamic acid, a protein wherein a substituent (for example, —OH, —SH, an amino group, an imidazole group, an indole group, a guadinino group and the like) on an amino acid side chain in the molecule is protected by an appropriate protecting group (for example, a $C_{1-6}$ acyl group such as a $C_{1-6}$ alkanoyl group such as a formyl group or an acetyl group, and the like), a conjugated protein such as what is called a glycoprotein, which has a sugar chain bound thereto, and the like.

The present invention provides a peptide having the above-described partial amino acid sequence of ABP1, and that has substantially the same quality of activity as ABP1. Here, "substantially the same quality of activity" has the same definition as above. A measurement of "substantially the same quality of activity" can be conducted in the same manner as above. In the present specification, this partial peptide is hereinafter referred to as "the activating peptide of the present invention".

The activating peptide of the present invention is not subject to limitation, as long as it has the above-described nature; as examples thereof, a peptide that comprises the same or substantially the same amino acid sequence as a partial amino acid sequence consisting of about 60 amino acids or more, preferably about 60 to about 100 amino acids, more preferably about 60 to about 80 amino acids, in the amino acid sequence shown by SEQ ID NO:2 or SEQ ID NO:4, and the like can be mentioned. The partial amino acid sequence may be a sequence of ABP1 on the N-terminal side, a sequence on the C-terminal side, or an internal sequence. Alternatively, the partial amino acid sequence may be a combination of such partial sequences.

Preferably, the activating peptide of the present invention comprises a partial amino acid sequence that comprises about 60 amino acids or more, more preferably about 60 to about 100 amino acids, particularly preferably about 60 to about 80 amino acids, on the N-terminal side of the amino acid sequence shown by SEQ ID NO:2 or SEQ ID NO:4.

In a particularly preferable scope, the activating peptide of the present invention in some cases exhibits even higher activity (e.g., activity to promote the activation of the ASK1 cascade, activity to induce apoptosis, and the like) than that of the full-length protein.

On the other hand, the partial peptide of ABP1 includes one capable of functioning as an (antagonistic) substance for inhibiting ABP1 or "the activating peptide of the present invention". As such partial peptides, those that have activity to bind to ASK1 but are incapable of activating the kinase can be mentioned. In the present specification, this partial peptide is hereinafter referred to as "the inhibitory peptide of the present invention".

Accordingly, the inhibitory peptide of the present invention is a peptide that comprises the same or substantially the same amino acid sequence as a portion of the amino acid sequence shown by SEQ ID NO:2 or SEQ ID NO:4, and that does not activate or is capable of inactivating ASK1. As examples of the inhibitory peptide, a peptide that comprises a partial amino acid sequence consisting of about 35 amino acids or less in the amino acid sequence shown by SEQ ID NO:2 or SEQ ID NO:4, preferably a partial amino acid sequence on the N-terminal side, can be mentioned.

With respect to the partial peptide of ABP1 of the present invention (encompassing both of the activating peptide of the present invention and the inhibitory peptide of the present invention; hereinafter also simply abbreviated as "the partial peptide of the present invention"), the C-terminal may be any of a carboxyl group (—COOH), a carboxylate (—COO⁻), an amide (—CONH₂), and an ester (—COOR). Here, as R in the ester, the same as those mentioned for ABP1 above can be mentioned. When these peptides have a carboxyl group (or a carboxylate) in addition to that on the C terminal, one in which the carboxyl group is amidated or esterified is also included in the partial peptide of the present invention. In this case, as the ester, the above-described C-terminal ester and the like, for example, can be used.

Furthermore, the partial peptide of the present invention also includes a protein wherein the amino group of the N-terminal methionine residue is protected by a protecting group, a protein wherein Gln, which is produced by cleavage on the N-terminal side in vivo, has been converted to pyroglutamic acid, a protein wherein a substituent on an amino acid side chain in the molecule is protected by an appropriate protecting group, a conjugated peptide such as what is called a glycopeptide, which has a sugar chain bound thereto, and the like, as with the above-described ABP1.

As the salt of the ABP1 of the present invention or a partial peptide thereof, a physiologically acceptable salt with an acid or a base can be mentioned, with preference given to a physiologically acceptable acid addition salt. Useful salts include, for example, salts with inorganic acids (for example, hydrochloric acid, phosphoric acid, hydrobromic acid, sulfuric acid) or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The ABP1 of the present invention or a salt thereof can be produced from cells or a tissue of the aforementioned warm-blooded animal by a method of protein purification known per se. Specifically, ABP1 or a salt thereof can be produced by homogenizing a tissue or cells of a warm-blooded animal, and separating and purifying the soluble fraction by a chromatography such as reversed-phase chromatography, ion exchange chromatography or affinity chromatography, and the like.

The ABP1 of the present invention or a partial peptide thereof or a salt thereof (hereinafter also comprehensively referred to as "the ABP1 species of the present invention") can also be produced according to a publicly known peptide synthesis process.

The peptide synthesis process may be any of, for example, a solid phase synthesis process and a liquid phase synthesis process. A desired protein can be produced by condensing a partial peptide or amino acids capable of constituting ABP1 with the remaining portion, and removing the protecting group if any in the resultant product.

Here, the condensation and the removal of the protecting group are conducted according to methods known per se, for example, methods described in [1] to [5] below.
[1] M. Bodanszky and M. A. Ondetti: Peptide Synthesis, Interscience Publishers, New York (1966)
[2] Schroeder and Luebke: The Peptide, Academic Press, New York (1965)
[3] Nobuo Izumiya, et al.: Peptide Gosei-no-Kiso to Jikken, published by Maruzen Co. (1975);
[4] Haruaki Yajima and Shunpei Sakakibara: Seikagaku Jikken Koza 1, Tanpakushitsu no Kagaku IV, 205 (1977)
[5] Haruaki Yajima, ed.: Zoku Iyakuhin no Kaihatsu, Vol. 14, Peptide Synthesis, published by Hirokawa Shoten.

The ABP1 species thus obtained can be isolated and purified by a publicly known method of purification. Here, as examples of the method of purification, solvent extraction, distillation, column chromatography, liquid chromatography, recrystallization, a combination thereof, and the like can be entioned.

When the protein (peptide) obtained by the above-described method is a free form, the free form can be converted to an appropriate salt by a publicly known method or a method based thereon; conversely, when the protein (peptide) is obtained in the form of a salt, the salt can be converted to a free form or another salt by a publicly known method or a method based thereon.

For the synthesis of the ABP1 species of the present invention, an ordinary commercially available resin for protein synthesis can be used. As examples of such resins, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin and the like can be mentioned. Using such a resin, an amino acid having an appropriately protected α-amino group and side chain functional group is condensed on the resin in accordance with the sequence of the desired protein or peptide (hereinafter also generically referred to as "protein or the like") according to various methods of condensation known per se. At the end of the reaction, the protein or the like is cleaved from the resin, various protecting groups are removed simultaneously, and a reaction to form an intramolecular disulfide bond is carried out in a highly diluted solution to obtain the desired protein or the like or an amide thereof.

For the above-described condensation of protected amino acids, various activation reagents useful for protein synthesis can be used, with preference given to a carbodiimide. As the carbodiimide, DCC, N,N'-diisopropylcarbodiimide, N-ethyl-N'-(3-dimethylaminoprolyl)carbodiimide and the like can be used. For the activation using these carbodiimides, the protected amino acid, along with a racemation-suppressing additive (for example, HOBt, HOOBt), may be added directly to the resin, or the protected amino acid may be activated in advance as a symmetric acid anhydride, or HOBt ester or HOOBt ester and then added to the resin.

A solvent used for activation of protected amino acids and condensation of protected amino acids with a resin can be appropriately selected from among solvents that are known to be usable for protein condensation reactions. Examples of such useful solvents include acid amides such as N,N-dimethylformamide, N,N-dimethylacetamide, and N-methylpyrrolidone; halogenated hydrocarbons such as methylene chloride and chloroform; alcohols such as trifluoroethanol; sulfoxides such as dimethyl sulfoxide; amines such as pyridine; ethers such as dioxane and tetrahydrofuran; nitriles such as acetonitrile and propionitrile; esters such as methyl acetate and ethyl acetate; suitable mixtures thereof; and the like. Reaction temperature is appropriately selected from the range that is known to be usable in protein binding reactions, and is normally from the range of about −20° C. to about 50° C. An activated amino acid derivative is normally used from 1.5 to 4 times in excess. When the condensation is insufficient as the result of the test using a ninhydrin reaction, sufficient condensation can be carried out by repeating the condensation reaction without elimination of the protecting group. If the condensation is insufficient even though the condensation reaction is repeated, unreacted amino acids can be acetylated by using acetic anhydride or acetylimidazole.

A protecting method and a protecting group of a functional group that should not been involved in the reaction of raw materials, a method of removing the protecting group, a method of activating a functional group involved in the reaction, and the like can be appropriately selected from among publicly known groups or publicly known means.

As the protecting group for the amino group of the starting material, Z, Boc, tertiary pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc and the like, for example, can be used.

The carboxyl group can be protected by, for example, alkyl esterification (for example, linear, branched or cyclic alkyl esterification with methyl, ethyl, propyl, butyl, tertiary butyl, cyclopentyl, cyclohexyl, cycloheptyl, cyclooctyl, 2-adamantyl, and the like), aralkyl esterification (for example, benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, tertiary butoxycarbonyl hydrazidation, trityl hydrazidation, and the like.

The hydroxyl group of serine can be protected by, for example, esterification or etherification. As the group suitable for this esterification, lower alkanoyl groups such as an acetyl group, aroyl groups such as a benzoyl group, and groups derived from carbonic acid such as benzyloxycarbonyl group, ethoxycarbonyl group and the like, for example, can be used. In addition, as examples of the group suitable for etherification, a benzyl group, a tetrahydropyranyl group, a t-butyl group and the like can be mentioned.

As the protecting group for the phenolic hydroxyl group of tyrosine, Bzl, $C_{12}$-Bzl, 2-nitrobenzyl, Br-Z, tertiary butyl and the like, for example, can be used.

As the protecting group for the imidazole of histidine, Tos, 4-methoxy-2,3,6-trimethylbenzenesulfonyl, DNP, benzyloxymethyl, Bum, Boc, Trt, Fmoc and the like, for example, can be used.

As the method of removing (eliminating) a protecting group, catalytic reduction in a hydrogen stream in the presence of a catalyst such as Pd-black or Pd-carbon; acid treatment by means of anhydrous hydrogen fluoride, methanesulfonic acid, trifluoromethane-sulfonic acid, trifluoroacetic acid, or a mixture solution thereof; base treatment by means of diisopropylethylamine, triethylamine, piperidine, piperazine or the like; and reduction with sodium in liquid ammonia, and the like, for example, can be used. The elimination reaction by the above-described acid treatment is generally carried out at a temperature of about −20° C. to about 40° C.; the acid treatment is efficiently conducted by adding a cation scavenger such as anisole, phenol, thioanisole, m-cresol, p-cresol, dimethyl sulfide, 1,4-butanedithiol or 1,2-ethanedithiol, for example. Also, a 2,4-dinitrophenyl group used as a protecting group for the imidazole of histidine is removed by thiophenol treatment; a formyl group used as a protecting group for the indole of tryptophan is removed by acid treatment in the presence of 1,2-ethanedithiol, 1,4-butanedithiol, or the like, as well as by alkali treatment with a dilute sodium hydroxide solution, dilute ammonia, or the like.

As the raw material having an activated carboxyl group, a corresponding acid anhydride, an azide, an activated ester [an ester with an alcohol (for example, pentachlorophenol, 2,4, 5-trichlorophenol, 2,4-dinitrophenol, cyanomethyl alcohol, p-nitrophenol, HONB, N-hydroxysuccimide, N-hydroxyphthalimide, or HOBt)] and the like, for example, can be used. As the raw material having an activated amino group, a corresponding phosphoric amide, for example, can be used.

In another method of preparing an amide of a protein or the like, for example, the α-carboxyl group of the carboxy-terminal amino acid is first amidated and hence protected, and a peptide (protein) chain is elongated to a desired chain length toward the amino group side, thereafter a protein or the like having the protecting group for the N-terminal α-amino group of the peptide chain only removed and a protein or the like having the protecting group for the C-terminal carboxyl group only removed are prepared, and these proteins or the like are condensed in a mixed solvent described above. For details about the condensation reaction, the same as above applies. After the protected protein or the like obtained by the condensation is purified, all protecting groups can be removed by the above-described method to yield a desired crude protein or the like. By purifying this crude protein or the like using various publicly known means of purification, and freeze-drying the major fraction, a desired amide of the protein or the like can be prepared.

To obtain an ester of the protein or the like, a desired ester of the protein or the like can be prepared by, for example, condensing the α-carboxyl group of the carboxy-terminal amino acid with a desired alcohol to yield an amino acid ester, and then treating the ester in the same manner as with an amide of the protein or the like.

The partial peptide of the present invention or a salt thereof can also be produced by cleaving ABP1 or a salt thereof with an appropriate peptidase.

Furthermore, the ABP1 species of the present invention can also be produced by cultivating a transformant comprising a DNA that encodes ABP1 or a partial peptide thereof, and separating and purifying the ABP1 species from the culture obtained.

As the DNA that encodes the ABP1 of the present invention or a partial peptide thereof, a genomic DNA, a genomic DNA library, a cDNA derived from any cell (for example, splenocyte, nerve cell, glial cell, pancreatic β cell, myelocyte, mesangial cell, Langerhans' cell, epidermal cell, epithelial cell, endothelial cell, fibroblast, fibrocyte, myocyte, adipocyte, immune cell (for example, macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding precursor cell, stem cell or cancer cell thereof, and the like) of a human or another warm-blooded animal (for example, human, mouse, rat, guinea pig, hamster, rabbit, sheep, goat, swine, bovine, horse, bird, cat, dog, monkey, chimpanzee, and the like), a blood cell series cell, or any tissue where such cells are present, for example, brain or any portion of brain (e.g., olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine, small intestine), blood vessel, heart, thymus, spleen, submandibular gland, peripheral blood, peripheral blood cells, prostate, testicle, testis, ovary, placenta, uterus, bone, joint, skeletal muscle, and the like (particularly the brain or any portion of the brain), a cDNA library derived from the aforementioned cell or tissue, synthetic DNA and the like can be mentioned. The vector used for the library may be any of a bacteriophage, a plasmid, a cosmid, a phagemid and the like. The DNA can also be amplified directly by a reverse transcriptase polymerase chain reaction (hereinafter abbreviated as "RT-PCR method") using a total RNA or mRNA fraction prepared from the above-described cell or tissue.

As examples of the DNA that encodes the ABP1 of the present invention, a DNA that comprises the base sequence shown by SEQ ID NO:1 or SEQ ID NO:3, a DNA that comprises a base sequence hybridizing to the base sequence shown by SEQ ID NO:1 or SEQ ID NO:3 under high stringent conditions, and that encodes the aforementioned protein having substantially the same quality of activity (e.g., activity to promote the activation of the ASK1 cascade, activity to induce apoptosis, and the like) as a protein that comprises the amino acid sequence shown by SEQ ID NO:2 or SEQ ID NO:4, and the like can be mentioned.

As the DNA capable of hybridizing to the base sequence shown by SEQ ID NO:1 or SEQ ID NO:3 under high stringent conditions, a DNA that comprises a base sequence having a homology of about 50% or more, preferably about 60% or more, more preferably about 70% or more, particularly preferably about 80% or more, and most preferably about 90% or more, to the base sequence shown by SEQ ID NO:1 or SEQ ID NO:3, and the like, for example, can be used.

Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the attached instruction manual. Hybridization can preferably be conducted under high stringent conditions.

High-stringent conditions refer to, for example, conditions involving a sodium concentration of about 19 to 40 mM, preferably about 19 to 20 mM, and a temperature of about 50 to 70° C., preferably about 60 to 65° C. In particular, a case wherein the sodium concentration is about 19 mM and the temperature is about 65° C. is preferred.

The DNA that encodes the ABP1 of the present invention is preferably an hABP1 DNA that comprises the base sequence shown by SEQ ID NO:1, or an mABP1 DNA that comprises the base sequence shown by SEQ ID NO:3, or a homologue thereof in another warm-blooded animal (for example, rat, guinea pig, hamster, rabbit, sheep, goat, swine, bovine, horse, bird, cat, dog, monkey, chimpanzee and the like).

The DNA that encodes the partial peptide of the present invention may be any one that comprises the base sequence that encodes the same or substantially the same amino acid sequence as a portion of the amino acid sequence shown by SEQ ID NO:2 or SEQ ID NO:4. The DNA may be any of a genomic DNA, a genomic DNA library, a cDNA derived from the above-described cell or tissue, a cDNA library derived from the above-described cell or tissue, and a synthetic DNA. The vector used for the library may be any of a bacteriophage, a plasmid, a cosmid, a phagemid and the like. The DNA can also be amplified directly by the RT-PCR method using an mRNA fraction prepared from the above-described cell or tissue.

Specifically, as the DNA that encodes the partial peptide of the present invention, (1) a DNA having a partial base sequence of a DNA having the base sequence shown by SEQ ID NO:1 or SEQ ID NO:3, (2) a DNA having a base sequence hybridizing to a DNA having the base sequence shown by SEQ ID NO:1 or SEQ ID NO:3 under high stringent conditions, and that encodes a peptide having:
(2a) substantially the same quality of activity (e.g., activity to promote the activation of the ASK1 cascade, activity to induce apoptosis, and the like) as that of a protein that comprises the amino acid sequence encoded by the DNA or
(2b) activity to inhibit the activity of a protein that comprises the amino acid sequence encoded by the DNA (e.g., activity to inhibit the activation of the ASK1 cascade, activity to suppress apoptosis, and the like) and the like, for example, can be used.

As the DNA capable of hybridizing to the base sequence shown by SEQ ID NO:1 or SEQ ID NO:3 under high stringent conditions, a polynucleotide that comprises a base sequence having a homology of about 60% or more, preferably about 70% or more, more preferably about 80% or more, and most preferably about 90% or more, to the corresponding portion in the base sequence, and the like, for example, can be used.

The DNA that encodes the ABP1 of the present invention or a partial peptide thereof can be cloned by amplifying it by the PCR method using a synthetic DNA primer having a portion of the base sequence that encodes the protein or peptide, or by hybridizing DNA incorporated in an appropriate expression vector to a labeled DNA fragment or synthetic DNA that encodes a portion or the entire region of the protein of the present invention. Hybridization can be conducted according to, for example, a method described in Molecular Cloning, 2nd edition (ibidem) and the like. When a commercially available library is used, hybridization can be conducted according to the method described in the instruction manual attached to the library.

The base sequence of DNA can be converted according to a method known per se, such as the ODA-LA PCR method, the Gapped duplex method, the Kunkel method and the like, or a method based thereon, using a publicly known kit, for example, Mutan™-super Express Km (Takara Shuzo Co., Ltd.), Mutan™-K (Takara Shuzo Co., Ltd.) and the like.

The cloned DNA can be used as is, or after digestion with a restriction endonuclease or addition of a linker as desired, depending on the purpose of its use. The DNA may have the translation initiation codon ATG at the 5' end thereof, and the translation stop codon TAA, TGA or TAG at the 3' end thereof. These translation initiation codons and translation stop codons can be added using an appropriate synthetic DNA adapter.

A DNA expression vector encoding the ABP1 of the present invention or a partial peptide thereof can be produced by, for example, cutting out a desired DNA fragment from the DNA encoding the ABP1, and joining the DNA fragment downstream of a promoter in an appropriate expression vector.

Useful expression vectors include plasmids derived from *E. coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); bacteriophages such as λ phage; animal viruses such as retrovirus, vaccinia virus and baculovirus; pA1-11, pXT1, pRc/CMV, pRc/RSV, pcDNAI/Neo and the like.

The promoter may be any promoter, as long as it is appropriate for the host used to express the gene.

For example, when the host is an animal cell, the SRα promoter, the SV40 promoter, the LTR promoter, the CMV (cytomegalovirus) promoter, the HSV-TK promoter and the like are used. Of these, the CMV promoter, the SRa promoter and the like are preferred.

When the host is a bacterium of the genus *Escherichia*, the trp promoter, the lac promoter, the recA promoter, the $\lambda P_L$ promoter, the lpp promoter, the T7 promoter and the like are preferred.

When the host is a bacterium of the genus *Bacillus*, the SPO1 promoter, the SPO2 promoter, the penP promoter and the like are preferred.

When the host is yeast, the PHO5 promoter, the PGK promoter, the GAP promoter, the ADH promoter and the like are preferred.

When the host is an insect cell, the polyhedrin prompter, the P10 promoter and the like are preferred.

Useful expression vectors include, in addition to the above, expression vectors that optionally comprises an enhancer, a splicing signal, a polyA addition signal, a selection marker, an SV40 replication origin (hereinafter also abbreviated as SV40ori), and the like. As examples of the selection markers, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance), and the like can be mentioned. In particular, when a dhfr gene defective Chinese hamster cell is used and the dhfr gene is used as the selection marker, a target gene can also be selected using a thymidine-free medium.

In addition, as required, a signal sequence that matches with the host may be added to the N-terminal of the protein of the present invention. Useful signal sequences include a PhoA signal sequence, an OmpA signal sequence and the like when the host is a bacterium of the genus *Escherichia*; an α-amylase signal sequence, a subtilisin signal sequence and the like when the host is a bacterium of the genus *Bacillus*; an MFα signal sequence, an SUC2 signal sequence and the like when the host is yeast; and an insulin signal sequence, an α-interferon signal sequence, an antibody molecule signal sequence and the like when the host is an animal cell.

A transformant that comprises the thus-obtained "DNA encoding the ABP1 of the present invention or a partial peptide thereof" can be produced by transforming the host with an expression vector that comprises the DNA in accordance with a publicly known method.

Here, as the expression vector, the above-mentioned expression vectors can be mentioned.

As useful examples of the host, a bacterium of the genus *Escherichia*, a bacterium of the genus *Bacillus*, yeast, an insect cell, an insect, an animal cell, and the like can be mentioned.

As useful examples of the bacterium of the genus *Escherichia, Escherichia coli* K12 DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), HB101 (Journal of Molecular Biology, Vol. 41, 459 (1969)), C600 (Genetics, Vol. 39, 440 (1954)), and the like can be mentioned.

As useful examples of the bacterium of the genus *Bacillus, Bacillus subtilis* MI114 (Gene, Vol. 24, 255 (1983)), 207-21 (Journal of Biochemistry, Vol. 95, 87 (1984)) and the like can be mentioned.

As useful examples of the yeast, *Saccharomyces cerevisiae* AH22, AH22R$^-$, NA87-11A, DKD-5D and 20B-12, *Schizosaccharomyces pombe* NCYC1913 and NCYC2036, *Pichia pastoris* KM71 and the like can be mentioned.

As useful examples of the insect cell, *Spodoptera frugiperda* cell (Sf cell), MG1 cell derived from the mid-intestine of *Trichoplusia ni*, High Five™ cell derived from an egg of *Trichoplusia ni*, cell derived from *Mamestra brassicae*, cell derived from *Estigmena acrea*, and the like can be mentioned when the virus is AcNPV. When the virus is BMNPV, useful insect cells include *Bombyx mori* N cell (BmN cell) and the like. As useful examples of the Sf cell, Sf9 cell (ATCC CRL1711), Sf21 cell (both in Vaughn, J. L. et al., In Vivo, 13, 213-217 (1977), and the like can be mentioned.

As useful examples of the insect, a larva of *Bombyx mori* (Maeda et al., Nature, Vol. 315, 592 (1985)), and the like can be mentioned.

As useful examples of the animal cell, monkey cell COS-7, Vero, Chinese hamster cell CHO (hereafter abbreviated as CHO cell), dhfr gene defective Chinese hamster cell CHO (hereafter abbreviated as CHO (dhfr$^-$) cell), mouse L cell, mouse AtT-20, mouse myeloma cell, rat GH3, human FL cell and the like can be mentioned.

Transformation can be carried out according to the kind of host in accordance with a publicly known method.

A bacterium of the genus *Escherichia* can be transformed, for example, in accordance with a method described in Proc. Natl. Acad. Sci. U.S.A., Vol. 69, 2110 (1972), Gene, Vol. 17, 107 (1982), and the like.

A bacterium of the genus *Bacillus* can be transformed, for example, according to a method described in Molecular and General Genetics, Vol. 168, 111 (1979), and the like.

Yeast can be transformed, for example, in accordance with a method described in Methods in Enzymology, Vol. 194, 182-187 (1991), Proc. Natl. Acad. Sci. USA, Vol. 75, 1929 (1978), and the like.

An insect cell and an insect can be transformed, for example, according to a method described in Bio/Technology, 6, 47-55 (1988), and the like.

An animal cell can be transformed, for example, in accordance with a method described in Saibo Kogaku, extra issue 8, Shin Saibo Kogaku Jikken Protocol, 263-267 (1995), published by Shujunsha, or Virology, Vol. 52, 456 (1973).

Cultivation of a transformant can be carried out according to the kind of host in accordance with a publicly known method.

For example, when a transformant whose host is a bacterium of the genus *Escherichia* or the genus *Bacillus* is cultivated, the culture medium is preferably a liquid medium. Also, the medium preferably comprises a carbon source, a nitrogen source, an inorganic substance, and the like, necessary for the growth of the transformant. Here, as examples of the carbon source, glucose, dextrin, soluble starch, sucrose, and the like can be mentioned; as examples of the nitrogen source, inorganic and organic substances such as an ammonium salt, a nitrate salt, corn steep liquor, peptone, casein, meat extract, soybean cake, potato extract, and the like can be mentioned; as examples of the inorganic substance, calcium chloride, sodium dihydrogen phosphate, magnesium chloride, and the like can be mentioned. In addition, the medium may be supplemented with yeast extract, vitamins, growth promoting factor, and the like. Preferably, the pH of the medium is about 5 to about 8.

Examples of the medium used to cultivate a transformant whose host is a bacterium of the genus *Escherichia* include a M9 medium supplemented with glucose and a Casamino acid (Miller, Journal of Experiments in Molecular Genetics, 431-433, Cold Spring Harbor Laboratory, New York, 1972). As required, in order to increase promoter efficiency, a chemical such as 3β-indolylacrylic acid may be added to the medium.

Cultivation of a transformant whose host is a bacterium of the genus *Escherichia* is normally carried out at about 15° C. to about 43° C. for about 3 to about 24 hours. As necessary, the culture may be aerated or agitated.

Cultivation of a transformant whose host is a bacterium of the genus *Bacillus* is normally carried out at about 30° C. to about 40° C. for about 6 to about 24 hours. As necessary, the culture may be aerated or agitated.

As examples of the medium for cultivating a transformant whose host is a yeast, Burkholder's minimum medium [Bostian, K. L. et al., Proc. Natl. Acad. Sci. USA, vol. 77, 4505 (1980)] and SD medium supplemented with 0.5% casamino acid [Bitter, G. A. et al., Proc. Natl. Acad. Sci. USA, vol. 81, 5330 (1984)] can be mentioned. The medium's pH is preferably about 5 to 8. Cultivation is normally carried out at about 20° C. to about 35° C. for about 24 to about 72 hours. As necessary, the culture may be aerated or agitated.

Useful medium for cultivating a transformant whose host is an insect cell or an insect include, for example, Grace's insect medium [Grace, T. C. C., Nature, 195, 788 (1962)] supplemented with additives such as inactivated 10% bovine serum as appropriate. The medium's pH is preferably about 6.2 to 6.4. Cultivation is normally carried out at about 27° C. for about 3 to 5 days. As necessary, the culture may be aerated or agitated.

Useful medium for cultivating a transformant whose host is an animal cell include, for example, MEM medium supplemented with about 5 to 20% fetal bovine serum [Science, Vol. 122, 501(1952)], DMEM medium [Virology, Vol. 8, 396(1959)], RPMI 1640 medium [The Journal of the American Medical Association, Vol. 199, 519(1967)], 199 medium [Proceeding of the Society for the Biological Medicine, Vol. 73, 1(1950)] and the like. The medium's pH is preferably about 6 to 8. Cultivation is normally carried out at about 30° C. to 40° C. for about 15 to 60 hours. As necessary, the culture may be aerated or agitated.

As described above, the ABP1 of the present invention or a partial peptide thereof or a salt thereof (an ABP1 species) can be produced in or outside the cells of the transformant.

The ABP1 species of the present invention can be separated and purified from the culture obtained by cultivating the aforementioned transformant according to a method known per se.

For example, when the ABP1 species of the present invention is extracted from cultivated bacteria or cells, a method is used as appropriate wherein the bacteria or cells are recovered by a known means, suspended in an appropriate buffer solution, and disrupted by means of sonication, lysozyme and/or freeze-thawing and the like, after which a crude extract of soluble protein is obtained by centrifugation or filtration. The buffer solution may contain a protein denaturant such as urea or guanidine hydrochloride and a surfactant such as Triton X-100™.

Isolation and purification of the ABP1 species of the present invention contained in the thus-obtained soluble fraction can be conducted according to a method known per se. Useful methods include methods based on solubility, such as salting-out and solvent precipitation; methods based mainly on molecular weight differences, such as dialysis, ultrafiltration, gel filtration, and SDS-polyacrylamide gel electrophoresis; methods based on charge differences, such as ion exchange chromatography; methods based on specific affinity, such as affinity chromatography; methods based on hydrophobic ity differences, such as reversed-phase high performance liquid chromatography; and methods based on isoelectric point differences, such as isoelectric focusing. These methods can be combined as appropriate.

When the thus-obtained ABP1 species is a free form, the free form can be converted to a salt by a method known per se or a method based thereon; when the ABP1 species is obtained as a salt, the salt can be converted to a free form or another salt by a method known per se or a method based thereon.

Note that the ABP1 species produced by the transformant can also be optionally modified by the action of an appropriate protein-modifying enzyme, before or after purification, or can have a polypeptide thereof removed partially. As such, useful protein-modifying enzymes include, for example, trypsin, chymotrypsin, arginyl endopeptidase, protein kinase, glycosidase and the like.

The presence of the thus-obtained ABP1 species of the present invention can be confirmed by enzyme immunoassay, Western blotting and the like employing a specific antibody.

Furthermore, the ABP1 species of the present invention can also be synthesized by in vitro translation using a cell-free protein translation system that comprises a rabbit reticulocyte lysate, wheat germ lysate, *Escherichia coli* lysate and the like, with RNA corresponding to the above-described DNA that encodes ABP1 or a partial peptide thereof as the template. Alternatively, the ABP1 species of the present invention can be synthesized using a cell-free transcription/translation system containing RNA polymerase, with the DNA that encodes the ABP1 or a partial peptide thereof as the template.

The antibody against the ABP1 of the present invention or a salt thereof (hereinafter also abbreviated as "the antibody of the present invention") may be any of a polyclonal antibody and a monoclonal antibody, as long as it is capable of recognizing ABP1 or a salt thereof. The antibody against ABP1 or a salt thereof can be produced according to a method of antibody or antiserum production known per se using the ABP1 species of the present invention as an antigen. The ABP1 species of the present invention used as the antigen may be any one, as long as it is the above-described ABP1 or a partial peptide thereof or a salt thereof.

A monoclonal antibody or polyclonal antibody against ABP1 or a salt thereof can, for example, be produced as described below.

[Preparation of Monoclonal Antibody]

(a) Preparation of Monoclonal Antibody-producing Cells

The ABP1 species of the present invention, as is or along with a carrier or a diluent, is administered to a mammal at a site permitting antibody production by administration. To increase antibody productivity in this administration, complete Freund's adjuvant and incomplete Freund's adjuvant may be administered. The administration is normally conducted every 2 to 6 weeks, in a total of about 2 to 10 times. As examples of the mammal used, monkey, rabbit, dog, guinea pig, mouse, rat, sheep, and goat can be mentioned, and a mouse and a rat are preferably used.

For example, a monoclonal antibody-producing hybridoma can be prepared by selecting an individual with an antibody titer from among antigen-immunized mammals, for example, mice, recovering the spleen or a lymph node 2-5 days after final immunization, and fusing an antibody-producing cell contained therein with an allogeneic or heterogeneous myeloma cell. A measurement of antibody titer in the antiserum can be conducted by, for example, reacting the labeled protein described below and an antiserum, and thereafter measuring the activity of the labeling agent bound to the antibody. The fusion procedure can be performed according to a known method, for example, the method of Köhler and Milstein [Nature, 256, 495 (1975)]. As examples of a fusogen, polyethylene glycol (PEG), Sendai virus and the like can be mentioned, and PEG is preferably used.

As examples of the myeloma cell, mammalian myeloma cells such as NS-1, P3U1, SP2/O and AP-1 can be mentioned, and P3U1 is preferably used. A preferable ratio of the number of antibody-producing cells (splenocytes) and number of myeloma cells used is about 1:1 to 20:1; cell fusion can be efficiently performed by adding a PEG (preferably PEG1000 to PEG6000) at concentrations of about 10 to 80%, and conducting incubation at 20 to 40° C., preferably at 30 to 37° C., for 1 to 10 minutes.

A monoclonal antibody-producing hybridoma can be screened for by, for example, a method wherein the hybridoma culture supernatant is added to a solid phase (e.g., microplate) having an antigen adsorbed thereto directly or along with a carrier, an anti-immunoglobulin antibody (when the cell used for cell fusion is a mouse cell, an anti-mouse immunoglobulin antibody is used) or protein A labeled with a radioactive substance, an enzyme or the like is then added, and the monoclonal antibody bound to the solid phase is detected, a method wherein the hybridoma culture supernatant is added to a solid phase having an anti-immunoglobulin antibody or protein A adsorbed thereto, a protein labeled with a radioactive substance, an enzyme or the like is added, and the monoclonal antibody bound to the solid phase is detected, and the like.

Selection of a monoclonal antibody can be conducted according to a method known per se or a method based thereon. Selection of a monoclonal antibody can normally be conducted using an animal cell culture medium supplemented with HAT (hypoxanthine, aminopterin, thymidine). As the medium for selection and breeding of a monoclonal antibody, any medium can be used, as long as the hybridoma can grow therein. For example, an RPMI 1640 medium containing 1 to 20%, preferably 10 to 20%, fetal bovine serum, a GIT medium (Wako Pure Chemical Industries, Ltd.) containing 1 to 10% fetal bovine serum or a serum-free medium for hybridoma culture (SFM-101, Nissui Pharmaceutical Co., Ltd.) and the like can be used. Cultivation temperature is normally 20 to 40° C., preferably about 37° C. Cultivation time is normally 5 days to 3 weeks, preferably 1 week to 2 weeks. Cultivation can normally be conducted under 5% carbonic acid gas. The antibody titer of the hybridoma culture supernatant can be measured in the same manner as the above-described measurement of the antibody titer in the antiserum.

The thus-obtained monoclonal antibody can be separated and purified according to a method known per se, for example, a method of immunoglobulin separation and purification [e.g., salting-out method, alcohol precipitation method, isoelectric point precipitation method, electrophoresis method, adsorption and desorption method using an ion exchanger (e.g., DEAE), ultracentrifugation method, gel filtration method, specific purification method wherein only the antibody is recovered using an antigen-binding solid phase or an active adsorbent such as protein A or protein G, and its binding is dissociated to yield the antibody].

[Preparation of Polyclonal Antibody]

A polyclonal antibody against ABP1 or a salt thereof can be produced according to a method known per se. For example, the polyclonal antibody can be produced by immunizing a mammal with an immunogen (ABP1 species) as is or a complex thereof with a carrier protein in the same manner as the above-described method of monoclonal antibody production, recovering the antibody-containing product of the present invention from the immunized animal, and separating and purifying the antibody. In addition to mammals, a chicken and the like can also be used.

Regarding the complex of an immunogen and carrier protein used to immunize a mammal, any kind of carrier protein can be crosslinked at any mixing ratio of carrier and hapten, as long as an antibody against the carrier-crosslinked immunized hapten is efficiently produced; for example, a method wherein bovine serum albumin, bovine thyroglobulin, hemocyanin or the like is coupled at a ratio of about 0.1 to 20, preferably about 1 to 5, parts by weight per 1 part by weight of hapten, can be used.

For coupling of a hapten and a carrier, various condensing agents, for example, active ester reagents containing glutaraldehyde, carbodiimide, a maleimide active ester, a thiol group or a dithiopyridyl group, and the like can be used.

The condensation product, as is or along with a carrier or a diluent, is administered to a mammal at a site permitting antibody production. To increase antibody productivity in this administration, complete Freund's adjuvant and incomplete Freund's adjuvant may be administered. The administration is normally conducted every 2 to 6 weeks, in a total of about 3 to 10 times.

A polyclonal antibody can be recovered from blood, ascites fluid and the like, preferably blood, of a mammal immunized by the above-described method.

A measurement of the polyclonal antibody titer in the antiserum can be conducted in the same manner as the above-described measurement of antibody titer in the antiserum. Separation and purification of the polyclonal antibody can be conducted according to the same immunoglobulin separation and purification method as the above-described monoclonal antibody separation and purification.

When a partial peptide of ABP1 is used as an antigen, its position on ABP1 is not subject to limitation; for example, an oligopeptide having a partial amino acid sequence of a region conserved well between various warm-blooded animals can be mentioned. Specifically, a peptide having the amino acid sequence shown by SEQ ID NO:5 or SEQ ID NO:6, conserved completely between the human and the mouse, and the like can be entioned as a preferable example.

As the polynucleotide comprising a base sequence complementary to the base sequence that encodes the ABP1 of the present invention or a part thereof (hereinafter also abbreviated as "the antisense polynucleotide of the present invention"), any polynucleotide can be mentioned, as long as it has a base sequence completely complementary or substantially complementary to the base sequence that encodes the ABP1, or a part thereof, and acts to suppress the translation of the protein from the RNA that encodes the ABP1. As the "substantially complementary base sequence", a base sequence capable of hybridizing to the base sequence that encodes the ABP1 or a partial peptide thereof under the physiological conditions for the cell that expresses the protein, more specifically, a base sequence having a homology of about 70% or more, preferably about 80% or more, more preferably about 90% or more, and most preferably about 95% or more, to the complementary strand of the base sequence that encodes the ABP1 or a partial peptide thereof, and the like can be mentioned.

The antisense polynucleotide of the present invention can be designed and synthesized on the basis of information on the cloned or determined base sequence of the polynucleotide of the present invention. Such a polynucleotide is capable of inhibiting the replication or expression of the gene that encodes ABP1. Hence, the antisense polynucleotide of the present invention is capable of hybridizing to the RNA transcribed from the gene that encodes ABP1, and capable of inhibiting the synthesis (processing) or function (translation into protein) of mRNA.

The target region of the antisense polynucleotide of the present invention is not subject to limitation as to the length thereof, as long as hybridization of the antisense polynucleotide results in the inhibition of the translation of ABP1, and can be the entire sequence or a partial sequence of the RNA that encodes ABP1; a partial sequence of about 15 bases for the shortest, and the entire sequence of the mRNA or initial transcription product for the longest, can be mentioned. Considering the ease of synthesis and the issue of antigenicity, an oligonucleotide consisting of about 15 to about 30 bases is preferred, which, however, is not to be construed as limiting. Specifically, although the 5'-end hairpin loop, the 5'-end 6-base-pair repeat, the 5'-end untranslated region, the polypeptide translation initiation codon, the protein-coding region, the ORF translation initiation codon, the 3'-end untranslated region, the 3'-end palindrome region, and the 3'-end hairpin loop of the gene that encodes ABP1 can be selected as the target region, any region within the gene can be selected as the target. For example, it is also preferable that the intron portion of the gene be the target region.

Furthermore, an antisense polynucleotide of the present invention may be capable of not only hybridizing to the mRNA or the initial transcription product that encodes ABP1 to inhibit the translation to protein, but also binding to an ABP1-encoding gene that is a double-stranded DNA to form a triple strand (triplex) and inhibit the transcription of RNA.

As the antisense polynucleotide, a deoxyribonucleotide containing 2-deoxy-D-ribose, a ribonucleotide containing D-ribose, another type of nucleotide that is an N-glycoside of the purine or pyrimidine base, or another polymer having a non-nucleotide backbone (for example, commercially available protein nucleic acids and synthetic sequence specific nucleic acid polymers) or another polymer having a special bond (however, this polymer contains a nucleotide having a configuration that allows base pairing or base attachment as found in DNA and RNA) and the like can be mentioned. These may be double-stranded DNAs, single-stranded DNAs, double-stranded RNAs or single-stranded RNAs, or DNA:RNA hybrids, and may also be non-modified polynucleotides (or non-modified oligonucleotides), those having a known modification added thereto, for example, those with a label known in the relevant field, those with a cap, those methylated, those having 1 or more naturally occurring nucleotides substituted by analogues, those modified with an intramolecular nucleotide, for example, those having a non-charge bond (for example, methylphosphonate, phospho triester, phosphoramidate, carbamate and the like), those having a charged bond or a sulfur-containing bond (for example, phosphorothioate, phosphorodithioate and the like), for example, those having a side chain group of a protein (nuclease, nuclease inhibitor, toxin, antibody, signal peptide, poly-L-lysine and the like), a sugar (for example, monosaccharide and the like) and the like, those having an intercalating compound (for example, acridine, psoralen and the like), those containing a chelate compound (for example, metals, radioactive metals, boron, oxidizing metals and the like), or those containing an alkylating agent, those having a modified bond (for example, α anomer type nucleic acid and the like). Here, "nucleoside", "nucleotide" and "nucleic acid" may include not only those containing the purine and pyrimidine bases, but also those containing another modified heterocycle type base. These modified products may contain a methylated purine and pyrimidine, an acylated purine and pyrimidine, or another heterocycle. The modified nucleotide and the modified nucleotide may also have their sugar portion modified by, for example, substitution of 1 or more hydroxyl groups by a halogen, an aliphatic group and the like, or conversion to a functional group such as an ether or an amine.

The antisense polynucleotide is RNA, DNA, or modified nucleic acid (RNA, DNA). As specific examples of the modified nucleic acid, sulfur derivatives and thiophosphate derivatives of nucleic acids, and those resistant to the decomposition like polynucleosideamide or oligonucleosideamide can be mentioned, which, however, are not to be construed as limiting. The antisense polynucleotide of the present invention can preferably be designed to accomplish one of the following purposes: to make the antisense polynucleotide more stable in the cell, to increase the cell permeability of the antisense polynucleotide, to increase the affinity for the desired sense strand, and to reduce the toxicity, if any, of the antisense polynucleotide. Many such modifications are known in the relevant field, and are disclosed in, for example, J. Kawakami et al., Pharm Tech Japan, Vol. 8, pp. 247, 1992; Vol. 8, pp. 395, 1992; S. T. Crooke et al. ed., Antisense Research and Applications, CRC Press, 1993 and the like.

The antisense polynucleotide may be altered, or may contain an modified sugar, base or bond, and can be supplied in a special form like liposome or microspheres, can be applied for gene therapy, and can be given in an adduct form. As such an adduct form used, a polycation derivative like polylysine, which acts to neutralize the charge of the phosphate backbone, and a hydrophobic one like a lipid that enhances the interaction with cell membrane or increases nucleic acid uptake (for example, phospholipid, cholesterol and the like) can be mentioned. As lipids preferred for addition, cholesterol and derivatives thereof (for example, cholesterylchloroformate, cholic acid and the like) can be mentioned. These can be attached to the 3' end or the 5' end of nucleic acid, and can be attached via a base, a sugar or an intramolecular nucleoside bond. As other groups, a capping group specifically arranged at the 3' end or 5' end of nucleic acid to prevent degradation by a nuclease such as exonuclease or RNase can be mentioned. As such a capping group, hydroxyl group protecting groups known in the relevant field, including glycols such as polyethylene glycol and tetraethylene glycol, can be mentioned, which, however, are not to be construed as limiting.

A ribozyme capable of specifically cleaving the mRNA or the initial transcription product that encodes ABP1 within the coding region (including the intron portion in the case of the initial transcription product) can also be encompassed in the antisense polynucleotide of the present invention. "Ribozyme" refers to RNA possessing an enzyme activity to cleave a nucleic acid, and is herein understood to be used as a concept encompassing DNA, as long as sequence-specific nucleic acid cleavage activity is possessed, since it has recently been found that oligo DNA having the base sequence of the enzyme activity portion also possesses nucleic acid cleavage activity. One of the most versatile ribozymes is self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends adjoining to the hammerhead structure portion (about 10 bases in total) to be a sequence complementary to the desired cleavage site of the mRNA. Because this type of ribozymes has RNA only as the substrate, they offer an additional advantage of non-attack of genomic DNA. Provided that the mRNA that encodes ABP1 takes a double-stranded structure by itself, the target sequence can be made single-stranded, using a hybrid ribozyme prepared by joining an RNA motif derived from a viral nucleic acid that can specifically bind to RNA helicase [Proc. Natl. Acad. Sci. USA, 98(10): 5572-5577 (2001)]. Furthermore, when the ribozyme is used in the form of an expression vector containing the DNA that encodes it, the ribozyme may be a hybrid ribozyme prepared by further joining a sequence modified from the tRNA to promote the migration of the transcription product to cytoplasm [Nucleic Acids Res., 29(13): 2780-2788 (2001)].

A double-stranded oligo RNA complementary to a partial sequence (including the intron portion in the case of the initial transcription product) within the coding region of the mRNA or the initial transcription product that encodes ABP1 (small interfering RNA; siRNA) can also be encompassed in the antisense polynucleotide of the present invention. RNA interference (RNAi), a phenomenon in which introducing short double-stranded RNA in cells leads to the decomposition of mRNA complementary to the RNA, has been known to occur in nematodes, insects, plants and the like, and since this phenomenon has recently been found to occur in mammalian cells as well [Nature, 411(6836): 494-498 (2001)], it is attracting attention for technology to replace ribozyme.

The antisense oligonucleotide and ribozyme of the present invention can be prepared by determining the target region of the mRNA or initial transcription product on the basis of information on the cDNA sequence or genomic DNA sequence that encodes the protein of the present invention, and synthesizing a sequence complementary thereto using a commercially available DNA/RNA synthesizer (Applied Biosystems, Beckman Instruments, and the like). siRNA can be prepared by synthesizing each of a sense strand and an antisense strand using a DNA/RNA synthesizer, denaturing the strands in an appropriate annealing buffer solution at, for example, about 90 to about 95° C. for about 1 minute, and then annealing the strands at about 30 to about 70° C. for about 1 to about 8 hours. It is also possible to prepare a longer double-stranded polynucleotide by synthesizing complementary oligonucleotide strands in alternative overlaps, annealing the strands, and ligating the strands using ligase.

Because ABP1 or the activating peptide of the present invention binds to ASK1 to activate the same, it is capable of promoting apoptosis induction via the ASK1 kinase cascade. Therefore, (i) ABP1 or the activating peptide of the present invention, (ii) a polynucleotide that encodes ABP1 or the activating peptide of the present invention, (iii) a polynucleotide that comprises the base sequence that encodes ABP1 or a portion thereof, (iv) the antibody of the present invention, (v) the antisense polynucleotide of the present invention, and (iv) the inhibitory peptide of the present invention have the uses shown below.

(1) An Agent for Promoting ASK1 Activation and an Agent for Inducing Apoptosis

ABP1 acts to promote apoptosis induction via the ASK1 kinase cascade by binding to ASK1 to activate the same. Therefore, it is possible to promote the activation of the intracellular ASK1 or to induce apoptosis to the cell, by adding ABP1 or the activating peptide of the present invention or a salt thereof to the cell, or by introducing a polynucleotide that encodes the ABP1 or the activating peptide of the present invention to the cell and allowing its expression to increase the ABP1 content in the cell, and ABP1 can be used as, for example, a reagent for apoptosis research.

When an ABP1 or the activated peptide of the present invention or a salt thereof is used as the above-described agent for promoting ASK1 activation or an agent for inducing apoptosis, it can be prepared by being dissolved in water or an appropriate buffer solution (e.g., phosphate buffer solution, PBS, Tris-HCl buffer solution and the like) to obtain an appropriate concentration. Also, as required, a commonly used preservative, stabilizer, reducing agent, isotonizing agent and the like may be formulated.

On the other hand, when a polynucleotide that encodes ABP1 or the activating peptide of the present invention is used as the above-described agent for promoting ASK1 activation or the agent for inducing apoptosis, the polynucleotide alone, or after insertion to an appropriate vector such as the retrovirus vector, the adenovirus vector or the adenovirus-associated virus vector, can be introduced to cells using the above-described method of transformation (e.g., liposome method, electroporation method and the like).

(2) Prophylactic or Therapeutic Agent for Disease Associated with Apoptosis Suppression As described above, because ABP1 has the function of activating ASK1 to induce apoptosis to cells, various diseases, for example, cancers, autoimmune diseases, viral infections, endocrine diseases, hematological diseases, and organ hyperplasia develop, if ABP1 or a nucleic acid that encodes the same (e.g., gene, mRNA and the like) is abnormal or lacked in the body, or if the expression level thereof is abnormally decreased, and if cell apoptosis induction is suppressed in excess by any other factor.

Therefore, for a patient not expected to have the removal of unwanted cells and abnormal cells by apoptosis due to a reduction in ABP1 or any other factor, it is possible to increase the ABP1 content in the patient's body and induce apoptosis via the ASK1 cascade in the abnormal cells and unwanted cells by a) administering ABP1 or the activating peptide of the present invention or a salt thereof to the patient to supplement the ABP1 content, or by b) (i) administering a DNA that encodes ABP1 or the activating peptide of the present invention to the patient to allow its expression in the target cell, or (ii) introducing a DNA that encodes ABP1 or the activating peptide of the present invention to the isolated target cell to allow its expression, and transplanting the cell to the patient.

Accordingly, a) ABP1 or the activating peptide of the present invention or a salt thereof, or b) a polynucleotide that encodes ABP1 or the activating peptide of the present invention can be used as a prophylactic or therapeutic agent for a disease in which induction of apoptosis is effective for the prophylaxis or therapy thereof, for example cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like), post-angioplastic restenosis, recurrence after cancer resection, and the like.

When ABP1 or the activating peptide of the present invention or a salt thereof is used as the above-described prophylactic or therapeutic agent, it can be formulated by a conventional means.

On the other hand, when a polynucleotide that encodes ABP1 or the activating peptide of the present invention is used as the above-described prophylactic or therapeutic agent, the polynucleotide alone, or after insertion to an appropriate vector such as the retrovirus vector, the adenovirus vector or the adenovirus-associated virus vector, can be formulated according to a conventional method. The polynucleotide, as is or along with an auxiliary agent for promotion of intake thereof, can be administered using a gene gun or a catheter like a hydrogel catheter.

For example, a) ABP1 or the activating peptide of the present invention or a salt thereof, or b) a polynucleotide that encodes ABP1 or the activating peptide of the present invention can be used orally as tablets, capsules, elixirs, microcapsules and the like, coated with sugar as required, or can be used non-orally in the form of an injection such as a sterile solution or suspension in water or another pharmaceutically acceptable liquid. For example, by blending a) ABP1 or the activating peptide of the present invention or a salt thereof, or b) a polynucleotide that encodes ABP1 or the activating peptide of the present invention, along with a known physiologically acceptable carrier, a sweetener, a excipient, a vehicle, an antiseptic, a stabilizer, a binder and the like, in a unit dosage form required for generally accepted preparation design, such a preparation can be produced. The active ingredient contents in these preparations are intended to ensure that an appropriate dose in the specified range is obtained.

As examples of additives that can be formulated in tablets, capsules and the like, a binder like gelatin, cornstarch, tragacanth and gum arabic, a excipient like crystalline cellulose, a swelling agent like cornstarch, gelatin, alginic acid and the like, a lubricant like magnesium stearate, a sweetener like sucrose, lactose or saccharin, a flavoring agent like peppermint, acamono oil or cherry and the like can be used. When the formulation unit form is a capsule, the above-described type of material can further contain a liquid carrier like an oil or fat. A sterile composition for injection can be formulated according to an ordinary preparation design such as dissolving or suspending an active substance, a naturally produced vegetable oil such as sesame oil or coconut oil, and the like in a vehicle like water for injection. As examples of aqueous solutions for injection, physiological saline, an isotonic solution containing glucose or other auxiliary agent (for example, D-sorbitol, D-mannitol, sodium chloride and the like) and the like can be used, which may be used in combination with an appropriate solubilizer, for example, an alcohol (e.g., ethanol), a polyalcohol (e.g., propylene glycol, polyethylene glycol), a non-ionic surfactant (e.g., polysorbate 80™, HCO-50) and the like. As examples of oily solutions, sesame oil, soybean oil and the like can be used, which may be used in combination with solubilizers benzyl benzoate, benzyl alcohol and the like.

Also, the above-described prophylactic or therapeutic agent may be formulated with, for example, a buffering agent (for example, phosphate buffer solution, sodium acetate buffer solution), a soothing agent (for example, benzalkonium chloride, procaine hydrochloride and the like), a stabilizer (for example, human serum albumin, polyethylene glycol and the like), a preservative (for example, benzyl alcohol, phenol and the like), an antioxidant and the like. The prepared injection solution is normally filled in an appropriate ampoule.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of ABP1 or the activating peptide of the present invention varies depending on subject of administration, target organ, symptoms, method of administration and the like; in a cancer patient (body weight 60 kg), for example, the usual oral dosage is about 0.1 mg to 100 mg, preferably about 1.0 to 50 mg, more preferably about 1.0 to 20 mg, per day, In the case of non-oral administration, the dosage per administration varies depending on subject of administration, target organ, symptoms, method of administration and the like; in a cancer patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

The dosage of the polynucleotide that encodes ABP1 or the activating peptide of the present invention varies depending on subject of administration, target organ, symptoms, method of administration and the like; in a cancer patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a cancer patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

(2) Genetic Diagnostic Reagent

Because a polynucleotide that comprises the base sequence that encodes ABP1 or a portion thereof (hereinafter referred to as "the sense polynucleotide of the present invention") and the antisense polynucleotide of the present invention is capable of detecting an abnormality (genetic abnormality) in the DNA or mRNA that encodes ABP1 in a human or another warm-blooded animal (for example, rat, mouse, hamster, rabbit, sheep, goat, swine, bovine, horse, cat, dog, monkey, chimpanzee, bird, and the like) when used as a probe, it is useful as, for example, a genetic diagnostic reagent for damage or mutation of the DNA, a splicing abnormality or decreased expression of mRNA, amplification of the DNA, overexpression of mRNA, and the like. A polynucleotide that comprises a portion of the base sequence that encodes ABP1 is not subject to limitation, as long as it has a necessary length for a probe (for example, about 15 bases or more), and needs not encode a partial peptide of ABP1 (i.e., being in frame).

The above-described genetic diagnosis using the sense or antisense polynucleotide of the present invention can be performed by, for example, Northern hybridization, quantitative RT-PCR, PCR-SSCP method, allele-specific PCR, PCR-SSOP method, DGGE method, RNase protection method, PCR-RFLP method and the like which are known per se.

For example, if a reduction in ABP1 expression is detected as a result of Northern hybridization or quantitative RT-PCR of an RNA fraction extracted from cells of a test warm-blooded animal, or if a mutation in the ABP1 gene is detected as a result of an analysis of an RNA fraction or genomic DNA fraction by the PCR-SSCP method, the animal can be diagnosed as suffering from or being likely to suffer from a disease associated with suppression of apoptosis or inflammatory cytokine production, for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like), post-angioplastic restenosis, recurrence after cancer resection and the like.

On the other hand, if ABP1 overexpression is detected by Northern hybridization or quantitative RT-PCR, the animal can be diagnosed as suffering from or being likely to suffer from a disease associated with apoptosis promotion or inflammation, for example, viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

(3) Diagnostic Method using the Antibody of the Present Invention

Because the antibody of the present invention is capable of specifically recognizing ABP1, it can be used to detect ABP1 in a test solution.

Accordingly, the present invention provides:

(i) a method of quantifying an ABP1 or a salt thereof in a test solution, which comprises competitively reacting the antibody of the present invention, the test solution and a labeled ABP1, and determining the ratio of labeled ABP1 bound to the antibody, and (ii) a method of quantifying an ABP1 or a salt thereof in a test solution, which comprises reacting the test solution and the antibody of the present invention insolubilized on a carrier and another antibody of the present invention labeled, simultaneously or serially, and then determining the amount (activity) of the label on the insolubilizing carrier.

In the quantitation method (ii) above, the two kinds of antibodies desirably recognize different portions of ABP1. For example, if one of the two antibodies is an antibody that recognizes an N-terminal portion of ABP1 (e.g., a portion having the amino acid sequence shown by SEQ ID NO:5 and the like), the other antibody can be an antibody that reacts with a C-terminal portion of ABP1 (e.g., a portion having the amino acid sequence shown by SEQ ID NO:6 and the like).

In addition to the quantitation of ABP1 using a monoclonal antibody against ABP1, detection by tissue staining and the like can also be conducted. For these purposes, the antibody molecule itself may be used, and the F(ab')$_2$, Fab' or Fab fraction of the antibody molecule may also be used.

The quantitation of ABP1 or a salt thereof using the antibody of the present invention is not subject to limitation, and any method of measurement can be used, as long as it is a measurement method wherein the amount of antibody, antigen or antibody-antigen complex corresponding to the amount of antigen (for example, ABP1 content) in the test solution is detected by a chemical or physical means and is applied to a standard curve generated using standard solutions containing known amounts of antigen. For example, nephelometry, the competitive method, the immunometric method and the sandwich method are preferably used; it is particularly preferable, in terms of sensitivity and specificity, to use the sandwich method described below.

As examples of the labeling agent used for the assay using a labeled substance, a radioisotope, an enzyme, a fluorescent substance, a luminescent substance and the like can be used. As examples of the radioisotope, [$^{125}$I], [$^{131}$I], [$^{3}$H], [$^{14}$C] and the like can be used. As the enzyme, those that are stable and high in specific activity are preferred; for example, β-galactosidase, β-glucosidase, alkaline phosphatase, peroxidase, malate dehydrogenase and the like can be used. As examples of the fluorescent substance, fluorescamine, fluorescein isothiocyanate and the like can be used. As examples of the luminescent substance, luminol, luminol derivative, luciferin, lucigenin and the like can be used. Furthermore, a biotin-(strepto)avidin system can also be used for binding of an antibody or an antigen and a labeling agent.

In insolubilizing the antigen or antibody, physical adsorption may be used, and a chemical bond in common use to insolubilize or immobilize a protein or an enzyme or the like, may also be used. As the carrier, insoluble polysaccharides such as agarose, dextran and cellulose, synthetic resins such as polystyrene, polyacrylamide and silicone, glass and the like can be mentioned.

In the sandwich method, the amount of ABP1 in a test solution can be quantified by reacting the test solution to an antibody of the present invention insolubilized (primary reaction) and further reacting to another antibody of the present invention labeled (secondary reaction), and thereafter measuring the (amount) activity of the labeling agent on the insolubilizing carrier. The primary reaction and the secondary reaction may be conducted in the reverse order, and may be conducted simultaneously or after a time lag. The labeling agent and the method of insolubilization can be based on those described above. Also, in the immunoassay by the sandwich method, the antibody used as the antibody for a solid phase or the antibody for labeling needs not always be one kind; a mixture of two kinds or more of antibodies may be used for the purposes of measurement sensitivity improvement and the like.

In the measurement of ABP1 by the sandwich method, the antibodies of the present invention used in the primary reaction and the secondary reaction are preferably antibodies having mutually different sites for binding of ABP1. For example, provided that the antibody used for the secondary reaction recognizes a C-terminal portion of ABP1 as described above, the antibody used for the primary reaction is preferably an antibody that recognizes a site other than the C-terminal portion, for example, an N-terminal portion.

The antibody of the present invention can be used for a measurement system other than the sandwich method, for example, the competitive method, the immunometric method or nephelometry and the like.

In the competitive method, the antigen and the labeled antigen in the test solution are competitively reacted with the antibody, after which the unreacted labeled antigen (F) and the antibody-bound labeled antigen (B) are separated (B/F separation), the amount labeled of either B or F is measured, and the amount of antigen in the test solution is quantified. For this reaction method, the liquid phase method, wherein a soluble antibody is used as the antibody and B/F separation is conducted using polyethylene glycol, a second antibody against the above-described antibody (first antibody), and the like, and the solid phase immobilization method, wherein a solid-phase-immobilized antibody is used as the first antibody or the first antibody used is a soluble one and a solid-phase-immobilized antibody is used as the second antibody, can be used.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

Also, in nephelometry, the amount of insoluble precipitate resulting from an antigen-antibody reaction in the gel or in the solution is measured. Even when the amount of antigen in the test solution is small and only a small amount of precipitate is obtained, laser nephelometry, which utilizes laser scattering, and the like are preferably used.

In applying these individual immunological measurement methods to the quantitation method of the present invention, it is unnecessary to set special conditions, procedures and the like. Making ordinary technical considerations for those skilled in the art to the ordinary conditions and procedures in each method, a measurement system for an ABP1 can be constructed. For details of these general technical means, compendia, books and the like can be referred to.

For example, edited by Hiroshi Irie, "Rajioimunoassei" (Kodansha, published in 1974), edited by Hiroshi Irie, "Zoku Rajioimunoassei" (Kodansha, published in 1979), edited by Eiji Ishikawa et al., "Kouso Meneki Sokuteihou" (Igaku-Shoin, published in 1978), edited by Eiji Ishikawa et al., "Kouso Meneki Sokuteihou" (2nd edition) (Igaku-Shoin, published in 1982), edited by Eiji Ishikawa, "Kouso Meneki Sokuteihou" (3rd edition) (Igaku-Shoin, published in 1987), "Methods in ENZYMOLOGY", Vol. 70 (Immunochemical Techniques (Part A)), ibidem, Vol. 73 (Immunochemical Techniques (Part B)), ibidem, Vol. 74 (Immunochemical Techniques (Part C)), ibidem, Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press) and the like can be referred to.

Using the antibody of the present invention as described above, ABP1 or a salt thereof can be quantified at high sensitivity.

Therefore, if a decrease in ABP1 concentration is detected by quantifying the concentration of ABP1 or a salt thereof in a biological sample (e.g., blood, plasma, urine, biopsy and the like) from a test warm-blooded animals using the antibody of the present invention, the animal can be diagnosed as sufferng from or being likely to suffer from a disease associated suppression of apoptosis, for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like), post-angioplastic restenosis, recurrence after cancer resection and the like.

On the other hand, if an increase in ABP1 concentration is detected, the animal can be diagnosed as suffering from or being likely to suffer from a disease associated with apoptosis promotion or inflammation, for example, viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

(4) An Agent for Inhibiting ASK1 Activation and an Agent for Suppressing Apoptosis The antibody of the present invention is capable of inhibiting the binding of ABP1 to ASK1 to inactivate (i.e., neutralize) the ASK1 activation and apoptosis/inflammatory cytokine production induction promotion action, by specifically binding to ABP1. On the other hand, because the antisense polynucleotide of the present invention inhibits the expression of ABP1 to decrease the production of the protein, it is hence capable of reducing ASK1 activation and apoptosis/inflammatory cytokine production induction promotion action of ABP1.

Therefore, by adding the antibody of the present invention to cells to inactivate ABP1, or by introducing the antisense polynucleotide of the present invention to cells to reduce the ABP1 content in the cells, it is possible to inhibit the activation of ASK1 in the cells, and to suppress apoptosis/inflammatory cytokine production of the cells, and the antibody and antisense polynucleotide of the present invention can be used as, for example, reagents for research on apoptosis and inflammatory reactions.

When the antibody of the present invention is used as the above-described agent for inhibiting ASK1 activation or agent for suppressing apoptosis/inflammatory cytokine production, it can be prepared by being dissolved in water or an appropriate buffer solution (e.g., phosphate buffer solution, BS, Tris-HCl buffer solution and the like) to obtain an appropriate concentration. Also, as required, a commonly used preservative, stabilizer, reducing agent, isotonizing agent and the like may be formulated.

On the other hand, when the antisense polynucleotide of the present invention is used as the above-described agent for inhibiting ASK1 activation or agent for suppressing apoptosis, the polynucleotide alone, or after insertion to an appropriate vector such as the retrovirus vector, the adenovirus vector or the adenovirus-associated virus vector, can be introduced to cells using the above-described method of transformation (e.g., liposome method, electroporation method and the like).

(5) Prophylactic or Therapeutic Agent for Disease Associated with Apoptosis Promotion or Inflammation As described above, because ABP1 has the function of activating ASK1 to induce apoptosis to cells and evoke inflammation, various diseases, for example, viral infections, endocrine diseases, hematological diseases, organ hypoplasia, organ graft rejection, graft-versus-host disease, immune deficiency, neurodegenerative diseases, ischemic heart diseases, radiation injuries, ultraviolet injuries, poisoning diseases, nutritional disorders, inflammation, ischemic neuropathy (cerebral ischemia), diabetic peripheral neuropathies, vascular diseases, respiratory diseases, articular diseases and the like develop if there is an abnormality in ABP1 or a nucleic acid that encodes the same (e.g., gene, mRNA and the like) in the body (emergence of highly active variant), if the expression level is abnormally increases, or if apoptosis induction or inflammatory cytokine production in cells is abnormally promoted due to any other factor.

Therefore, it is possible to suppress the apoptotic death of originally essential cells and inflammatory reactions by: a) administering the antibody of the present invention to a patient who lacks cells that are essential to the body by apoptosis, or who has an inflammatory disease, due to an increase in ABP1 and the like, to inactivate ABP1, or by b) reducing the ABP1 content in the patient's body by (i) administering the antisense polynucleotide of the present invention to the patient to introduce (and express) it to the target cell, or (ii) introducing the antisense polynucleotide of the present invention to the isolated target cell to allow its expression, and transferring the cell to the patient.

Accordingly, a) the antibody of the present invention or b) the antisense polynucleotide of the present invention can be used as a prophylactic or therapeutic agent for a disease in which suppression of apoptosis or inflammation is effective for the prophylaxis or therapy thereof, for example, a disease caused by ABP1 overexpression and the like, specifically viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

When the antibody of the present invention is used as the above-described prophylactic or therapeutic agent, it can be formulated in the same manner as the aforementioned pharmaceutical containing ABP1, the activating peptide of the present invention, or a salt thereof. Also, when the antisense polynucleotide of the present invention is used as the above-described prophylactic or therapeutic agent, it can be formulated in the same manner as the aforementioned pharmaceutical containing a polynucleotide that encodes ABP1 or the activating peptide of the present invention.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of the antibody of the present invention varies depending on subject of administration, target organ, symptoms, method of administration and the like; in a polyglutamine disease patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a polyglutamine disease patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

The dosage of the antisense polynucleotide of the present invention varies depending on subject of administration, target organ, symptoms, method of administration and the like; in a polyglutamine disease patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a polyglutamine disease patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

(6) Use of the Inhibitory Peptide of the Present Invention

As described above, because the inhibitory peptide of the present invention is capable of functioning as an (antagonistic) substance for inhibiting ABP1, that is, capable of binding to ASK1 but does not activate or is capable of inactivating the same, it can be used as an agent for inhibiting ASK1 activation, an agent for suppressing apoptosis/inflammatory cytokine production, or a prophylactic or therapeutic agent for a disease associated with apoptosis promotion or inflammation, as with the antibody of the present invention.

When the inhibitory peptide of the present invention is used as an agent for inhibiting ASK1 activation or an agent for suppressing apoptosis or inflammatory cytokine production, a reagent can be prepared in the same manner as the aforementioned agent for promoting ASK1 activation or the agent for inducing apoptosis, containing ABP1, the activating peptide of the present invention, or a salt thereof. Also, when the inhibitory peptide of the present invention is used as the above-described prophylactic or therapeutic agent, it can be formulated in the same manner as the aforementioned pharmaceutical containing ABP1, the activating peptide of the present invention, or a salt thereof.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of the inhibitory peptide of the present invention varies depending on subject of administration, target organ, symptoms, method of administration and the like; in a polyglutamine disease patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a polyglutamine disease patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

(7) Use of ASK1 Partial Peptide not having Phosphorylation activity or a Salt Thereof As demonstrated in the Examples below, because the site involved in the binding of ASK1 and ABP1 is an activation control domain on the N-terminal side, a partial peptide of ASK1 that has an activation control domain but lacks a kinase domain responsible for the activation of MAPKK, which is located downstream of the cascade is capable of functioning as an (antagonistic) substance for inhibiting ASK1. Accordingly, because the peptide is capable of binding to ABP1 but cannot be activated thereby, it is capable of competitively inhibiting the binding of ASK1 and ABP1 present in cells and the activation of ASK1 thereby. Therefore, the partial peptide can be used as an agent for inhibiting ABP1, an agent for suppressing apoptosis or inflammatory cytokine production, or a prophylactic or therapeutic agent for a disease associated with apoptosis promotion or inflammation.

As the kinase domain of ASK1, in the case of human ASK1, for example, the amino acid sequence shown by amino acid numbers 678 to 936 in the amino acid sequence shown by SEQ ID NO:1 in the sequence listing of the aforementioned patent document 1 (Japanese Patent Publication No. HEI10-93) can be mentioned. Therefore, as the partial peptide of ASK1 that has an activation control domain on the N-terminal side, and that lacks a kinase domain (hereinafter also abbreviated as "the ASK1 partial peptide of the present invention"), a peptide that comprises the same or substantially the same amino acid sequence as the entire or a portion of the amino acid sequence shown by amino acid numbers 1 to 677 in the above-described human ASK1 amino acid sequence (hereinafter comprehensively referred to as "ASK1-N sequence"), and that is capable of binding to ABP1, can be mentioned. Here, as "substantially the same amino acid sequence", an amino acid sequence having a homology of about 70% or more, preferably about 80% or more, more preferably about 90% or more, particularly preferably about 95% or more, and most preferably about 98% or more, to the entire or a portion of the amino acid sequence shown by amino acid numbers 1 to 677 in the above-described human ASK1 amino acid sequence, and the like can be mentioned.

Examples of the ASK1 partial peptide of the present invention also include variant peptides that comprises (i) an amino acid sequence having one or two or more amino acids (preferably about 1 to about 30, preferably about 1 to about 10, more preferably several (1 to 5) amino acids) deleted from the ASK1-N sequence, (ii) an amino acid sequence having one or two or more amino acids (preferably about 1 to about 30, preferably about 1 to about 10, more preferably several (1 to 5) amino acids) added to the ASK1-N sequence, (iii) an amino acid sequence having one or two or more amino acid (preferably about 1 to about 30, preferably about 1 to about 10, more preferably several (1 to 5) amino acids) inserted to the ASK1-N sequence, (iv) an amino acid sequence having one or two or more amino acids (preferably about 1 to about 30, preferably about 1 to about 10, more preferably several (1 to 5) amino acids) substituted with other amino acids in the ASK1-N sequence, or (v) an amino acid sequence as a combination thereof.

The ASK1 partial peptide of the present invention can be prepared in the same manner as the above-described partial peptide of ABP1.

When the ASK1 partial peptide of the present invention is used as an agent for inhibiting ABP1, particularly as an agent for suppressing apoptosis or inflammatory cytokine production, a reagent can be prepared in the same manner as the aforementioned agent for promoting ASK1 activation or the agent for inducing apoptosis, containing ABP1, the activating peptide of the present invention, or a salt thereof. Also, when the ASK1 partial peptide of the present invention is used as the above-described prophylactic or therapeutic agent, it can be formulated in the same manner as the aforementioned pharmaceutical containing ABP1, the activating peptide of the present invention or a salt thereof.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of the ASK1 partial peptide of the present invention varies depending on subject of administration, target organ, symptoms, method of administration and the like; in a polyglutamine disease patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like;

in a polyglutamine disease patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

(4) Screening for a Substance which Regulates ASK1 activation

The present invention also provides a screening method for a substance which regulates ASK1 activation using ABP1, the activating peptide of the present invention or a salt thereof or a cell that produces the same. The screening method is roughly classified into (A) a method utilizing the binding of ABP1 and ASK1, (B) a method with ASK1 activation as an index, and (C) a method with ABP1 expression level as an index. In the methods (A) and (B), ASK1 or a partial peptide thereof that remains bindable to ABP1 (that is, a partial peptide containing at least an N-terminal activation control domain) or a salt thereof or a cell that produces the same is further used.

(A) Screening Method Utilizing the Binding of ABP1 and ASK1

Because ABP1 is capable of binding to ASK1 to activate the same, it is possible to conduct screening for a compound showing the same action as ABP1 or the activating peptide of the present invention, and to conduct screening for a compound that inhibits the action of ABP1 or the activating peptide of the present invention, by constructing a binding assay system using ABP1 or the activating peptide of the present invention and ASK1 or a partial peptide thereof containing an N-terminal side activation control domain. Accordingly, the present invention provides a screening method for a substance which regulates ASK1 activation, which comprises using ABP1 or the activating peptide of the present invention and ASK1 or a partial peptide thereof containing an N-terminal side activation control domain.

More specifically, the present invention provides:

(a) a screening method for a substance which regulates ASK1 activation, which comprises comparing the amount bound of ASK1 or a partial peptide thereof containing an N-terminal side activation control domain and ABP1 or the activating peptide of the present invention between (1) a case wherein ABP1 or the activating peptide of the present invention is brought into contact with ASK1 or a partial peptide thereof containing an N-terminal side activation control domain, and (2) a case wherein ABP1 or the activating peptide of the present invention and a test substance are brought into contact with ASK1 or a partial peptide thereof containing an N-terminal side activation control domain, (b) a screening method for a substance which regulates ASK1 activation, which comprises comparing the amount bound of ASK1 or a partial peptide thereof containing an N-terminal side activation control domain and ABP1 or the activating peptide of the present invention between (1) a case wherein ABP1 or the activating peptide of the present invention is brought into contact with a cell that produces ASK1 or a partial peptide thereof containing an N-terminal side activation control domain, and (2) a case wherein ABP1 or the activating peptide of the present invention and a test substance are brought into contact with a cell that produces ASK1 or a partial peptide thereof containing an N-terminal side activation control domain, and (c) a screening method for a substance which regulates ASK1 activation, which comprises comparing the expression levels of the reporter gene in a cell that produces ASK1 or a partial peptide thereof containing an N-terminal side activation control domain and ABP1 or the activating peptide of the present invention, and that has the transcription of the reporter gene activated upon binding of the two, in the presence and absence of a test substance.

The ASK1 used in the screening method (a) or (b) above can be isolated and purified from cells of a human or another warm-blooded animal using a method known per se (for example, the same method as the method mentioned above with respect to ABP1). The partial peptide of ASK1 containing an N-terminal side activation control domain is not subject to limitation, as long as it comprises the above-described amino acid sequence of an N-terminal side activation control domain, and may comprise a kinase domain or a portion of an amino acid sequence on the C terminal side. The partial peptide can be prepared by digesting ASK1 with an appropriate protease. The ASK1 or a partial peptide thereof containing an N-terminal side activation control domain can also be produced by gene recombination using the aforementioned method of expressing ABP1 after the DNA that encodes it is cloned according to a gene engineering technique known per se.

ABP1 and the activating peptide of the present invention (hereinafter also simply referred to as ABP1) can be prepared in accordance with the above-described method.

The cell that produces ASK1 is not subject to limitation, as long as they are cells of a human or any other warm-blooded animal that expresses it; for example, HeLa cells, HEK293 cells and the like can be mentioned. As examples of the cell that produces ASK1 or a partial peptide thereof containing the N-terminal side activation control domain (hereinafter also simply referred to as ASK1), a transformant prepared by the above-described gene engineering technique can be mentioned.

As examples of the test substance, a protein, a peptide, a non-peptide compound, a synthetic compound, a fermentation product, a cell extract, a plant extract, an animal tissue extract and the like can be mentioned, and these substances may be novel or publicly known.

A measurement of the amount bound can be conducted by, for example, Western blot analysis using a labeled anti-ABP1 antibody and anti-ASK1 antibody, binding assay or gel shift assay using either ABP1 or ASK1 labeled with, for example, $[^3H]$, $[^{125}I]$, $[^{14}C]$, $[^{35}S]$ or the like, or surface plasmon resonance (SPR) and the like.

In the above-described screening method, a compound that binds to ASK1 to inhibit the binding of ABP1 and ASK1 can be selected as a substance which regulates ASK1 activation.

In this screening method, the reaction of ABP1 and ASK1 can normally be conducted at about 37° C. for about several hours.

For example, when the above-described screening method is performed by a binding assay using labeled ABP1, an ASK1 reference standard is first prepared by suspending ASK1 or a cell that produces the same in a buffer suitable for their screening. The buffer may be any buffer that does not inhibit the binding of ABP1 and ASK1, such as a phosphate buffer, tris-HCl buffer and the like having a pH of about 4 to 10 (desirably, pH of about 6 to 8). For the purpose of reducing non-specific binding, a surfactant such as CHAPS, Tween-80™ (Kao-Atlas Company), digitonin, deoxycholate or the like can be added to the buffer. Furthermore, to suppress the degradation of ABP1 and ASK1 by proteases, a protease inhibitor such as PMSF, leupeptin, bacitracin, aprotinin, E-64 (manufactured by Protein Research Institute) or pepstatin may also be added.

On the other hand, in the case of immobilized cells, ABP1 and ASK1 can be bound while the cells remain immobilized to a instrument for culture, i.e., remain allowed to grow, or using cells fixed with glutaraldehyde or para-formaldehyde. In this case, the buffer solution used is a culture medium, Hanks' solution and the like.

Then, a given amount (for example, about 10000 cpm to 1000000 cpm in the case of 2000 Ci/mmol) of labeled ABP1 (for example, $[^{125}I]$-labeled ABP1) is added to 0.01 ml to 10 ml of the ASK1 reference standard, and $10^{-4}$M to $10^{-10}$ M of a test substance is allowed to coexist. To determine non-specific binding (NSB), a reaction tube containing unlabeled ABP1 in large excess should also be provided. The reaction is carried out at 0° C. to 50° C., desirably 4° C. to 37° C., for 20 minutes to 24 hours, desirably 30 minutes to 3 hours. After completion of the reaction, the reaction mixture is filtered through glass fiber filter paper and the like (when ASK1-producing cells are used) or subjected to B/F separation (when purified ASK1 is used), and the glass fiber filter paper or the solid phase is washed with an appropriate amount of the same buffer; subsequently, the radioactivity (for example, the amount of $[^{125}I]$) remaining in the glass fiber filter paper or the solid phase is determined using a liquid scintillation counter or a γ-counter. Assuming that the count ($B_0$-NSB) obtained by subtracting non-specific binding (NSB) from the count ($B_0$) in the absence of an antagonizing substance is to be 100%, a test substance having a specific binding (B-NSB) of, for example, 50% or less of the count ($B_0$-NSB), can be selected as a substance which regulates ASK1 activation.

The screening kit of the present invention includes ABP1, and preferably further includes ASK1 or a cell that produces the same.

As examples of the screening kit of the present invention, the following can be mentioned, which, however, are not to be construed as limiting.

[Screening Reagents]
(i) Buffer solutions for measurement and buffer solution for washing
Hanks' Balanced Salt Solution (manufactured by Gibco) having 0.05% bovine serum albumin (manufactured by Sigma Ltd.) added thereto. May be sterilized by filtration through a filter of 0.45 μm pore diameter and stored at 4° C., or may be freshly prepared before use.
(ii) Reference standard of ASK1
HeLa cells or HEK293 cells, subcultured in a 12-well plate at $5\times10^5$ cells/well, are cultured at 37° C. in the atomsphere of 5% $CO_2$ and 95% air for 2 days.
(iii) Labeled reference standard of ABP1
ABP1 labeled with [$^3$H], [$^{125}$I], [$^{14}$C], [$^{35}$S] and the like.
(iv) Standard ABP1 solution
ABP1 is dissolved in a PBS containing 0.1% bovine serum albumin (manufactured by Sigma) to obtain a 0.1 mM concentration and stored at −20° C.

[Measurement Method]
(i) After ASK1-producing cells cultured in a 12-well tissue culture plate and washed twice with 1 ml of the buffer solution for measurement, 490 μl of the buffer solution for measurement is added to each well.
(ii) After 5 μl of a $10^{-3}$ to $10^{-10}$ M test substance solution is added, 5 μl of 5 nM labeled ABP1 is added, and they are reacted at room temperature for 1 hour. To quantify the non-specific binding, 5 μl of a $10^{-4}$ M ABP1, in place of the test substance, is added in advance.
(iii) The reaction liquor is removed and washed with 1 ml of the buffer solution for washing three times. The cell-bound labeled ABP1 is dissolved in 0.5 ml of 0.2N NaOH-1% SDS and mixed with 4 ml of liquid scintillator A (manufactured by Wako Pure Chemical Industries).
(iv) Radioactivity is measured using a liquid scintillation counter (manufactured by Beckman Instruments), and Percent Maximum Binding (PMB) is calculated using the equation shown below. Provided that the sample has been labeled with [$^{125}$I], it can be measured directly, without being mixed with a liquid scintillator, using a gamma counter.
PMB=100×(B−NSB)/($B_0$−NSB)
PMB: Percent Maximum Binding
B: Binding obtained with addition of sample
NSB: Non-specific binding
$B_0$: Maximum amount bound As the cells used in the screening method (c) above, cells containing (1) a DNA that encodes a fusion protein of ASK1 or a partial peptide thereof containing an N-terminal side activation control domain and either a DNA-binding domain or transcription activation domain of a transcription factor (for example, GAL4, VP16 and the like), (2) a DNA that encodes a fusion protein of ABP1 or the activating peptide of the present invention and the other domain of the transcription factor, and (3) a reporter gene under the control of a promoter activated by the transcription factor, preferably a yeast cell, a mammal cell and the like can be mentioned. As examples of the reporter gene, the luciferase gene, β-galactosidase gene, the alkaline phosphatase gene, the peroxidase gene, the chloramphenicol acetyltransferase gene, green fluorescent protein (GFP) gene and the like can be mentioned.

In this screening method, the above-described cell is cultivated under cultivation conditions suitable for the host cell used for about several hours to 1 day, a cell extract or supernatant is obtained, and the reporter gene is detected by a conventional method.

In the above-described screening method, a compound that inhibits the expression of the reporter gene can be selected as a substance which regulates ASK1 activation.

(B) Screening Method with ASK1 Activation as Index
By determining the effect of the test substance on the interaction of ABP1 and ASK1 by measuring the activation of ASK1, whether the substance inhibits or promotes the activation of ASK1 can be evaluated directly. Accordingly, the present invention provides a screening method for a substance which regulates ASK1 activation, which comprises measuring and comparing the activation of the protein or the peptide in a cell that produces ASK1 or a partial peptide thereof containing an N-terminal side activation control domain and a kinase domain, (1) in the presence of ABP1 or the activating peptide of the present invention and (2) in the presence of ABP1 or the activating peptide of the present invention and a test substance.

In this screening method, as the cell that produces ASK1 or a partial peptide thereof containing an N-terminal side activation control domain and a kinase domain (hereinafter also simply referred to as ASK1-producing cells), cells that endogenously produce ASK1 (e.g., HeLa cells, HEK293 cells and the like), animal cells incorporating a DNA that encodes ASK1 or a partial peptide thereof containing an N-terminal side activation control domain and a kinase domain, and the like can be mentioned.

As the partial peptide of ASK1 containing an N-terminal side activation control domain and a kinase domain, a peptide that comprises the same or substantially the same amino acid sequence as the entire or a portion of the amino acid sequence shown by amino acid numbers 1 to 936 in the amino acid sequence shown by SEQ ID NO:1 in the sequence listing of the aforementioned patent document 1 (Japanese Patent Publication No. HEI10-93) (hereinafter comprehensively referred to as "ASK1-NK sequence"), and that can be activated as a result of binding with ABP1 can be mentioned. Here, as "substantially the same amino acid sequence", an amino acid sequence having a homology of about 70% or more, preferably about 80% or more, more preferably about 90% or more, particularly preferably about 95% or more, and most preferably about 98% or more, to the above-described human ASK1-NK sequence and the like can be mentioned.

Examples of the above-described partial peptide also include variant peptides that comprises (i) an amino acid sequence having one or two or more amino acids (preferably about 1 to about 30, preferably about 1 to about 10, more preferably several (1 to 5) amino acids) deleted from the ASK1-NK amino acid sequence, (ii) an amino acid sequence having one or two or more amino acids (preferably about 1 to about 30, preferably about 1 to about 10, more preferably several (1 to 5) amino acids) added to the ASK1-NK amino acid sequence, (iii) an amino acid sequence having one or two or more amino acid (preferably about 1 to about 30, preferably about 1 to about 10, more preferably several (1 to 5) amino acids) inserted to the ASK1-NK amino acid sequence, (iv) an amino acid sequence having one or two or more amino acids (preferably about 1 to about 30, preferably about 1 to about 10, more preferably several (1 to 5) amino acids) substituted with other amino acids in the ASK1-NK amino acid sequence, or (v) an amino acid sequence as a combination thereof.

ABP1 or the activating peptide of the present invention (hereinafter also simply referred to as ABP1) may be added to the cell from outside, or may be produced by the ASK1-producing cell itself. In the latter case, ABP1 may be produced endogenously, or may be a transformant prepared with the ASK1-producing cell as a host by gene engineering according to the above-described method of expressing ABP1.

As examples of the test substance, a protein, a peptide, a non-peptide compound, a synthetic compound, a fermentation product, a cell extract, a plant extract, an animal tissue extract and the like can be mentioned, and these substances may be novel or publicly known.

The activation of ASK1 can be evaluated by measuring the autophosphorylation of ASK1, the phosphorylation of a kinase located downstream of the ASK1 cascade (for example, MKK4/7, MKK3/6, JNK, p38 and the like) or another protein or synthetic peptide capable of serving as a substrate of ASK1, cell death induction rate and the like.

Specifically, ASK1-producing cells are first cultivated using a multiwell plate and the like. Prior to screening, the medium is replaced with a fresh medium or an appropriate buffer not toxic to the cells, a test substance (and also ABP1 if the cells do not produce ABP1) and the like are added, incubation is conducted for a given time, the cell is extracted or the supernatant is recovered, and the resulting product or phenomenon is quantified according to respective methods.

Detection of phosphorylation of ASK1 or another protein or a peptide can be conducted by methods such as Western blot analysis using a specific antibody against a phosphorylated protein (peptide) and the detection of the uptake of [$^{32}$P]-labeled ATP in substrate protein (peptide) by gel electrophoresis and autoradiography.

Cell death assay can be conducted by calculating the ratio of dead cells to all ABP1-expressing cells in a system that enables the confirmation of the expression of ABP1 (for example, cells incorporating DNA that encodes a fusion protein of ABP1 and a fluorescent protein, or cells incorporating the ABP1 expression vector further containing a selection marker gene), with detachment from the plate, morphological examination (e.g., membrane blebbing, fragmentation and the like) and the like as an index.

In the above-described screening method, if ASK1 is activated with the addition of a test substance to the ASK1-producing cell, the substance can be selected as a substance for promoting ASK1 activation. On the other hand, if ASK1 is inactivated with the addition of the test substance, the substance can be selected as a substance for inhibiting ASK1 activation.

(C) Screening Method for Substance that Alters the Expression Level of ABP1

Using the sense and antisense polynucleotides of the present invention as probes, or using the antibody of the present invention, it is possible to screen for a substance that alters the expression level of ABP1.

Accordingly, the present invention provides a screening method for a substance that alters the expression level of ABP1, hence a substance which regulates ASK1 activation, by, for example, measuring the ABP1 mRNA content or ABP1 protein content contained in (i) a) blood, b) a particular organ, or c) a tissue or cells isolated from an organ, of a non-human mammal, or in (ii) a transformant and the like.

For example, a measurement of the mRNA content or protein content of ABP1 is specifically conducted as described below.

(i) A drug (for example, TNF-α, IL-1, Fas, anticancer agents and the like), a physicochemical stress (for example, UV, active oxygen, ischemia and the like) or the like is added to a normal or pathologic model non-human mammal (for example, mouse, rat, rabbit, sheep, swine, bovine, cat, dog, monkey and the like), and after a given time has elapsed, blood or a particular organ (for example, brain, liver, kidney and the like), or a tissue or cells isolated from the organ are obtained.

The mRNA of the ABP1 contained in the cells obtained can be quantified by, for example, extracting the mRNA from the cells and the like by an ordinary method, and using a technique, for example, RT-PCR and the like, and can also be quantified by a Southern blot analysis known per se. On the other hand, the ABP1 protein content can be quantified by extracting the protein from the cells and the like by an ordinary method, and conducting, for example, Western blot analysis using a labeled anti-ABP1 antibody.

(ii) A transformant that expresses ABP1 or the activating peptide of the present invention is prepared according to the above-described method, and the ABP1 or the activating peptide of the present invention contained in the transformant, or the mRNA thereof, can be quantified and analyzed in the same manner.

Screening for a compound that alters the expression level of ABP1 can be conducted by:

(i) administering a test substance to a normal or pathologic model non-human mammal before a given time (30 minutes previously to 24 hours previously, preferably 30 minutes previously to 12 hours previously, more preferably 1 hour previously to 6 hours previously) or after a given time (30 minutes later to 3 days later, preferably 1 hour later to 2 days later, more preferably 1 hour later to 24 hours later) of administration of a drug, a physicochemical stress or the like, or simultaneously with administration of the drug or the physicochemical stress, and quantifying and analyzing the mRNA content or protein content of the ABP1 contained in the cells after the elapse of a given time following administration (30 minutes later to 3 days later, preferably 1 hour later to 2 days later, more preferably 1 hour later to 24 hours later), or by:

(ii) cultivating a transformant according to a conventional method in the presence of a test substance in the culture medium, and quantifying and analyzing the mRNA content or protein content of the ABP1 or the activating peptide of the present invention contained in the transformant after a given time of cultivation (1 day later to 7 days later, preferably 1 day later to 3 days later, more preferably 2 days later to 3 days later).

As the test substance, a peptide, a protein, a non-peptide compound, a synthetic compound, a fermentation product and the like can be mentioned, and these substances may be novel substances or publicly known substances.

In the above-described screening method, a substance that increases the expression level of ABP1 can be selected as a substance for promoting ASK1 activation, and a substance that decreases the expression level of ABP1 can be selected as a substance for inhibiting ASK1 activation.

A substance that increases the expression or activity of ABP1 or a salt thereof, obtained using the screening methods (A) to (C) above (=substance for promoting ASK1 activation, in the present specification, hereinafter used with the same meaning), is capable of activating signal transduction via the ASK1 cascade to induce apoptosis to cells. Therefore, it is possible to induce apoptosis to cells by adding a substance for promoting ASK1 activation to the cell, and a substance for promoting ASK1 activation can be used as, for example, reagents for research into apoptosis.

When a substance for inhibiting ASK1 activation is used as an agent for inducing apoptosis, it can be prepared by being dissolved in water or an appropriate buffer solution (e.g., phosphate buffer solution, PBS, Tris-HCl buffer solution and the like) to obtain an appropriate concentration. Also, as required, a commonly used preservative, stabilizer, reducing agent, isotonizing agent and the like may be formulated.

As described above, because the substance for promoting ASK1 activation has the function of inducing apoptosis to cells, for a patient not expected to have the removal of unwanted cells and abnormal cells by apoptosis due to a reduction in ABP1 or any other factor, it is possible to induce apoptosis via the ASK1 cascade in the abnormal cells and unwanted cells in the patient's body by administering a substance for promoting ASK1 activation to the patient to activate ASK1.

Therefore, the substance for promoting ASK1 activation can be used as a prophylactic or therapeutic agent for a disease in which induction of apoptosis is effective for the prophylaxis or therapy thereof, for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like), post-angioplastic restenosis, recurrence after cancer resection, and the like.

When a substance for inhibiting ASK1 activation is used as the above-described prophylactic or therapeutic agent, it can be formulated in the same manner as the aforementioned pharmaceutical containing ABP1 or the activating peptide of the present invention or a salt thereof.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of the substance for promoting ASK1 activation varies depending on subject of administration, target organ, symptoms, method of administration and the like; in a cancer patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a cancer patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

On the other hand, a substance that decreases the expression or activity of ABP1 or a salt thereof, obtained using the screening methods (A) to (C) above (=substance for inhibiting ASK1 activation; in the present specification, hereinafter used with the same meaning) is capable of inhibiting signal transduction via the ASK1 cascade to suppress apoptosis and inflammatory cytokine production in cells. Therefore, it is possible to suppress the apoptosis/inflammatory cytokine production of the cell by adding a substance for inhibiting ASK1 activation to the cell, and the substance for inhibiting ASK1 activation can be used as, for example, reagents for research into apoptosis, inflammatory reactions and the like.

When a substance for inhibiting ASK1 activation is used as an agent for suppressing apoptosis or inflammatory cytokine production, it can be prepared by being dissolved in water or an appropriate buffer solution (e.g., phosphate buffer solution, PBS, Tris-HCl buffer solution and the like) to obtain an appropriate concentration. Also, as required, a commonly used preservative, stabilizer, reducing agent, isotonizing agent and the like may be formulated.

As described above, because the substance for inhibiting ASK1 activation has the function of suppressing cell apoptosis and inflammatory cytokine production, it is possible to suppress the apoptotic death of originally essential cells and inflammatory reactions by administering the substance for inhibiting ASK1 activation to a patient who lacks cells that are essential to the body by apoptosis, or who has an inflammatory disease, due to an increase in ABP1 and the likes, to inhibit ASK1 activation.

Accordingly, a substance for inhibiting ASK1 activation can be used as a prophylactic or therapeutic agent for a disease in which suppression of apoptosis or inflammation is effective for the prophylaxis or therapy thereof, for example, viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

When the substance for inhibiting ASK1 activation is used as the above-described prophylactic or therapeutic agent, it can be formulated in the same manner as the aforementioned pharmaceutical containing ABP1 or the activating peptide of the present invention or a salt thereof.

Because the preparation thus obtained is safe and of low toxicity, it can be administered to, for example, a human or another warm-blooded animal (for example, rat, mouse, hamster, rabbit, sheep, goat, swine, bovine, horse, cat, dog, monkey, chimpanzee, bird and the like).

The dosage of the substance for inhibiting ASK1 activation varies depending on subject of administration, target organ, symptoms, method of administration and the like; in a polyglutamine disease patient (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a polyglutamine disease patient (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body weight can be administered.

(8) Animal Introduced with a DNA that Encodes ABP1 and use Therefor

The present invention provides a new use for a non-human mammal having a foreign DNA that encodes ABP1 (hereinafter abbreviated as a foreign DNA of the present invention) or a variant DNA thereof (also abbreviated as foreign variant DNA of the present invention).

A non-human mammal used in the present invention is:
[1] a non-human mammal having a foreign DNA of the present invention or a variant DNA thereof,
[2] the mammal described in term [1], wherein the non-human mammal is a rodent, or
[3] the mammal described in term [2], wherein the rodent is a mouse or rat.

A non-human mammal having the foreign DNA of the present invention or a variant DNA thereof (hereinafter abbreviated as the DNA transgenic animal of the present invention) can be produced by transferring the desired DNA to a germ cell, including an unfertilized ovum, a fertilized ovum, a sperm and a primordial cell thereof, and the like, preferably in the stage of embryogenesis in the stage of development of the non-human mammal (more preferably, in the single-cell or fertilized ovum cell stage and generally at or prior to the 8-cell stage), by the calcium phosphate method, the electric pulse method, the lipofection method, the aggregation method, the microinjection method, the particle gun method, the DEAE-dextran method and the like. Also, it is possible to transfer the desired foreign DNA of the present invention to a somatic cell, an organ of a living body, a tissue cell and the like by the DNA transfer method, and utilize it for cell culture, tissue culture and the like; furthermore, it is also possible to produce the DNA transgenic animal of the present invention by fusing these cells with the above-described germ cell by a method of cell fusion known per se.

As examples of the non-human mammal, bovine, swine, sheep, goat, rabbit, dog, cat, guinea pig, hamster, mouse, rat and the like can be used. Particularly preferred from the viewpoint of preparation of a pathologic animal model system are rodents, which have relatively short ontogenesis and biological cycles, and which permit easy propagation, particularly the mouse (for example, C57BL/6 strain, DBA2 strain and the like as pure strains, B6C3F$_1$ strain, BDF$_1$ strain, B6D2F$_1$ strain, BALB/c strain, ICR strain and the like as cross strains) or the rat (for example, Wistar, SD and the like) and the like.

As the "mammal" in a recombinant vector that can be expressed in a mammal, human and the like can be mentioned, in addition to the above-described non-human mammals.

The foreign DNA of the present invention refers to the DNA that encodes ABP1 once isolated and extracted from a mammal, rather than to the DNA that encodes ABP1 originally possessed by a non-human mammal.

As the variant DNA of the present invention, one having a variation in the base sequence of the original ABP1-coding DNA (for example, mutation and the like), specifically DNA and the like having a base added, deleted, or substituted by another base, and the like can be used, and an abnormal DNA is also included.

The abnormal DNA means a DNA that expresses abnormal ABP1; for example, a DNA that expresses abnormal ABP1 that suppresses the function of normal ABP1 and the like can be used.

The foreign DNA of the present invention may be derived from a mammal of the same species as, or a different species from, the subject animal. In transferring the foreign DNA of the present invention to the subject animal, it is generally advantageous to use the DNA as a DNA construct bound downstream of a promoter capable of allowing the DNA to be expressed in an animal cell. For example, when the DNA that encodes human ABP1 is transferred, by microinjecting a DNA construct (e.g., vector and the like) having the DNA that encodes human ABP1 bound downstream of various promoters capable of expressing a DNA derived from various mammals (for example, rabbit, dog, cat, guinea pig, hamster, rat, mouse and the like) having a DNA highly homologous thereto to a fertilized ovum of a subject mammal, for example, a mouse fertilized ovum, a DNA transgenic mammal that expresses the DNA that encodes ABP1 at a high level can be produced.

As the expression vector for ABP1, an *Escherichia coli*-derived plasmid, a *Bacillus subtilis-derived* plasmid, a yeast-derived plasmid, a bacteriophage such as λ phage, a retrovirus such as Moloney leukemia virus, an animal virus such as vaccinia virus or baculovirus, and the like can be used. Particularly preferably used are an *Escherichia coli*-derived plasmid, a *Bacillus subtilis-derived* plasmid or a yeast-derived plasmid and the like.

As examples of the above-described promoter that regulates DNA expression, (i) promoters for DNAs derived from viruses (e.g., simian virus, cytomegalovirus, Moloney leukemia virus, JC virus, breast cancer virus, poliovirus and the like), (ii) promoters derived from various mammals (human, rabbit, dog, cat, guinea pig, hamster, rat, mouse and the like), for example, promoters for albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen type I and type II, cyclic AMP-dependent protein kinase βI subunit, dystrophin, tartaric acid-resistant alkaline phosphatase, atrial natriuretic factor, endothelial receptor tyrosine kinase (generally abbreviated as Tie2), sodium-potassium adenosine triphosphatase (Na,K-ATPase), neurofilament light chain, metallothionein I and IIA, metalloproteinase 1 tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin basic protein, thyroglobulin, Thy-1, immunoglobulin, H chain variable portion (VNP), serum amyloid P component, myoglobulin, troponin C, smooth muscle a actin, preproenkephalin A, vasopressin and the like, and the like can be used. Particularly preferred are the cytomegalovirus promoter, the human peptide chain elongation factor 1α (EF-1α) promoter, the human and chicken β actin promoters and the like, which can be expressed at high levels systemically.

The above-described vector preferably has a sequence that terminates the transcription of the desired mRNA in the DNA transgenic mammal (generally referred to as terminator); for example, the sequence of each DNA derived from a virus and derived from various mammals can be used, and the SV40 terminator of simian virus and the like can be used preferably.

Besides, for the purpose of expressing the desired foreign DNA at a higher level, the splicing signal and an enhancer region of each DNA, a portion of the intron of a eukaryotic DNA and the like can also be joined upstream of the 5' of the promoter region, between the promoter region and the translation region or downstream of the 3' of the translation region depending on the purpose.

The translation region of the normal ABP1 can be acquired as the entire or a portion of genomic DNA from a DNA from liver, kidney, thyroid cells or fibroblasts of a human or various mammals (for example, rabbit, dog, cat, guinea pig, hamster, rat, mouse and the like), or from commercially available various genomic DNA libraries, or using a complementary DNA prepared from an RNA derived from liver, kidney, thyroid cells, fibroblasts and the like by a publicly known method as the raw material. Also, for the foreign abnormal DNA, it is possible to prepare a translation region by mutating the translation region of normal ABP1 from the above-described cell or tissue by point mutagenesis.

The translation region can be prepared as a DNA construct that can be expressed in a transgenic animal by an ordinary DNA engineering technique wherein it is joined downstream of the aforementioned promoter and, as desired, upstream of the transcription termination site.

Transfer of the foreign DNA of the present invention in the fertilized ovum cell stage is assured so that it will be present in all germ cells and somatic cells of the subject mammal. The presence of the foreign DNA of the present invention in germ cells of the produced animal after the DNA transfer means that all progenies of the produced animal have the foreign DNA of the present invention in all germ cells and somatic cells thereof. Progenies of this kind of animal that have inherited the foreign DNA of the present invention have the foreign DNA of the present invention in all germ cells and somatic cells thereof.

A non-human mammal to which the foreign normal DNA of the present invention is transferred can be propagated over generations as an animal retaining the DNA in an ordinary rearing environment after the stable retention of the foreign DNA is confirmed by mating.

Transfer of the foreign DNA of the present invention in the fertilized ovum cell stage is assured so that it will be present in excess in all germ cells and somatic cells of the subject mammal. The excess presence of the foreign DNA of the present invention in germ cells of the produced animal after the DNA transfer means that all progenies of the produced animal have the foreign DNA of the present invention in excess in all germ cells and somatic cells thereof. Progenies of this kind of animal that have inherited the foreign DNA of the present invention have the foreign DNA of the present invention in all germ cells and somatic cells thereof in excess.

By acquiring a homozygous animal having the introduced DNA in both homologous chromosomes, and crossing a male and female of this animal, the animal can be propagated over generations so that all progenies will have the DNA in excess.

A non-human mammal having the foreign DNA of the present invention has the normal DNA of the present invention expressed at a high level therein, possibly finally develops ABP1 hyperfunction by promoting the function of endogenous normal DNA, and can be utilized as a pathologic model animal thereof. For example, using the normal DNA transgenic animal of the present invention, it is possible to elucidate the pathologic mechanism of ABP1 hyperfunction or disease associated with ABP1, and to investigate a therapeutic method for these diseases.

Also, because a mammal to which the foreign normal DNA of the present invention is transferred has a symptom of increased ABP1, it can also be utilized for a screening test for a prophylactic or therapeutic drug for a disease associated with increased function of ABP1, for example, viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

On the other hand, a non-human mammal having the foreign abnormal DNA of the present invention can be propagated over generations in an ordinary rearing environment as an animal having the DNA after the stable inheritance of the foreign DNA is confirmed by mating. Furthermore, the desired foreign DNA can be used as a raw material as incorporated in the aforementioned plasmid. A DNA construct with a promoter can be prepared by an ordinary DNA engineering technique. Transfer of the abnormal DNA of the present invention in the fertilized ovum cell stage is assured so that it will be present in all germ cells and somatic cells of the subject mammal. The presence of the abnormal DNA of the present invention in germ cells of the produced animal after the DNA transfer means that all progenies of the produced animal have the foreign abnormal DNA of the present invention in all germ cells and somatic cells thereof. By acquiring a homozygous animal having the introduced DNA in both homologous chromosomes, and crossing a male and female of this animal, the animal can be propagated over generations so that all progenies will have the DNA.

A non-human mammal having the exogenic abnormal DNA of the present invention has the abnormal DNA of the present invention expressed at a high level therein, possibly finally develops ABP1 function inactivation type unresponsiveness (for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like) and the like) by inhibiting the function of endogenous normal DNA, and can be utilized as a pathologic model animal thereof. For example, using the abnormal DNA transgenic animal of the present invention, it is possible to elucidate the pathologic mechanism of ABP1 function inactivation type unresponsiveness, and to investigate a therapeutic method for this disease.

Regarding the feasibility of specific application, an animal that expresses the abnormal DNA of the present invention at a high level can serve as a model for elucidating the inhibition of the function of normal ABP1 by abnormal ABP1 in ABP1 function inactivation type unresponsiveness (dominant negative action).

Also, because a mammal to which the foreign abnormal DNA of the present invention is transferred has a symptom of increase in abnormal ABP1, it can also be utilized for a screening test for a therapeutic drug for ABP1 function inactivation type unresponsiveness.

Furthermore, using the DNA transgenic animal of the present invention, it is possible to provide an effective and quick screening method for a prophylactic or therapeutic drug for a disease associated with ABP1, including ABP1 function inactivation type unresponsiveness, to develop the prophylactic or therapeutic drug using the above-described test method, quantitation method and the like. It is also possible to investigate and develop a gene therapy for a disease associated with ABP1, using the DNA transgenic animal of the present invention or the foreign DNA expression vector of the present invention.

(9) Knockout Animal

ABP1 DNA-expression-deficient non-human mammal embryonic stem cell and ABP1 DNA-expression-deficient non-human mammal used in the present invention are,

[1] a non-human mammal embryonic stem cell wherein the DNA that encodes ABP1 has been inactivated,

[2] the embryonic stem cell described in term [1], wherein the DNA has been inactivated by introducing a reporter gene (e.g., *Escherichia coli*-derived β-galactosidase gene),

[3] the embryonic stem cell described in term [1], which is resistant to neomycin,

[4] the embryonic stem cell described in term [1], wherein the non-human mammal is a rodent,

[5] the embryonic stem cell described in term [4], wherein the rodent is a mouse,

[6] the DNA-expression-deficient non-human mammal wherein the DNA that encodes ABP1 has been inactivated,

[7] the non-human mammal described in term [6], wherein the DNA has been inactivated by introducing a reporter gene (e.g., *Escherichia coli*-derived β-galactosidase gene), which reporter gene is expressible under the control of a promoter for a DNA that encodes ABP1,

[8] the non-human mammal described in term [6], wherein the non-human mammal is a rodent,

[9] the non-human mammal described in term [8], wherein the rodent is a mouse.

A non-human mammal embryonic stem cell wherein the DNA that encodes ABP1 has been inactivated refers to an embryonic stem cell (hereinafter abbreviated as ES cell) of a non-human mammal wherein the expressibility of the ABP1 DNA in the non-human mammal is suppressed by artificially mutating the DNA, or wherein the DNA is made substantially incapable of expressing ABP1 by substantially inactivating the ABP1 encoded by the DNA (hereinafter also referred to as a knockout DNA of the present invention).

As the non-human mammal, the same as those mentioned above can be used.

An artificial variation can be added to the ABP1-coding DNA by, for example, deleting a portion of or the entire DNA sequence, or inserting or substituting another DNA by a gene engineering technique. The knockout DNA of the present invention may be prepared by, for example, shifting the codon reading frame, or destroying the function of the promoter or exon, using these mutations.

Specifically, the non-human mammal embryonic stem cell having the ABP1-coding DNA inactivated (hereinafter abbreviated as DNA-inactivated ES cell of the present invention or a knockout ES cell of the present invention) can be obtained by, for example, constructing a DNA strand having a DNA sequence constructed so that the gene is destroyed (hereinafter abbreviated as targeting vector) by isolating the ABP1 DNA present in the desired non-human mammal, and inserting a drug resistance gene represented by the neomycin resistance gene and the hygromycin resistance gene, or a reporter gene represented by the lacZ gene (β-galactosidase gene) and the cat gene (the chloramphenicol acetyltransferase gene) and the like to the exon portion to destroy the exon function, or by inserting a DNA sequence that terminates the transcription of the gene (for example, polyA addition signal and the like) into an intron portion between exons to make the synthesis of complete mRNA impossible, to hence introduce the DNA strand to the animal's chromosome by, for example, the homologous recombination method, analyzing the obtained ES cells by Southern hybridization analysis with the DNA sequence on the ABP1 DNA or in the vicinity thereof as a probe, or the PCR method with the DNA sequence on the targeting vector and the DNA sequence in the vicinity other than the ABP1 DNA used to prepare the targeting vector as primers, and selecting the knockout ES cell of the present invention.

Also, the ES cell based on which the DNA that encodes ABP1 is inactivated by the homologous recombination method and the like, may be, for example, of an already established cell line as described above, and may also be newly established in accordance with the publicly known method of Evans and Kaufman. For example, in the case of a mouse ES cell, currently, an ES cell derived from the 129 strain mouse is generally used; however, since the immunological background is unclear, for example, an ES cell established from the C57BL/6 mouse or the $BDF_1$ mouse ($F_1$ of C57BL/6 and DBA/2), which has been developed by improving the low number of eggs recoverable from C57BL/6 by crossing with DBA/2', and the like can also be used favorably for the purpose of instead obtaining an ES cell which is of a pure strain, and which has an immunologically clear genetic background and the like. Because the $BDF_1$ mouse has the C57BL/6 mouse as the background, in addition to being advantageous in that the number of recoverable eggs is large and the eggs are tough, ES cells derived therefrom are advantageously usable in that the genetic background can be replaced with the C57BL/6 mouse by being back-crossed with the C57BL/6 mouse when the disease model mouse is prepared.

When an ES cell is established, blastcysts at 3.5 days after fertilization are normally used, but a large number of initial embryos can be obtained by recovering 8-cell embryos and cultivating them until the blastocyst stage before use.

Although the ES cell may be of either sex, a male ES cell is usually more convenient for preparation of a germ line chimera. Also, it is desirable, also for saving labor for painstaking cultivation, that sex identification be conducted as soon as possible.

As an example of the ES cell sex identification method, a method wherein the gene in the sex determination region on the Y chromosome is amplified and detected by the PCR method can be mentioned. Using this method, the number of ES cells can be reduced to about 1 colony (about 50 cells), in contrast to the conventional practice that requires a cell number of about $10^6$ cells for karyotype analysis, so that primary selection of ES cells in the initial stage of cultivation can be conducted by sex identification, which in turn makes it possible to significantly save labor in the initial stage of cultivation because early selection of male cells has been made possible.

Also, secondary selection can be conducted by, for example, confirmation of the chromosome number by the G-banding method, and the like. Although the chromosome number of the ES cells obtained is desirably 100% of the normal number, it is desirable that if the 100% level is difficult to achieve for the reasons of physical operation and the like at the time of cell line establishment, knockout of the gene of the ES cells be followed by re-cloning into normal cells (for example, cells having a chromosome number of 2n=40 in the case of the mouse).

The embryonic stem cell line thus obtained need to be carefully subcultured because it is likely to lose its potential for ontogeny, though it normally grows very well. For example, a method wherein the embryonic stem cell line is cultured on appropriate feeder cells like the STO fibroblast, in the presence of LIF (1 to 10,000 U/ml) in a carbonic acid gas incubator (preferably 5% carbonic acid gas, 95% air or 5% oxygen, 5% carbonic acid gas, 90% air) at about 37° C., and the like, and for passage, for example, the embryonic stem cell line is rendered to be single cells by a treatment with a trypsin/EDTA solution (usually 0.001 to 0.5% trypsin/0.1 to 5 mM EDTA, preferably about 0.1% trypsin/1 mM EDTA), and seeded onto freshly provided feeder cells, and the like can be used. This passage is usually conducted every 1 to 3 days, during which period the cells are examined; if a morphologically abnormal cell is found, the cultured cells are desirably discarded.

ES cells can be differentiated into various types of cells, including parietal muscle, visceral muscle and cardiac muscle, by monolayer culture until a high density is obtained, or by suspension culture until a cell aggregation is formed, under appropriate conditions [M. J. Evans and M. H. Kaufman, Nature, Vol. 292, p. 154, 1981; G. R. Martin, Proc. Natl. Acad. Sci. U.S.A., Vol. 78, p. 7634, 1981; T. C. Doetschman et al., Journal of Embryology and Experimental Morphology, Vol. 87, p. 27, 1985]; the DNA-expression-deficient cell of the present invention, obtained by differentiating the ES cell of the resent invention, is useful in cell biological investigations of ABP1 in vitro.

The DNA-expression-deficient non-human mammal of the resent invention can be distinguished from normal animals by measuring the mRNA contents in the animals using a publicly known method, and indirectly comparing the expression levels.

As the non-human mammal, the same as those mentioned above can be used.

The DNA-expression-deficient non-human mammal of the present invention can have the ABP1-coding DNA knocked out by, for example, introducing the targeting vector prepared as described above to a mouse embryonic stem cell or a mouse ovum cell, and replacing the DNA sequence having the ABP1 DNA of the targeting vector inactivated by this introduction with the ABP1 DNA on the chromosome of the mouse embryonic stem cell or mouse ovum cell by homologous recombination.

The cell having a knockout DNA that encodes ABP1 can be identified by Southern hybridization analysis with the DNA sequence on ABP1 DNA or a DNA sequence in the vicinity thereof as a probe, or by an analysis using the PCR method with the DNA sequence on the targeting vector and a DNA sequence in the vicinity other than the mouse ABP1 DNA used in the targeting vector as primers. When a non-human mammal embryonic stem cell is used, the cell line having the ABP1-coding DNA inactivated is cloned by homologous recombination, and the cell is injected to a non-human mammal embryo or blastcysts at an appropriate time, for example, in the 8-cell stage, and the thus-obtained chimeric embryo is transferred to the uterus of a pseudopregnant non-human mammal. The produced animal is a chimeric animal that comprises both cells having the normal ABP1 gene locus and an artificially varied ABP1 DNA locus.

Provided that some of the germ cells of the chimeric animal have a variant ABP1 DNA locus, from a group of individuals obtained by crossing such a chimeric individual and a normal individual, an individual wherein all tissues comprise cells having the artificially variant ABP1 DNA locus can be obtained by, for example, coat color identification and the like. The thus-obtained individuals are normally ABP1 hetero-expression-deficient individuals and ABP1 homo-expression-deficient individuals can be obtained from among the babies resulting from crossing of ABP1 hetero-expression-deficient individuals.

When an ovum cell is used, a transgenic non-human mammal having a targeting vector introduced to the chromosome thereof can be obtained by, for example, injecting a DNA solution into the ovum cell nucleus by the microinjection method, and these animals are obtained by selecting those having a mutation in the ABP1 DNA locus by homologous recombination, compared to the transgenic non-human mammals.

Individuals having the ABP1 DNA thus knocked out can be propagated over generations in an ordinary rearing environment after the individual animals obtained by crossing are confirmed as also having the knockout DNA.

Furthermore, acquirement and maintenance of the germ cell line can also be achieved according to a conventional method. That is, by crossing a male and female of the animal having the inactivated DNA, a homozygous animal having the inactivated DNA in both homologous chromosomes can be acquired. The homozygotic animal can be obtained efficiently by rearing it in a ratio of 1 normal individual to a plurality of homozygotic animal to the mother animal. By crossing a male and female of the heterozygotic animal, the homozygotic and heterozygotic animals having the inactivated DNA is propagated over generations.

The non-human mammal embryonic stem cell having ABP1 DNA inactivated is very useful in creating the DNA-expression-deficient non-human mammal of the present invention.

The DNA-expression-deficient non-human mammal of the resent invention is also useful in exploring the causes of these diseases and developing therapies therefor because it can serve as a model of a disease caused by inactivation of a biological activity of ABP1 due to lack of various biological activities inducible by ABP1.

(9a) Screening Method for a Compound having a Therapeutic or Prophylactic Effect on a Disease Caused by ABP1 DNA Deficiency, Damage or the Like The DNA-expression-deficient non-human mammal of the present invention can be used to screen for a compound having a therapeutic or prophylactic effect on a disease caused by ABP1 DNA deficiency, damage or the like, for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), inflammations (e.g., arthritis, nephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like) and the like.

Accordingly, the present invention provides a screening method for a compound having a therapeutic or prophylactic effect on a disease caused by ABP1 DNA deficiency, damage and the like, or a salt thereof, which comprises administering a test compound to the DNA-expression-deficient non-human mammal of the present invention, and examining and measuring the changes in the animal.

As the DNA-expression-deficient non-human mammal of the present invention used in the screening method, the same as those mentioned above can be mentioned.

As examples of the test compound, a peptide, a protein, a non-peptide compound, a synthetic compound, a fermentation product, a cell extract, a plant extract, an animal tissue extract, plasma and the like can be mentioned, and these compounds may be novel compounds or publicly known compound.

Specifically, the therapeutic or prophylactic effect of a test compound can be tested by treating the DNA-expression-deficient non-human mammal of the present invention with the test compound, and evaluating the changes in various organs, tissues, disease symptoms and the like in the test animal as indexes, in comparison with untreated control animals.

As examples of the method of treating the test animal with the test compound, oral administration, intravenous injection and the like can be used, and the appropriate method can be selected as appropriate for the test animal's symptoms, test compound nature and the like. Also, the dosage of the test compound can be appropriately selected according to method of administration, nature of the test compound, and the like.

In the screening method, when a test animal (for example, an animal with cancer and the like) is given a test compound, and, for example, if the test animal's symptoms have improved by about 10% or more, preferably about 30% or more, more preferably about 50% or more, the test compound can be selected as a compound that has a therapeutic or prophylactic effect on the above-described disease.

The compound obtained using the screening method is a compound selected from among the above-described test compounds, and can be used as a pharmaceutical such as a therapeutic or prophylactic agent and the like that is safe and of low toxicity for the above-described disease caused by ABP1 deficiency, damage and the like. Furthermore, a compound derived from a compound obtained by the above-described screening can also be used in the same manner.

The compound prepared by the screening method may have formed a salt; as the salt of the compound, a physiologically acceptable salt with an acid (e.g., inorganic acid, organic acid, and the like) or a base (e.g., alkali metal and the like) can be mentioned, with preference given to a physiologically acceptable acid addition salt. Useful salts include, for example, salts with inorganic acids (for example, hydrochloric acid, phosphoric acid, hydrobromic acid, sulfuric acid and the like) or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like.

A pharmaceutical containing the compound obtained by the screening method or a salt thereof can be produced and used in the same manner as the aforementioned pharmaceutical containing ABP1 or the activating peptide of the present invention.

(9b) Screening Method for Compound that Promotes or Inhibits the Promoter Activity on ABP1 DNA The present invention provides a screening method for a compound that promotes or inhibits the promoter activity on the ABP1 DNA, or a salt thereof, which comprises administering a test compound to an expression-deficient non-human mammal of the present invention, and detecting the expression of a reporter gene.

In the above-described screening method, as the DNA-expression-deficient non-human mammal of the present invention, one having ABP1 DNA inactivated by introduction of a reporter gene, which reporter gene is expressible under the control of a promoter for ABP1 DNA, out of the aforementioned DNA-expression-deficient non-human mammals of the present invention, can be used.

As the test compound, the same as those mentioned above can be mentioned.

As the reporter gene, the same as those mentioned above can be used, and the β-galactosidase gene (lacZ), the soluble alkaline phosphatase gene or the luciferase gene and the like are preferred.

In the DNA-expression-deficient non-human mammal of the present invention wherein ABP1 DNA is substituted by a reporter gene, the activity of the promoter can be detected by tracing the expression of the substance encoded by the reporter gene because the reporter gene is present under the control of the promoter of the ABP1 DNA.

For example, when a portion of the DNA region that encodes ABP1 has been replaced by the *Escherichia coli*-derived β-galactosidase gene (lacZ), β-galactosidase is expressed, in place of ABP1, in tissues where ABP1 is expressed originally. Therefore, the expression state of ABP1 can be conveniently confirmed by, for example, staining with a reagent that can serve as a substrate for β-galactosidase, like 5-bromo-4-chloro-3-indolyl-β-galactopyranoside (X-gal). Specifically, the expression state can be confirmed by fixing an ABP1-deficient mouse or a tissue section thereof with glutaraldehyde and the like, washing with phosphate-buffered saline (PBS), carrying out the reaction with a staining solution containing X-gal at room temperature or at nearly 37° C. for about 30 minutes to 1 hour, washing the tissue specimen with 1 mM EDTA/PBS solution to stop the β-galactosidase reaction, and examining the color developed. Also, the mRNA that encodes lacZ may be detected according to a conventional method.

A compound obtained using the above-described screening method or a salt thereof is a compound selected from among the above-described test compounds, that promotes or inhibits the promoter activity for ABP1 DNA.

The compound obtained by the screening method may have formed a salt, and as the salt of the compound, physiologically acceptable salts with acids (e.g., inorganic acids and the like), bases (e.g., organic acids and the like) and the like can be mentioned, and physiologically acceptable acid addition salts are preferred. Useful salts include, for example, salts with inorganic acids (for example, hydrochloric acid, phosphoric acid, hydrobromic acid, sulfuric acid, and the like) or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid, and the like) and the like.

Because a compound that promotes the promoter activity against ABP1 DNA or a salt thereof is capable of promoting the expression of ABP1 and of promoting the function of ABP1, it can be used as a pharmaceutical such as a prophylactic or therapeutic agent for, for example, a disease associated with functional impairment of ABP1. Specifically, the compound can be used as a safe pharmaceutical of low toxicity such as a prophylactic or therapeutic agent for, for example, cancers (e.g., leukemia, esophageal cancer, gastric cancer, colon cancer, rectal cancer, lung cancer, liver cancer, kidney cancer, breast cancer, uterine cancer, ovarian cancer, prostatic cancer, melanoma, myeloma, osteosarcoma, brain tumor and the like), autoimmune diseases (e.g., systemic lupus erythematosus, scleroderma, rheumatoid arthritis, Sjogren's syndrome, multiple sclerosis, insulin-dependent diabetes, psoriasis, ulcerative colitis, idiopathic thrombocytopenic purpura, Crohn's disease, glomerulonephritis and the like), viral infections (e.g., hemorrhagic fever, T-cell leukemia, Kaposi sarcoma, infectious mononucleosis, lymphoma, epipharyngeal cancer, cervical cancer, skin cancer, hepatitis, liver cancer and the like), endocrine diseases (e.g., hyperhormonal disease, hypercytokine disease and the like), hematological diseases (e.g., hemocytosis, B-cell lymphoma, polycythemia and the like), organ hyperplasia (e.g., hermaphroditism, undescended testis, teratoma, nephroblastoma, polycystic kidney, cardiac/aortic malformations, syndactyly and the like), post-angioplastic restenosis, recurrence after cancer resection and the like.

On the other hand, because a compound that inhibits the promoter activity against ABP1 DNA or a salt thereof is capable of inhibiting the expression of ABP1 and of inhibiting the function of ABP1, it is useful as a pharmaceutical such as a prophylactic or therapeutic agent for, for example, a disease associated with ABP1 overexpression and the like. Specifically, the compound can be used as a safe pharmaceutical of low toxicity such as a prophylactic or therapeutic agent for a disease, for example, viral infections (e.g., AIDS, influenza, fever of unknown origin and the like), endocrine diseases (e.g., hormone deficiency, cytokine deficiency and the like), hematological diseases (e.g., hemocytopenia, renal anemia and the like), organ hypoplasia (e.g., thyroid atrophy, cleft palate and the like), organ graft rejection, graft-versus-host disease, immune deficiency, neurodegenerative diseases (e.g., polyglutamine disease, Alzheimer's disease, Parkinson's disease, amyotrophic lateral sclerosis, prion disease, cerebellar degeneration and the like), ischemic heart diseases (e.g., angina pectoris, myocardial infarction and the like), radiation injuries, ultraviolet injuries (e.g., sunburns and the like), poisoning diseases (e.g., renal tubular cell injury by heavy metals, liver cell injury by alcohol, and the like), nutritional disorders (e.g., thymus atrophy due to vitamin or trace element deficiency, and the like), inflammatory diseases (e.g., acute pancreatitis, arthritis, periodontal disease, colitis and the like), ischemic neuropathy, diabetic neuropathy, vascular diseases (e.g., arteriosclerosis and the like), respiratory diseases (e.g., interstitial pneumonia, pulmonary fibrosis and the like), articular diseases (e.g., arthritic deformans and the like) and the like.

Furthermore, a compound derived from a compound obtained by the above-described screening can also be used in the same manner.

A pharmaceutical containing a compound obtained by the screening method or a salt thereof can be produced and used in the same manner as the aforementioned pharmaceutical containing ABP1 or the activating peptide of the present invention.

As described above, the DNA-expression-deficient non-human mammal of the present invention is very useful in screening for a compound that promotes or inhibits the promoter activity for ABP1 DNA or a salt thereof, thus contributing significantly to the elucidation the causes of various diseases due to ABP1 DNA expression deficiency, and the development of prophylactic or therapeutic drugs for the same.

Additionally, provided that genes that encode various proteins are joined downstream of the promoter region of the ABP1 gene contained in DNA, and the DNA is injected to an animal ovum to prepare what is called a transgenic animal (gene transferred animal), it is possible to allow the animal to tissue- and/or time-specifically synthesize the protein, and investigate its action in the body. Furthermore, provided that the above-described promoter portion is bound with an appropriate reporter gene, and a cell line that allows its expression is established, the cell line can be used as a screening system for a low-molecular compound that acts to specifically promote or suppress the producibility of ABP1 itself in the body.

Abbreviations for bases, amino acids and the like used in the present specification and drawings are based on abbreviations specified by the IUPAC-IUB Commission on Biochemical Nomenclature or abbreviations in common use in relevant fields. Some examples are given below. When an enantiomer may be present in amino acid, it is of the L-configuration, unless otherwise stated.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid
*: Corresponds to stop codon.
Me: Methyl group
Et: Ethyl group
Bu: Butyl group
Ph: Phenyl group
TC: Thiazolidine-4(R)-carboxamide group Substituents, protecting groups and reagents frequently mentioned herein are represented by the symbols shown below.

Tos: p-Toluenesulfonyl
CHO: Formyl
Bzl: Benzyl
Cl$_2$Bzl: 2,6-Dichlorobenzyl
Bom: Benzyloxymethyl
Z: Benzyloxycarbonyl
Cl-Z: 2-Chlorobenzyloxycarbonyl
Br-Z: 2-Bromobenzyloxycarbonyl
Boc: t-Butoxycarbonyl
DNP: Dinitrophenol
Trt: Trityl
Bum: t-Butoxymethyl
Fmoc: N-9-Fluorenylmethoxycarbonyl
HOBt: 1-Hydroxybenztriazole
HOOBt: 3,4-Dihydro-3-hydroxy-4-oxo-1,2,3-benzotriazine
HONB: 1-Hydroxy-5-norbornane-2,3-dicarboximide
DCC: N,N'-Dicyclohexylcarbodiimide The sequence identification numbers in the sequence listing herein show the following sequences.

[SEQ ID NO:1]
Shows the base sequence of the amino acid-encoding region of human ABP1 cDNA.
[SEQ ID NO:2]
Shows the amino acid sequence of human ABP1.
[SEQ ID NO:3]
Shows the base sequence of the amino acid-encoding region of mouse ABP1 cDNA.
[SEQ ID NO:4]
Shows the amino acid sequence of mouse ABP1.
[SEQ ID NO:5]
Shows the amino acid sequence of the peptide used as the antigen for preparation of an anti-ABP1 antibody (ELA antibody).
[SEQ ID NO:6]
Shows the amino acid sequence of the peptide used as the antigen for preparation of an anti-ABP1 antibody (LVR antibody).

The present invention is hereinafter described in more detail by means of the following Examples, which examples, however, are not to be construed as limiting the scope of the present invention.

EXAMPLE 1

Cloning of ABP1 cDNA

To identify the ASK1-binding protein, screening was conducted by the yeast two-hybrid method using Brent's system [Zervos et al., Cell, Vol. 72, p. 223-232, 1993; Gyuris et al., Cell, Vol. 75, p. 791-803, 1993] with ASK1-KR, prepared by replacing lysine (K) at the ATP-binding site (position 709) in the kinase domain of human ASK1 with arginine (R), as a bait and an expression library of fetal human brain origin as a prey. As a result, about 1200 positive clones were obtained. Database search of one of them based on its base sequence identified it as a portion of the protein coding region of the gene designated as "PGR1" (a portion corresponding to amino acid positions 35 to 127). The protein encoded by this gene consists of 127 amino acids, but information on the database was only relevant to the structure of the gene, and did not contain a report on its function. Hence, the full-length cDNA that encodes the protein of this gene was cloned by the PCR method. Since this protein was identified as an ASK1-binding protein, it was designated as ASK1 binding protein 1 (ABP1). Although homology search revealed the presence of similar molecules of ABP1 in mammals such as the mouse, no highly homologous molecules were found in the fly, nematode or the like. Additionally, motif search and domain search did not reveal any existing motif, function domain or the like. FIG. 1 shows the alignments of the human and mouse ABP1 amino acid sequences.

EXAMPLE 2

Expression Distribution of ABP1 mRNA

Using Mouse (#7762-1) and Mouse Embryo (#7763-1) in the Multiple Tissue Northern Blot (CLONTECH) with the full-length human ABP1 cDNA as a probe, Northern blot was conducted as directed in the instruction manual of the above-described product. As a result, the length of the ABP1 mRNA was determined to be about 1.7 kb, and the mRNA was ubiquitously expressed throughout all tissues (FIG. 2A). Fetal mouse blot also revealed the expression of ABP1 mRNA from relatively early time of E7 days, with no major changes during the course of embryogenesis (FIG. 2B).

EXAMPLE 3

Production of ABP1 Protein in Various Animal Cells

Next, a rabbit polyclonal antibody against ABP1 was prepared. Two kinds of peptide antibodies were prepared with ABP1-specific peptide (SEQ ID NO:5 and SEQ ID NO:6) as antigens on the basis of amino acid sequence information from the base sequence of the ABP1 cDNA, and were designated as ELA antibody and LVR antibody, respectively. The two antibodies were both used after being purified on the basis of affinity for antigen peptide.

HeLa cells and HEK293 cells were cultivated in the presence of 5% CO$_2$ using Dulbecco's modified Eagle medium. (DMEM; SIGMA) containing a high concentration of glucose (4.5 mg/ml) as a culture medium. The culture medium was supplemented with 10% fetal bovine serum (FBS) and 100 Units/ml penicillin. Porcine aortic endothelial (PAE) cells were cultivated using an F12 culture medium (Invitrogen) supplemented with 10% FBS, 10 mM HEPES, and 100 Units/ml penicillin.

Each cell was lysed using a lysis buffer [150 mM NaCl, 20 mM Tris-HCl (pH 7.5), 10 mM EDTA, 1% Triton X-100, 1% deoxycholate, 1.5% aprotinin, 1 mM PMSF], the lysate was centrifuged, the supernatant was recovered, a SDS sample buffer [100 mM Tris-HCl (pH 8.8), 0.01% bromophenol blue, 36% glycerol, 4% SDS] was added, and SDS polyacrylamide gel electrophoresis (SDS-PAGE) was conducted. The protein was transferred from the gel to a PVDF membrane, and blocking was conducted with TBS-T [150 mM NaCl, 50 mM Tris-HCl, (pH 8.0), 0.05% Tween 20] containing 5% skimmed milk at room temperature for 3 hours, and the protein was reacted with each antibody. Detection was conducted using the ECL system (Amersham Pharmacia Biotech).

When a cell culture extract of HEK293 cells was subjected to immunoblot analysis using the ELA antibody and the LVR antibody, band identified with the two antibodies appeared at about 17 kDa. The position at which this band was detected showed a complete agreement between the two antibodies. Also, HEK293 cells were transfected with a plasmid that expresses untagged ABP1 [prepared by subcloning ABP1 cDNA obtained by PCR into pcDNA3 (Invitrogen, Inc.)] [conducted using FuGENE6 (Roche Diagnostics K.K) as directed in the instruction manual thereof] to allow the overexpression of the ABP1 protein; detection intensity increased plasmid-content-dependently (FIG. 3). When peptide block was conducted by adding an antigen peptide at the time of primary antibody treatment, this band disappeared.

This demonstrates that these antibodies recognized ABP1 and could detect the endogenous ABP1 protein. Similar results were obtained with HeLa cells and PAE cells.

EXAMPLE 4

Intracellular Interaction of ABP1 and ASK1

Figure 4A:
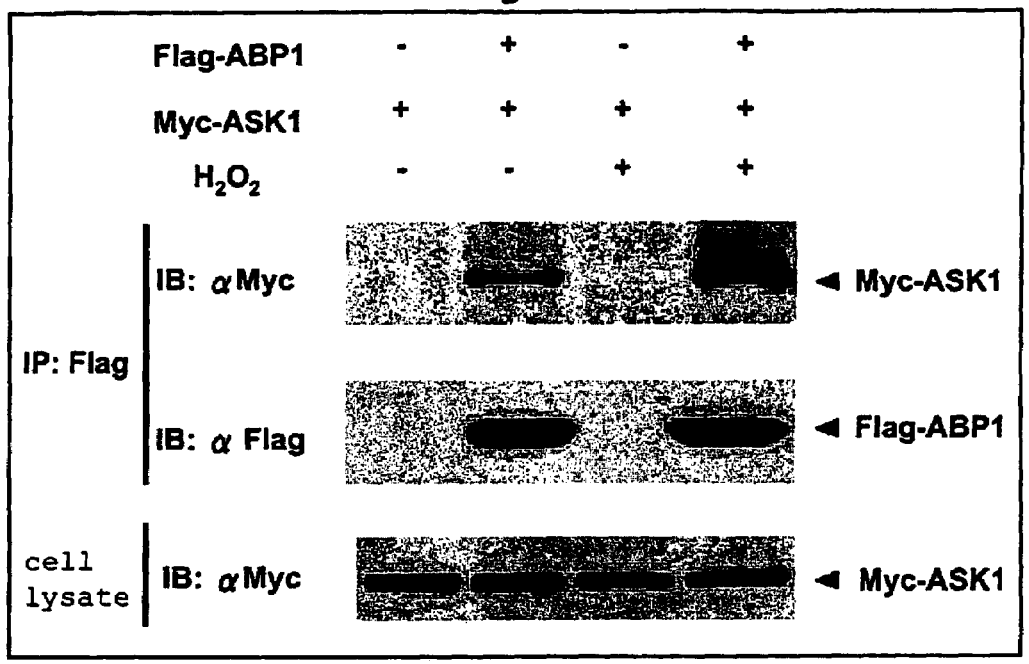
FIGS. 4A-B show the results of binding experiments of ABP1 and ASK1.
Figure 4B:
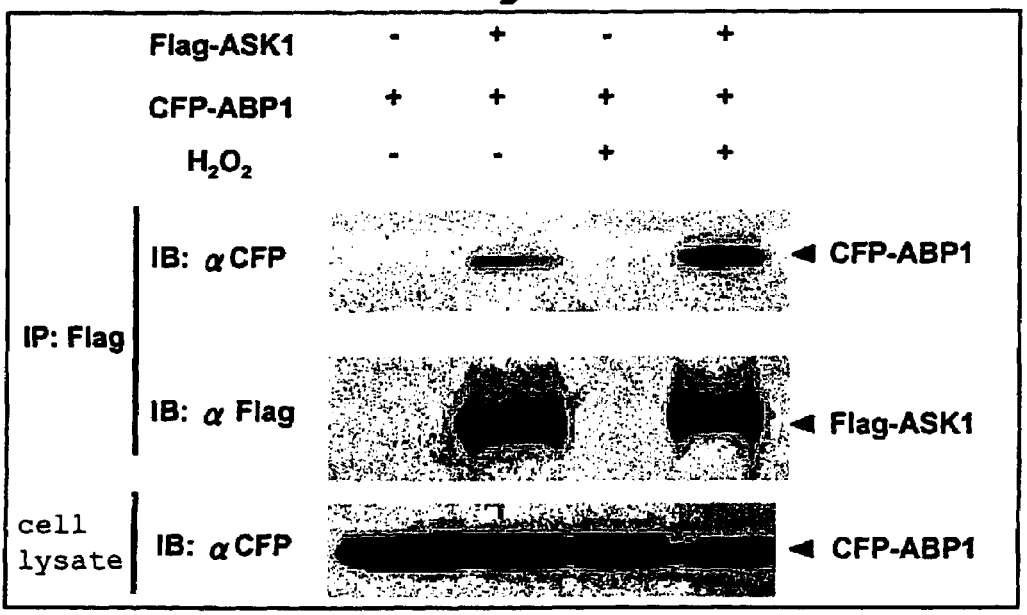

Two fusion proteins, i.e., Flag-ABP1 and Myc-ASK1, were co-expressed in HEK293 cells. The cells were lysed using a lysis buffer (described above), the lysate was centrifuged, the supernatant was recovered and reacted with an anti-Flag antibody (Clone M2; SIGMA), Protein A-sepharose 4B (Zymed Laboratories) was added, incubation was conducted for 30 minutes, the reaction mixture was washed with the lysis buffer three times, an SDS sample buffer (described above) was added, and the same procedure as the immunoblotting method was followed to confirm the binding of the two proteins (FIG. 4A). The antibodies used were anti-Flag antibody (described above) and anti-Myc antibody (Clone 9E10, Calbiochem). This binding was enhanced by treatment with $H_2O_2$, which is ASK1 activation factor. Next, HEK293 cells were allowed to co-express CFP-ABP1 and the Myc-ASK1 plasmid in the same manner, and immunoprecipitation with an anti-Flag antibody was conducted; the binding of the two proteins was confirmed (FIG. 4B). The antibodies used were anti-Flag antibody (described above) and anti-GFP antibody (Medical & Biological Laboratories CO.). This binding was also enhanced by $H_2O_2$ treatment. From this finding, it was found that ABP1 and ASK1 bind to each other even in mammalian cells, and that this binding is enhanced by $H_2O_2$ treatment.

EXAMPLE 5

Identification of Binding Site of ASK1 to ABP1

Figure 5A:
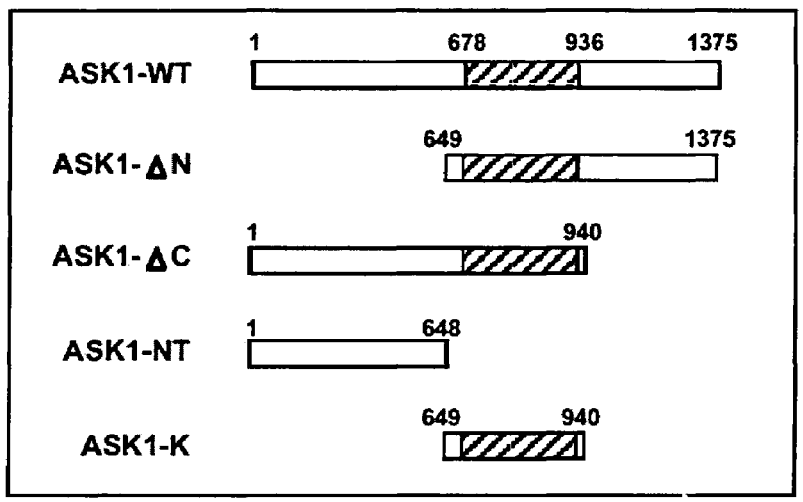
FIG. 5A shows a schematic diagram of an ASK1-deficient variant. Each plasmid containing the ASK1-deficient variant had an HA tag added to the N-terminal side thereof. Amino acid numbers 678 to 936 (diagonal portion) indicate a kinase domain.
Figure 5B:
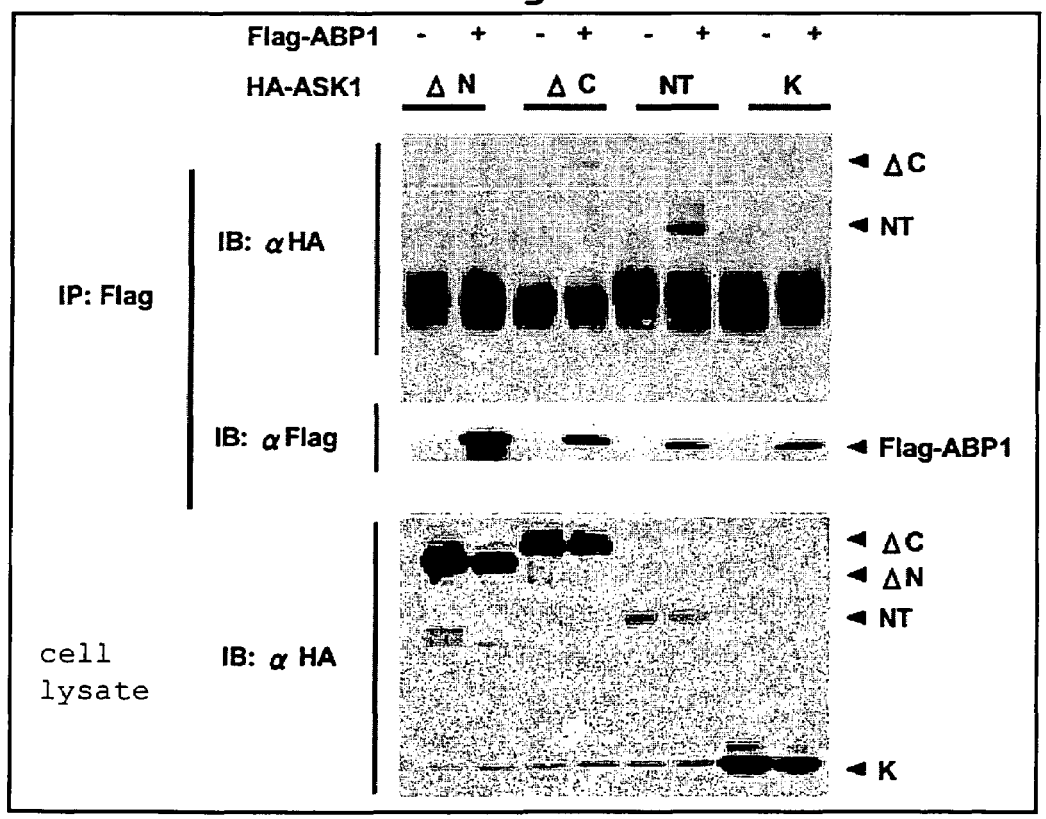
FIG. 5B shows the results of a binding experiment of ABP1 and the ASK1-deficient variant. The lower panel shows the results of a separate electrophoresis of a portion of each cell lysate before immunoprecipitation. IP stands for immunoprecipitation, and IB stands for immunoblot.

The binding of the various ASK1-deficient variants with the HA tag shown in FIG. 5A and ABP1 was examined by the immunoprecipitation method using an anti-Flag antibody after co-expression with Flag-ABP1 as in Example 3. The antibodies used were anti-HA antibody (Clone 3F10, Roche Diagnostics K.K) and anti-Flag antibody (Clone M2, SIGMA). The ASK1 expression vector used was one described by Saitoh et al. (ibidem). As a result, ABP1 co-precipitated with ASK1-NT and ASK1-ΔC but did not co-precipitate with ASK1-AN and ASK1-K (FIG. 5B). This demonstrated that ABP1 binds to the N-terminal domain of ASK1.

EXAMPLE 6

Cell Death Induced by ABP1

(1) To examine the intracellular localization and function of ABP1, HeLa cells were transfected with the CFP-ABP1 plasmid [prepared by subcloning ABP1 cDNA prepared by PCR into pECFP-C1 (Clontech)], which was also used in the immunoprecipitation experiment, and which expresses a fusion protein of ABP1 with CFP at the N-terminal- [transfection conducted using FuGENE6 (Roche Diagnostics K.K) as directed in the instruction manual thereof] to allow the transient expression of the protein, and CFP fluorescence was examined over time using a fluorescence microscope. Under a fluorescence microscope, the ratio of those cells that detached from the plate or showed morphological changes suggestive of cell death, such as membrane blebbing and fragmentation, to the cells showing CFP fluorescence (500 cells), was calculated. This calculation was made for CFP-positive cells.

Figure 6A:
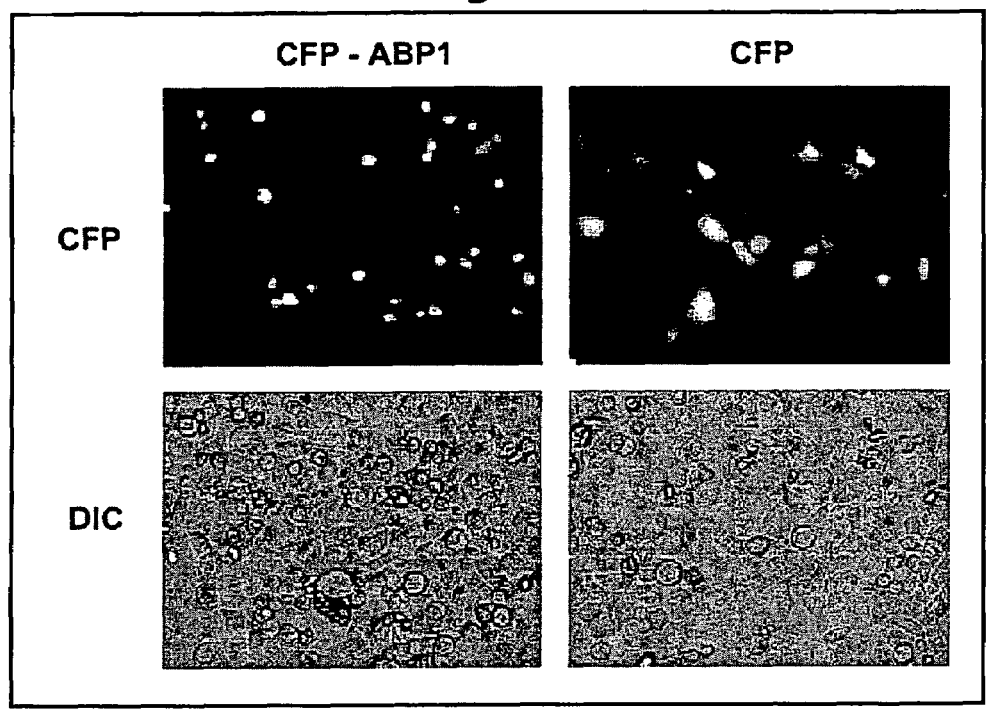
FIGS. 6A-B show the induction of cell death by ABP1 in HeLa cells.
Figure 6B:
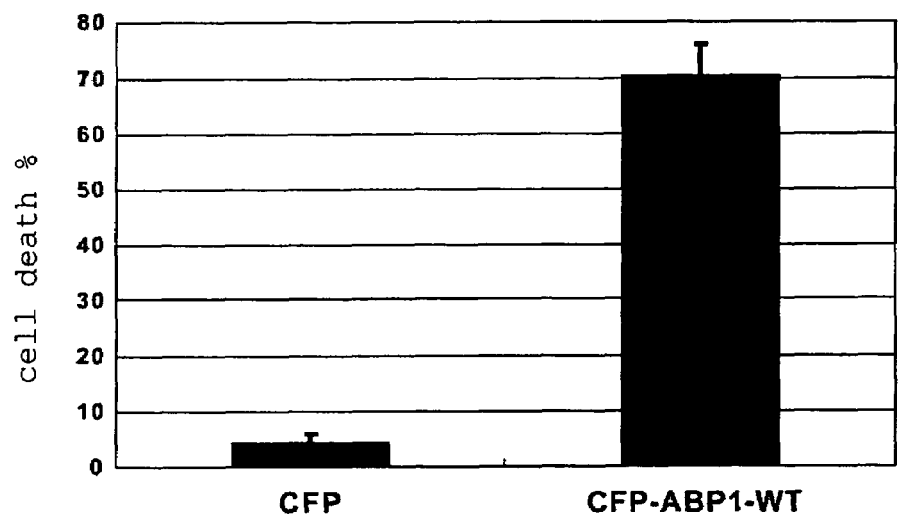

As a result, the fluorescence from the CFP-ABP1 fusion protein was distributed throughout the cell, including both cytoplasm and nucleus, as in the case wherein the CFP protein alone was expressed. Continued observations revealed the cells expressing the CFP-ABP1 fusion protein from around 24 hours after transfection began showing signs of cell death such as detachment from the culture plate, membrane blebbing, and the like (FIG. 6A). Quantitation of this cell death showed that as many as about 70% of the cells expressing the CFP-ABP1 fusion protein underwent cell death at 36 hours after transfection (FIG. 6B). This phenomenon was not observed when the CFP protein was expressed alone. Also, similar intracellular localization and cell death induction were observed when a protein having CFP fused to the C terminal of ABP1 was expressed.

From this finding, ABP1 was considered to be a protein having a potential for cell death induction.

(2) To elucidate the mechanism of cell death by ABP1, a cell line capable of inducing the tetracycline-dependent expression of ABP1 in PAE cells (PAE-ABP1 cells) was established. PAE-ABP1 cells were prepared using the method of Takeda et al. (J. Biol. Chem., 275, 9805-9813, 2000) with a partial modification. The full-length ABP1 cDNA with the Myc tag was subcloned into the pTet-Splice-neo vector, this and the pTet-tTAk-hyg plasmid were transfected to PAE cells simultaneously, unlike the method of Takeda et al., the cells were cultivated for selection in a culture medium containing 500 ng/ml tetracycline (Sigma), 400 Units/ml hygromycin B (Wako), and 240 mg/ml neomycin (Geneticin, Life Technologies, Inc.), and the cells that survived and colonized were designated as PAE-ABP1 cells. Maintenance cultivation of the cells were conducted using the aforementioned culture medium for PAE cell maintenance with the addition of 500 ng/ml tetracycline, 200 Units/ml hygromycin B and 30 mg/ml neomycin.

Figure 7A:
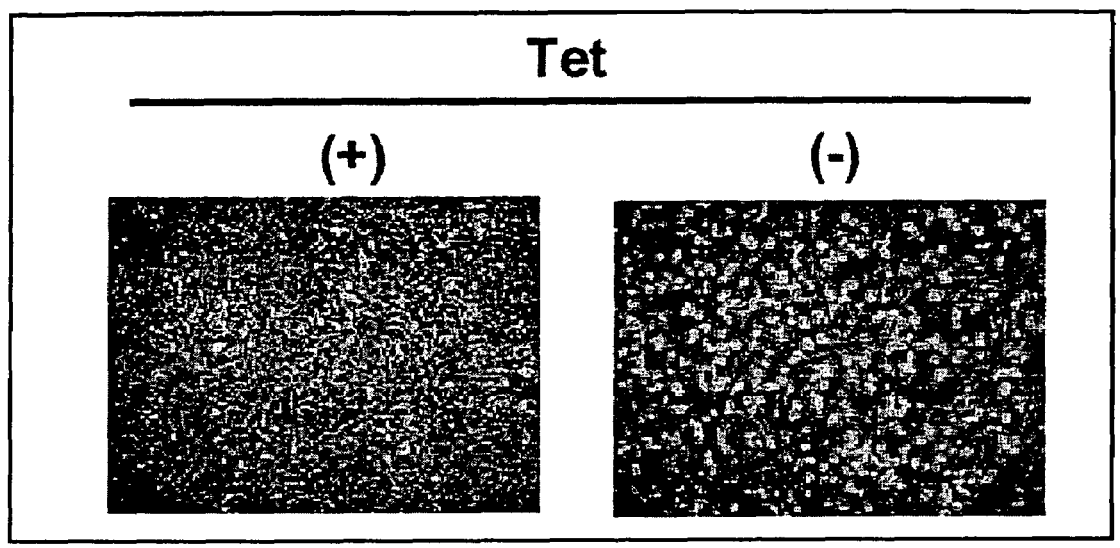
FIGS. 7A-B show the induction of cell death by ABP1 in PAE-ABP1 cells.
Figure 7B:
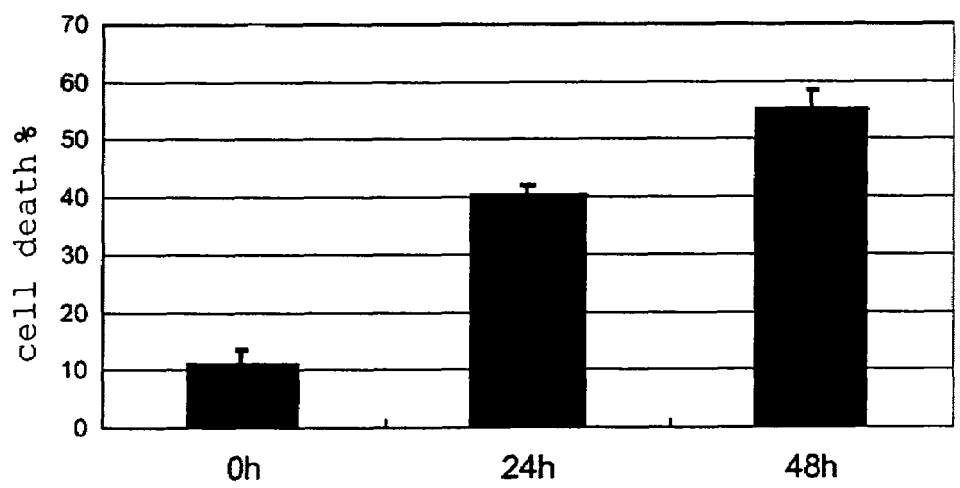

These PAE-ABP1 cells did not express ABP1 when cultivated in the presence of tetracycline, but when they were cultivated in the absence of tetracycline, the expression of the ABP1 protein with Myc-tag became evident about 6 hours later, as confirmed by immunoblot analysis, after which stable expression of ABP1 was observed. When immunostaining with an anti-Myc antibody (Clone 9E10, Calbiochem) was conducted, almost all cells showed stable expression of Myc-ABP1. When these cells were cultured in the absence of tetracycline, cell death was induced with the expression of the ABP1 protein, as in the transient expression of the ABP1 protein in HeLa cells (FIG. 7A). The ratio of dead cells to all cells (the ratio of cells showing a morphological sign of cell death to all cells was determined under a microscope; the results were shown as the mean for three visual fields) was determined to be about 55% at 48 hours after removal of tetracycline (FIG. 7B). In this experimental system as well, ABP1 was confirmed as inducing cell death.

(3) Morphological changes suggestive of cell death induced by the ABP1 of (1) and (2) above, such as membrane blebbing and cell fragmentation, are often observed during apoptosis. Hence, whether the cell death in PAE-ABP1 cells represents apoptosis was determined by the presence or absence of DNA fragmentation.

PAE-ABP1 cells ($2\times10^6$ cells) were lysed in 200 µl of lysis buffer [20 mM Tris-HCl (pH 7.5), 10 mM EDTA, 0.5% Triton X-100]. the lysate was centrifuged, and the supernatant was recovered and treated with 0.2 mg/mi proteinase K at 420° C for 1 hour. Subsequently, DNA was purified by the phenol-chloroform extraction method and the ethanol precipitation method, this was lysed again in a TE buffer containing 0.2 mg/ml ribonuclease A (10mM Tris-HCl, 1mM EDTA), the lysate was electrophoresed on 2% agarose gel, stained with ethidium bromide, and the migration pattern was photographed.

Figure 8:
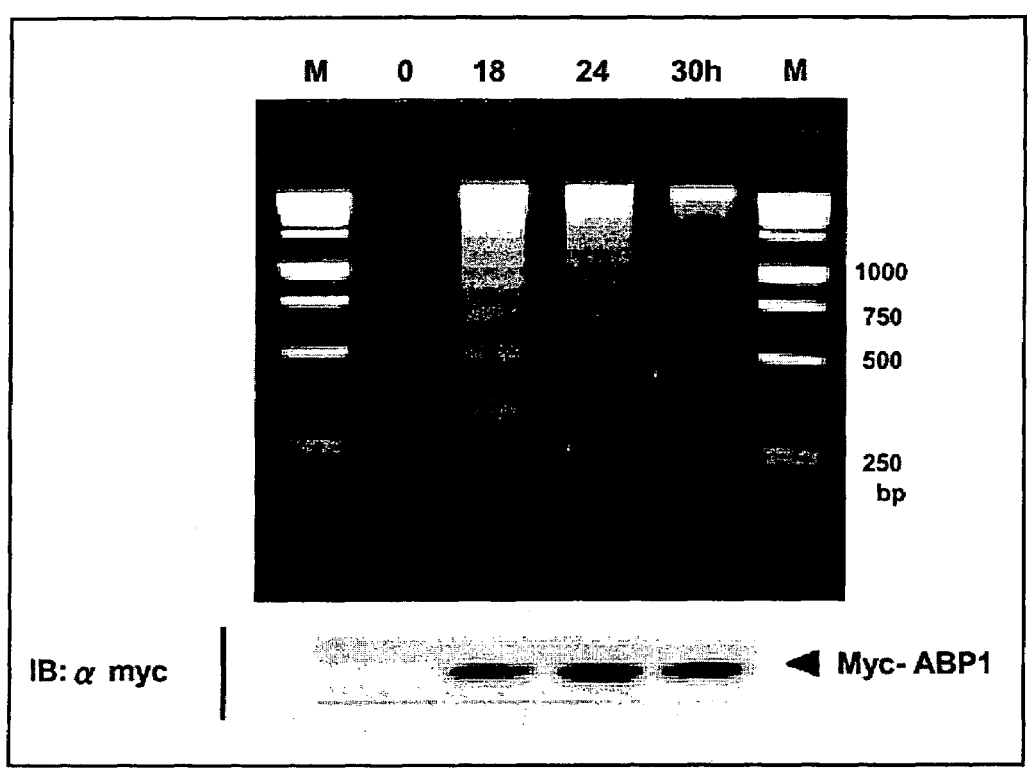
FIG. 8 shows the induction of cell death (DNA fragmentation) by ABP1 in PAE-ABP1 cells. PAE-ABP1 cells were examined for DNA fragmentation at each time after removal of tetracycline by agarose gel electrophoresis (upper panel). At both ends are molecular weight markers (M), with their sizes shown at the right end. The lower panel shows the results of a confirmation of the expression of the Myc-ABP1 protein in each cell by immunoblot analysis using an anti-Myc antibody.

As a result, PAE-ABP1 cells formed a DNA ladder with the expression of the ABP1 protein, in synchronization with the timing of the onset of cell death observed using a microscope (FIG. 8). This fact demonstrated that the cell death caused by ABP1 is what is called apoptosis accompanied by DNA fragmentation. The same was also confirmed in TUNEL staining of PAE-ABP1 cells.

(4) DNA fragmentation during apoptosis normally occurs subsequent to caspase activation. Hence, using PAE-ABP1 cells, a measurement of caspase-3 activity was conducted at the time of induction of expression of the ABP1 protein. The measurement was conducted using a CPP32/caspase-3 fluorometric protease assay kit (MBL) with the synthetic fluorescence peptide DEVD-7-amino-4-trifluoromethyl coumarin (AFC) as a substrate. The fluorescence intensity from the liberated AFC was measured at an excitation wavelength of 360 nm and a fluorescence wavelength of 530 nm using a fluorescence spectrophotometer. Each sample was assayed twice. The results are shown as relative values with the value in the presence of tetracycline taken as 1.

Figure 9A:
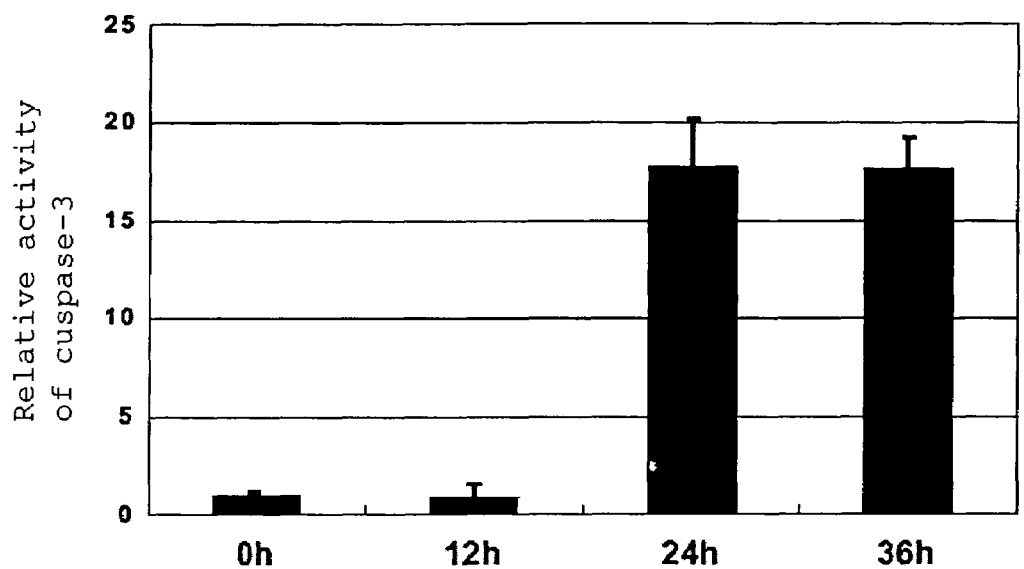
FIGS. 9A-B show the caspase dependency of cell death by ABP1.
Figure 9B:
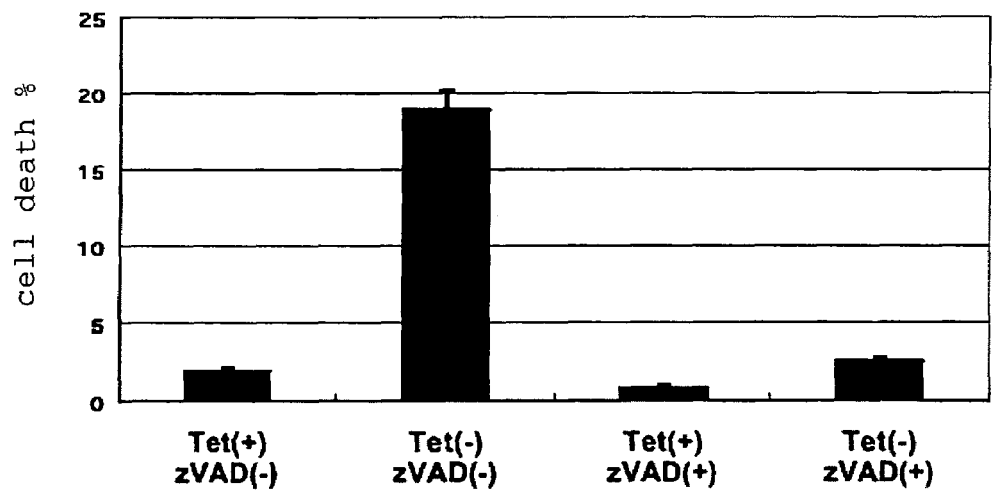

As a result, caspase-3 activity decreased around the time of cell death (FIG. 9A). To determine whether the cell death caused by ABP1 is caspase-dependent, PAE-ABP1 cells were treated with the caspase inhibitor zVAD-fmk (Peptide Institute, Inc.) simultaneously with tetracycline removal; cell death was almost completely suppressed early at 18 hours after tetracycline removal (FIG. 9B). This led to the conclusion that the cell death caused by ABP1 was a caspase-dependent apoptosis.

EXAMPLE 7

Identification of Cell Death Induction Region of ABP1

Figure 10A:
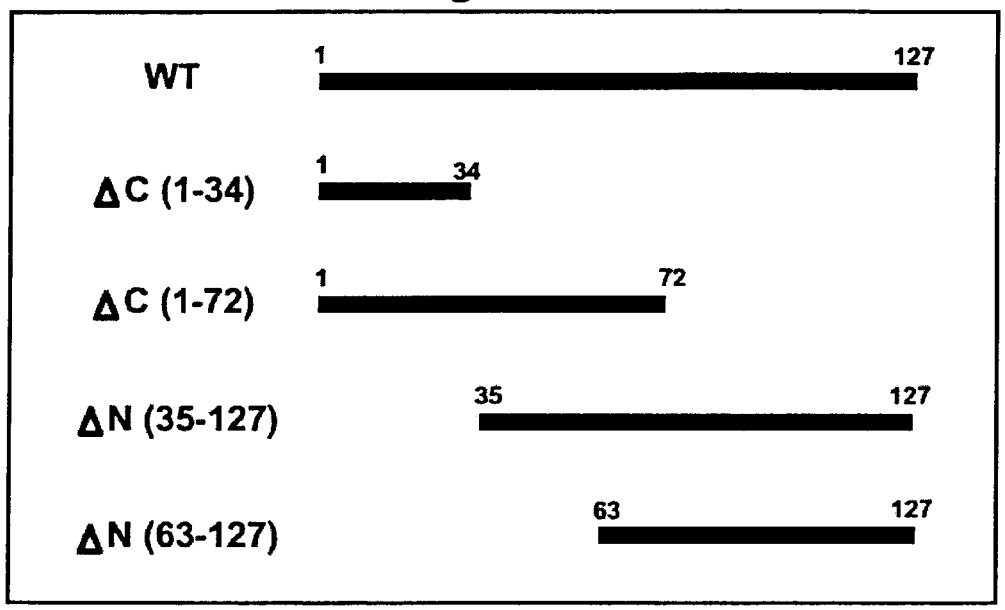
FIGS. 10A-B show the induction of cell death by an ABP1-deficient variant.

As described above, ABP1 has none of the functional domains of existing apoptosis-related factors. Hence, to identify a domain necessary for apoptosis by ABP1, plasmids that express fusion proteins of the various ABP1-deficient variants shown in FIG. 10A and CFP were prepared, and HeLa cells were allowed to express these proteins in the same manner as Example 6(1) and examined for cell death. ABP1 expression vectors were prepared by subcloning an ABP1 cDNA or ABP1-deficient variant DNA prepared by PCR into pECFP-C1 (Clontech). Transfection of the cells with each plasmid was conducted using FuGENE6 (Roche Diagnostics K.K) as directed in the instruction manual thereof.

Figure 10B:
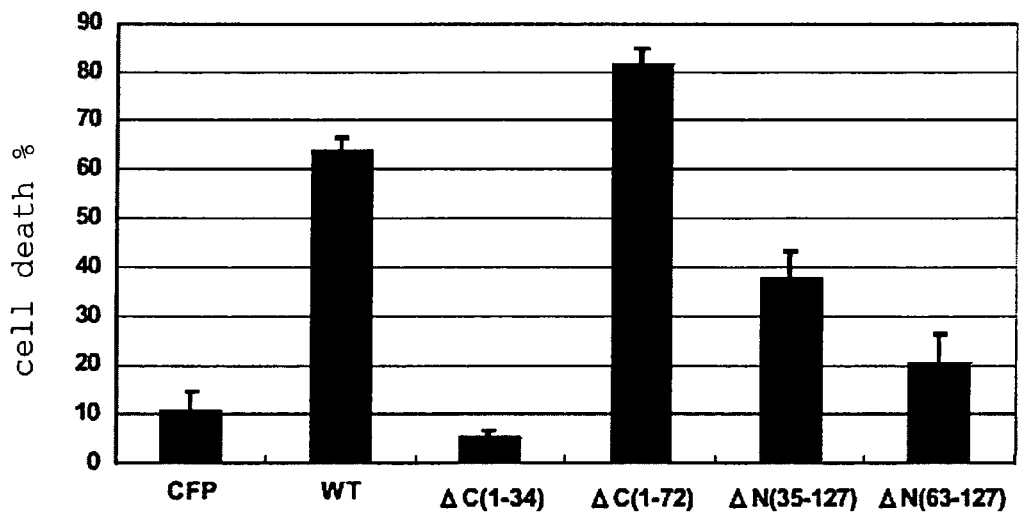

As a result, $\Delta C(1-72)$ exhibited a greater potential for cell death induction than the wild type, but the potential for cell death induction decreased in the order of $\Delta N(34-127)$ and $\Delta N(65-127)$ as an increasing number of amino acids were deleted from the N-terminal, (FIG. 10B). From this finding, it was considered that the N-terminal side of ABP1 is important to the potential for cell death induction.

EXAMPLE 8

Effect of ABP1 on the ASK1 Signal Transduction System

The activation of JNK and p38 during induction of the expression of ABP1 was investigated using respective anti-phosphorylated protein antibodies using PAE-ABP1 cells. The antibodies used were an anti-phosphorylated JNK antibody (Cell Signaling), an anti-phosphorylated p38 antibody (Cell Signaling), and an anti-phosphorylated ASK1 antibody (Tobiume et al., EMBO Rep., 2, 222-228, 2001). The cells were lysed using a lysis buffer (described above) in the same manner as Example 4, the lysate was centrifuged, the supernatant was recovered and reacted with an anti-Myc antibody (Clone 9E10, Calbiochem), Protein A-sepharose 4B (Zymed Laboratories) was added, incubation was conducted for 30 minutes, the reaction mixture was washed with the lysis buffer three times, an SDS sample buffer (described above) was added, and the same procedure as the immunoblotting method was followed.

Figure 11A:
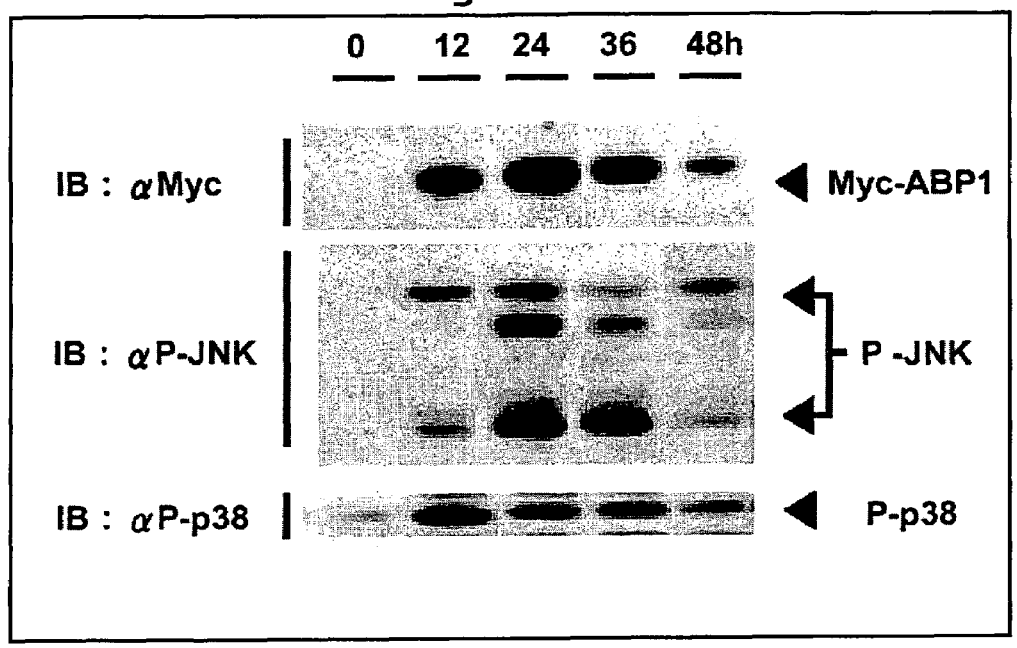
FIGS. 11A-B show the activation of ASK1, JNK, and p38 by ABP1.
Figure 11B:
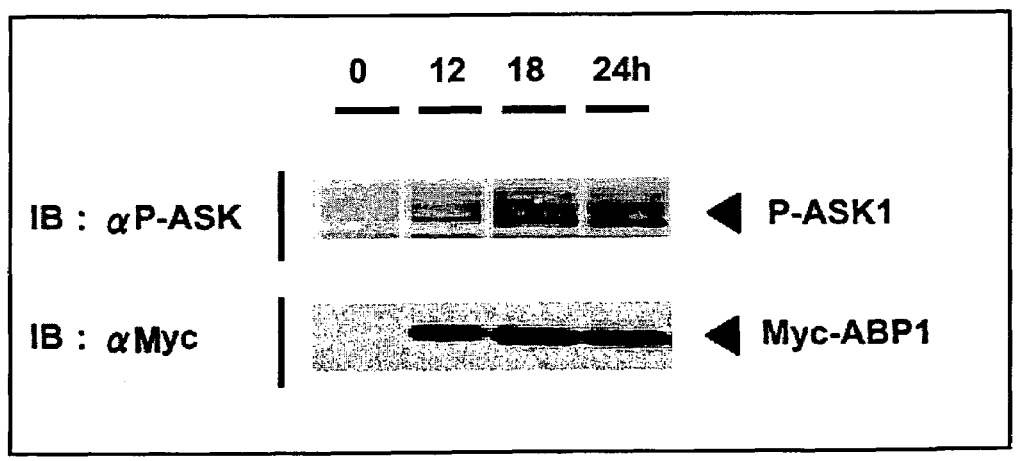

When tetracycline was removed, the activation of JNK and p38 was observed 12 hours later, in advance of the remarkable cell death associated with the expression of the ABP1 protein, and this persisted thereafter (FIG. 11A). Then, the activation of ASK1 was investigated also using PAE-ABP1 cells; the activation of ASK1 was observed at 12 hours after tetracycline was removed, as with JNK and p38 (FIG. 11B). From this finding, it was considered that the ASK1 signal transduction system is activated by the overexpression of ABP1.

INDUSTRIAL APPLICABILITY

The ABP1 of the present invention acts to activate the ASK1 cascade to induce apoptosis to cells, and to induce the production of inflammatory cytokines. Therefore, the ABP1 of the present invention, a polynucleotide that encodes the same, and the like are useful as prophylactic or therapeutic agents for diseases in which induction of apoptosis to cells is expected to have a prophylactic or therapeutic effect thereon. On the other hand, because the agent for suppressing ABP1 according to the present invention (for example, anti-ABP1 antibody, ABP1 antisense polynucleotide and the like) suppresses apoptosis and inflammatory cytokine production, it is useful as a prophylactic or therapeutic agent for diseases in which suppression of apoptosis is expected to have a prophylactic or therapeutic effect thereon, or for inflammatory diseases. Furthermore, using the ABP1 and ASK1 of the present invention provides a screening means for a new prophylactic or therapeutic drug for diseases associated with apoptosis or inflammation.

What is claimed is:

1. A method for identifying a substance which regulates ASK1 activation, the method comprising
   (1) contacting an ASK1 polypeptide or a partial peptide thereof containing an ASK1 N-terminal activation control domain or a salt thereof with a polypeptide comprising SEQ ID NO:2 or a partial peptide or salt thereof, wherein said polypeptide or partial peptide or salt thereof is capable of binding to and activating said ASK1 polypeptide; and
   (2) measuring the binding of said ASK1 polypeptide or partial peptide thereof to said polypeptide comprising SEQ ID NO:2 or a partial peptide or salt thereof in the presence or absence of a test substance; wherein an alteration in said binding identifies the test substance as a substance that regulates ASK1 activation.

2. The method of claim 1, wherein the ASK1 polypeptide or the polypeptide comprising SEQ ID NO:2 or a partial peptide or salt thereof is expressed in a cell.

3. The method of claim 1, further comprising the step of selecting the test substance.

4. The method of claim 1, wherein said polypeptide comprising SEQ ID NO:2 or a partial peptide or salt thereof is expressed in a cell.

5. The method of claim 4, wherein the cell that produces said ASK1 polypeptide, partial peptide thereof, or salt thereof also expresses said polypeptide comprising SEQ ID NO:2 or a partial peptide or salt thereof.

6. A method for identifying a substance which regulates ASK1 activation, comprising:
   (1) contacting a cell that expresses an ASK1 polypeptide or a partial peptide thereof containing an ASK1 N-terminal activation control domain and an ASK1 kinase domain or a salt thereof with a polypeptide comprising SEQ ID NO:2 or a partial peptide thereof, wherein said polypeptide or partial peptide thereof is capable of binding to and activating ASK1;
   (2) measuring the activity of the ASK1 polypeptide or partial peptide thereof in the presence or the absence of a test substance, wherein an alteration in said activity identifies the test substance as a substance that regulates ASK1 activation.

7. A method of identifying a substance which regulates ASK1 activation, comprising:
   (1) contacting a cell that produces a polypeptide comprising SEQ ID NO:2 or a partial peptide or salt thereof, wherein said polypeptide is capable of binding to and activating ASK1 with a test substance; and
   (2) measuring the expression of said polypeptide or partial peptide thereof, or of an mRNA encoding said polypeptide or partial peptide thereof, wherein an alteration in said expression identifies the test substance as a substance that regulates ASK1 activation.

8. The method of claim 7, wherein said expression is measured using an antibody that specifically binds to said polypeptide comprising SEQ ID NO:2 or partial peptide thereof.

9. The method of claim 7, wherein said expression is measured by hybridizing a polynucleotide that is complementary to said mRNA.

10. The method of claim 9, wherein said measuring step further comprises an amplification step, wherein said hybridizing complementary polynucleotide is used as an amplification primer.

* * * * *